(12) United States Patent
Barth et al.

(10) Patent No.: US 8,829,178 B2
(45) Date of Patent: Sep. 9, 2014

(54) IMMUNO-RNA-CONSTRUCTS

(75) Inventors: Stefan Barth, Aachen (DE); Ulrich Wüllner, Bielefeld (DE); Inga Neef, Stolberg (DE)

(73) Assignee: Fraunhofer-Gesellschaft zur Forderung der angewandten Forschung e.V., Munich (DE)

( * ) Notice: Subject to any disclaimer, the term of this patent is extended or adjusted under 35 U.S.C. 154(b) by 920 days.

(21) Appl. No.: 12/086,817

(22) PCT Filed: Dec. 21, 2006

(86) PCT No.: PCT/EP2006/070116
§ 371 (c)(1),
(2), (4) Date: Feb. 17, 2009

(87) PCT Pub. No.: WO2007/071777
PCT Pub. Date: Jun. 28, 2007

(65) Prior Publication Data
US 2009/0304717 A1 Dec. 10, 2009

(30) Foreign Application Priority Data
Dec. 21, 2005 (EP) .................................... 05112660

(51) Int. Cl.
*C07H 21/04* (2006.01)
*C12N 15/11* (2006.01)
*C12N 15/113* (2010.01)
*C12N 15/115* (2010.01)

(52) U.S. Cl.
CPC .......... *C12N 15/115* (2013.01); *C12N 2310/14* (2013.01); *C12N 15/111* (2013.01); *C12N 2310/351* (2013.01); *C12N 15/1135* (2013.01); *C12N 2310/3519* (2013.01); *C12N 15/113* (2013.01); *C12N 2310/3513* (2013.01); *C12N 2320/32* (2013.01); *C12N 2310/16* (2013.01); *C12N 2310/11* (2013.01)
USPC ........................................................ 536/24.5

(58) Field of Classification Search
CPC ........................ C12N 2310/11; C12N 2310/15
See application file for complete search history.

(56) References Cited

U.S. PATENT DOCUMENTS

| | | | |
|---|---|---|---|
| 4,946,778 A | 8/1990 | Ladner et al. | |
| 5,583,034 A * | 12/1996 | Green et al. | 435/6.14 |
| 5,670,324 A | 9/1997 | Littman et al. | |
| 5,739,350 A | 4/1998 | Kelly et al. | |
| 5,935,835 A | 8/1999 | Marshall et al. | |
| 6,015,556 A | 1/2000 | Bagshawe | |
| 6,346,406 B1 * | 2/2002 | Ryazanov et al. | 435/194 |
| 2002/0151684 A1 | 10/2002 | Mayer et al. | |
| 2002/0176851 A1 | 11/2002 | Seed et al. | |
| 2003/0104985 A1 | 6/2003 | Matulic-Adamic et al. | |
| 2003/0166512 A1 | 9/2003 | Xie | |
| 2003/0186384 A1 | 10/2003 | Barth et al. | |
| 2003/0198595 A1 | 10/2003 | Goldenberg et al. | |
| 2004/0110928 A1 * | 6/2004 | Crisanti et al. | 530/358 |
| 2004/0204377 A1 | 10/2004 | Rana | |
| 2005/0153915 A1 | 7/2005 | Usman et al. | |
| 2005/0159381 A1 | 7/2005 | McSwiggen et al. | |
| 2005/0176024 A1 | 8/2005 | McSwiggen et al. | |
| 2005/0176025 A1 | 8/2005 | McSwiggen et al. | |
| 2006/0105975 A1 * | 5/2006 | Pendergrast et al. | 514/44 |
| 2006/0280749 A1 | 12/2006 | Rosenblum et al. | |

FOREIGN PATENT DOCUMENTS

| | | |
|---|---|---|
| CA | 2 447 161 A1 | 11/2002 |
| CA | 2447161 A1 | 11/2002 |
| EP | 1 741 781 A2 | 1/2007 |
| EP | 1741781 A2 | 10/2007 |
| WO | 98/41648 A2 | 9/1998 |
| WO | 01/80880 A2 | 11/2001 |
| WO | 02/094185 A2 | 11/2002 |
| WO | 2004/031404 | 4/2004 |
| WO | 2004/044141 A2 | 5/2004 |
| WO | 2004/078215 A2 | 9/2004 |
| WO | 2004/104588 A1 | 12/2004 |
| WO | 2005/040379 A2 | 5/2005 |
| WO | 2005042558 A1 | 5/2005 |
| WO | 2005/059135 A2 | 6/2005 |
| WO | 2005/085470 A1 | 9/2005 |
| WO | 2006/021553 A1 | 3/2006 |
| WO | 2006/114409 A1 | 11/2006 |
| WO | 2007056153 A2 | 5/2007 |
| WO | 2008/012296 A1 | 1/2008 |

OTHER PUBLICATIONS

Arora et al. Cancer Res. 2003: 6894-6899.*
Andre et al., "Aptamer-oligonucleotide binding studied by capillary electrophoresis: Cation effect and separation effeicieny", Electrophoresis, 26:3247-3255 (2005).
Blank et al., "Aptamers as tools for target validation", Current Opinion in Chemical Biology, 9:336-342 (2005).
Brinkmann et al., "Recombinant immunotoxins for cancer therapy", Expert Opin. Biol. Ther., 1(4):693-702 (2001).
Cassiday et al., "Yeast genetic selections to optimize RNA decoys for transcription factor NF-kB", PNAS, 100(7): 3930-3935 (Apr. 1, 2003), XP007902933.
Chaudhary et al., "A rapid method of cloning functional variable-region antibody genes in *Escherichia coli* as single-chain immnotoxins", Pro. Natl. Sci. USA, 87:1066-1070 (Feb. 1990).
Chiu et al., Visualizing a Correlation between siRNA Localization, Cellular Uptake, and RNAi in Living Cells, Chemistry & Biology, 11:1165-1175 (Aug. 2004).

(Continued)

*Primary Examiner* — Kimberly Chong
(74) *Attorney, Agent, or Firm* — Dardi & Herbert, PLLC; Curtis B. Herbert

(57) ABSTRACT

Subject of the invention is a compound, consisting of a targeting moiety which specifically binds to a disease related cell surface marker, a nucleic acid which specifically induces cell death and a linker, wherein the linker covalently links the targeting moiety to the nucleic acid. Subject of the invention are also medicaments comprising the compound and their use as a medicament for the treatment of diseases, including proliferative diseases.

19 Claims, 39 Drawing Sheets

(56) References Cited

OTHER PUBLICATIONS

Crooke, "Antisense Strategies", Current Molecular Medicine, 4:465-487 (2004).
Dykxhoorn et al., "The silent treatment: siRNAs as small molecule drugs", Gene Therapy, 13:541-552 (2006).
Dykxhoorn et al., "Killing the Messenger: Short RNAs That Silence Gene Expression", Molecular Cell Biology, 4:457-467 (Jun. 2003).
Farokhzad et al., "Nanoparticle-Aptamer Bioconjugates: A New Approach for Targeting Prostate Cancer Cells", Cancer Research, 64:7668-7672 (Nov. 1, 2004).
Izquierdo, "Short interering RNAs as a tool for cancer gene therapy", Cancer Gene Therapy, 12:217-227 (2005).
Kaminski et al., "Iodine-131-Anti-B1 Radioimmunotheapy for B-Cell Lymphoma", Journal of Clinical Oncology, 14 (7):1974-1981 (Jul. 1996).
Kapp et al., "Preliminary report: Growth of Hodgkin's lymphoma derived cells in immune compromised mice", Annals of Oncology, 3 (Suppl. 4): S21-S23 (1992).
Karkare et al., "RNA Interference Silencing the Transcriptional Message", Applied Biochemistry and Biotechnolgy, 119:1-12 (2004).
Khaled et al., "Controllable Self-Assembly of Nanoparticles for Specific Delivery of Multiple Therapeutic Molecules to Cancer Cells Using RNA Nanotechnology", Nano Letters, 5(9):1797-1808 (2005).
Leclercq et al., "Cellular Signalling bySphingosine Kinase and Shngosine 1-Phosphate", IUBMB Life, 58 (8):467-472 (Aug. 2006).
Lorenz et al., "Steroid and lipid conjugates of siRNAs to enhance cellular uptake and gene silencing in liver cells", Bioorganic & Medicinal Chemistry Letters, 14:4975-4977 (2004).
Pennell et al., "Designing Immunotoxins for Cancer Therapy", Immunologic Research, 25(2):177-191 (2002).
Scanlon, "Anti-genes: siRNA, Ribozymes and Antisense", Current Pharmaceutical Biotechnology, 5:415-420 (2004).
Selzer et al., "N-ras inhibits apoptosis in human melanoma grown in SCID mice by reciprocal regulation of BCL-2 and the BCL-2 associated protein bax" Radiotherapy and Oncology, 40:S48 (1996), XP004999651, Poster 179.
Song et al., "Antibody mediated in vivo delivery of small interfering RNAs via cell-surface receptors", Nature Biotechnology, 23(6):709-717 (Jun. 2005).
Soutschek et al., "Therapeutic silencing of an endogenous gene by systemic administration of modified siRNAs", Nature, 432:173-178 (Nov. 11, 2004).
Wadgwa et al, "Know-how of RNA interferene and its applications in research and therapy", Mutation Research, 567:71-84 (2004).
Baskin et al., "Copper-free click chemistry for dynamic in vivo imaging", Proc Natl Acad Sci USA, 104: 16793-16797 (2007).
Dilber et al., "Intercellular delivery of thymidine kinase prodrug activating enzyme by the herpes simplex virus protein, VP22," Gene Therapy, 6, 12-71, 1999.
Dyba et al., "Small molecule toxins targeting tumor receptors", Curr Pharm Des, 10:2311-2334 (2004).
Haxhinasto et al., "Synergistic B Cell Activation by CD40 and the B Cell Antigen Receptor," The Journal of Biological Chemistry, vol. 279, No. 4, pp. 2575-2582, 2004.
Hochuli, "Large-scale chromatography of recombinant proteins", Journal of Chromatography, 444:293-302. (1988).
Keppler et al., "Labeling of fusion proteins of O6-alkylguanine-DNA alkyltransferase with small molecules in vivo and in vitro", Methods, 32(4):437-444 (2004).

Lim et al., "Synthesis of Water-Soluble Dendrimers Based on Melamine Bearing 16 Paclitaxel Groups", Organic Letters, 10(2):201-204 (2008).
Meyer et al., "FRET imaging reveals that functional neurokinin-1 receptors are monomeric and reside in membrane microdomains of live cells", PNAS US, 103(7): 2138-2143 (Feb. 14, 2006).
Niemeyer et al., "Detecting antigens by quantitative immuno-PCR", Nature Protocols, 2(8):1918-1930 (2007).
Porath et al., "Metal chelate affinity chromatography, a new approach to protein fractionation", Nature, 258:598-599 (1975).
Shohat et al., "The DAP-Kinase family of protiens: A study of a novel group of calcium-regulated death-promotion kinases," Biochimica et Biophysica Acta 1600: 45-50 (2002).
Steinborn et al., "Application of a wide-range yeast vector (CoMed) system to recombinant protein production in dimorphic *Arxula adeninivorans*, methylotrophic *Hansenula polymorpha* and other yeasts", Microb Cell Fact, 5:33, 2006 (13 pages).
Stöcker et al., "Secretion of functional anti-CD30-angiogenin immunotoxins into the supernatant of transfected 293T-cells", Protein Expression and Purification, 28:211-219 (2003).
Thorpe et al., "Chemokine/chemokine receptor nomenclature" IUIS/WHO Subcommitte on Chemokine Nomenclature, Cytokine, 21:48-49 (2003).
Tur et al., "Recombinant CD64-Specific Single Chain Immunotoxin Exhibits Specific Cytotoxicity against Acute Myeloid Leukemia Cells", Cancer Research, 63:8414-8419 (Dec. 1, 2003).
Wu et al., "Arming Antibodies: prospects and challenges for immunoconjugages", Nature Biotechnology, 23(9): 1137-1146 (Sep. 2005).
Wu et al., "Targeted delivery of methotrexate to epidermal growth factor receptor-positive brain tumors by means of cetuximab (IMC-C225) dendrimer bioconjugates", Mol. Cancer Ther., 5(1):52-59 (Jan. 2006).
Dufner et al., "Harnessing phage and ribosome display for antibody optimisation," Trends in Biotechnology 24 (11):523-529 (2006).
Kampmeier et al., "Rapid optical imaging of EGF receptor expression with a single-chain antibody SNAP-tag fusion protein," Eur J Nucl Med Mol Imaging 37:1926-1934 (2010).
Riemer et al., "Matching of trastuzumab (Herceptin®) epitope mimics onto the surface of Her-2/neu—a new method of epitope definition," Molecular Immunology 42:1121-1124 (2005).
Stancovski et al., "Mechanistic aspects of the opposing effects of monoclonal antibodies to the ERBB2 receptor on tumor growth," Proc. Natl. Acad. Sci. USA 88:8691-8695 (Oct. 1991).
Witte et al., "Monoclonal antibodies trageting the VEGF receptor-2 (Flk1/KDR) as an anti-angiogenic therapeutic strategy," Cancer and Metastasis Reviews 17:155-161 (1998).
Wu et al., "Humanization of a Murine Monoclonal Antibody by Simultaneous Optimization of Framework and CDR Residues," J. Mol. Biol. 294:151-162 (1999).
Yu et al., "Interaction between Bevacizumab and Murine VEGF-A: A Reassessment," Investigative Opthamology & Visual Science, 49(2):522-527 (Feb. 2008).
Barth et al., "Compatible-Solute-Supported Periplasmic Expression of Functional Recombinant Proteins under Stress Conditions", Applied and Environmental Microbiology, 66(4):1572-1579 (Apr. 2000).
Song et al., "Antibody mediated in vivo delivery of small interfering RNAs via cell-surface receptors", Nature Biotechnology, 23(6):709-717(Jun. 2006).
Molecular Cloning: A Laboratory Manual (Third Edition) by Joseph Sambrook and David Russell (1 page), 2001.

* cited by examiner

Full-length aptamer

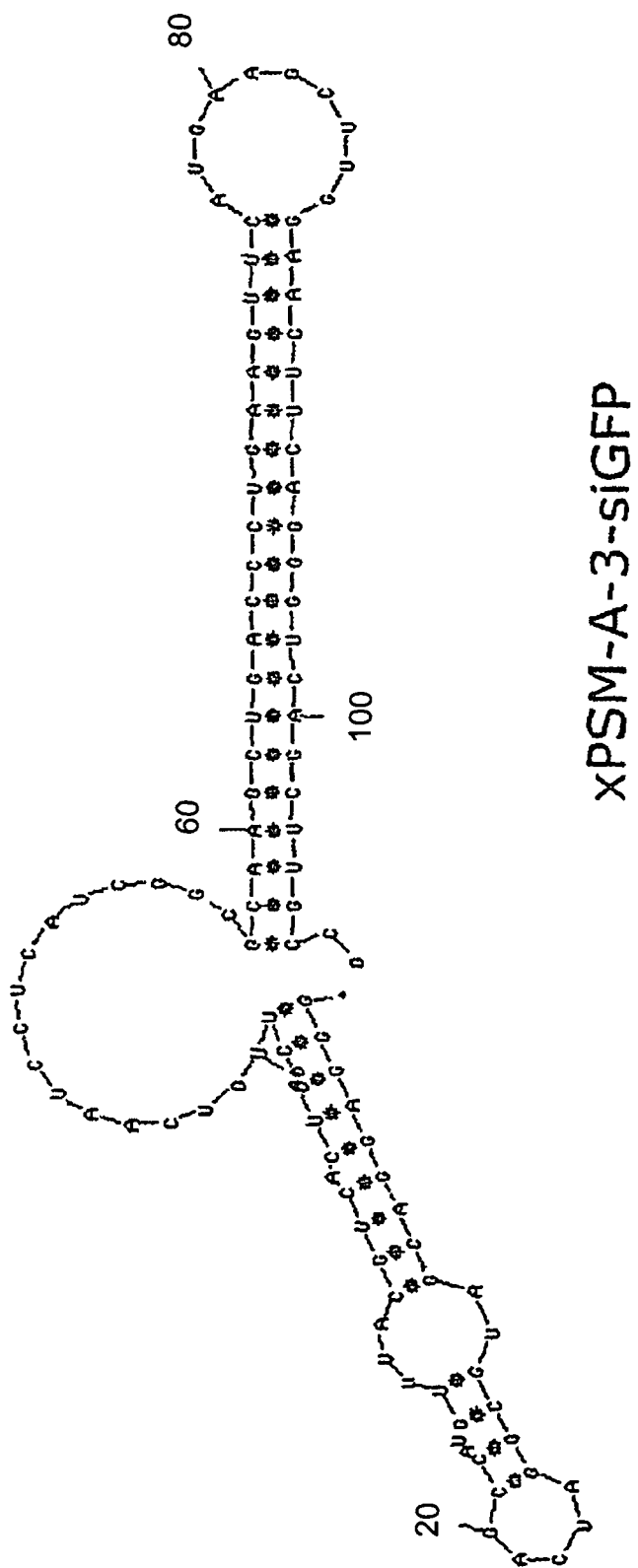
Figure 5C xPSM-A-3-siGFP

The full-length aptamer

Truncated aptamer

Truncated aptamer

Truncated aptamer

PSMA Biv anneal (schematic representation)

SEQUENCE LISTING

<160> NUMBER OF SEQ ID NOS: 21

<210> SEQ ID NO 1
<211> LENGTH: 108
<212> TYPE: RNA
<213> ORGANISM: Artificial
<220> FEATURE:
<223> OTHER INFORMATION: chemically synthesized

<400> SEQUENCE: 1

```
gggaggacga ugcggaucag ccauguuuac gucacuccuu gucaauccuc aucggcgcaa      60
gcugacccug aaguucauga agcuuggaac uucaggguca gcuugccg                 108
```

<210> SEQ ID NO 2
<211> LENGTH: 107
<212> TYPE: RNA
<213> ORGANISM: artificial
<220> FEATURE:
<223> OTHER INFORMATION: chemically synthesized

<400> SEQUENCE: 2

```
gggaggacga ugcggaucag ccauguuuac gucacuccuu gucaauccuc aucggcagcg      60
ccaucaugga caagaauuga agcuucuucu guccaugau ggcgcgg                   107
```

<210> SEQ ID NO 3
<211> LENGTH: 19
<212> TYPE: RNA
<213> ORGANISM: Artificial
<220> FEATURE:
<223> OTHER INFORMATION: chemically synthesized

<400> SEQUENCE: 3

```
aggccuaucu gcccgucaa                                                  19
```

<210> SEQ ID NO 4
<211> LENGTH: 19
<212> TYPE: RNA
<213> ORGANISM: artificial
<220> FEATURE:
<223> OTHER INFORMATION: chemically synthesized

<400> SEQUENCE: 4

```
uugacgggca gauaggccu                                                  19
```

<210> SEQ ID NO 5
<211> LENGTH: 19
<212> TYPE: RNA
<213> ORGANISM: artificial
<220> FEATURE:
<223> OTHER INFORMATION: chemically synthesized

<400> SEQUENCE: 5

```
gcgccaucau ggacaagaa                                                  19
```

<210> SEQ ID NO 6
<211> LENGTH: 19
<212> TYPE: RNA
<213> ORGANISM: Artificial
<220> FEATURE:
<223> OTHER INFORMATION: chemically synthesized

<400> SEQUENCE: 6

```
uucuugucca ugauggcgc                                                  19
```

```
<210> SEQ ID NO 7
<211> LENGTH: 143
<212> TYPE: RNA
<213> ORGANISM: artificial
<220> FEATURE:
<223> OTHER INFORMATION: chemically synthesized

<400> SEQUENCE: 7
gggaauuccg cgugugccag cgaaaguugc guauggguca caucgcaggc acaugucauc      60
ugggcggucc guucgggauc cucggaagcu ugcaagcuga cccugaaguu caugaagcuu    120
ggaacuucag ggucagcuug ccg                                             143

<210> SEQ ID NO 8
<211> LENGTH: 140
<212> TYPE: RNA
<213> ORGANISM: artificial
<220> FEATURE:
<223> OTHER INFORMATION: chemically synthesized

<400> SEQUENCE: 8
gggaauuccg cgugugccag cgaaaguugc guauggguca caucgcaggc acaugucauc      60
ugggcggucc guucgggauc cucgaagcua gcgccaucau ggacaagaau ugaagcuucu    120
ucuuguccau gauggcgcgg                                                 140

<210> SEQ ID NO 9
<211> LENGTH: 22
<212> TYPE: DNA
<213> ORGANISM: Artificial
<220> FEATURE:
<223> OTHER INFORMATION: chemically synthesized

<400> SEQUENCE: 9
gcaagctgac cctgaagttc at                                              22

<210> SEQ ID NO 10
<211> LENGTH: 22
<212> TYPE: DNA
<213> ORGANISM: artificial
<220> FEATURE:
<223> OTHER INFORMATION: chemically synthesized

<400> SEQUENCE: 10
gaacttcagg gtcagcttgc cg                                              22

<210> SEQ ID NO 11
<211> LENGTH: 184
<212> TYPE: DNA
<213> ORGANISM: Artificial
<220> FEATURE:
<223> OTHER INFORMATION: chemically synthesized

<400> SEQUENCE: 11
gggaggacga ugcggaucag ccauguuuac gucacuccuu gucaauccuc aucggcuaaa     60
aauugcgcca ucauggacaa gaauuaauua agggaggacg augcggauca gccauguuua   120
cgucacuccu ugucaauccu caucggcaaa aauucuuguc caugauggcg cgggagctcg   180
aatt                                                                  184

<210> SEQ ID NO 12
<211> LENGTH: 237
<212> TYPE: DNA
<213> ORGANISM: Artificial
```

<220> FEATURE:
<223> OTHER INFORMATION: chemically synthesized

<400> SEQUENCE: 12
gggaggacga ugcggaucag ccauguuuac gucacuccuu gucaauccuc aucggcuaaa    60
auuaggccua ucugcccguc aauuaaaaau ugggaggacg augcggauca gccauguuua   120
cgucacuccu ugucaauccu caucggcagc gccaucaugg acaagaauug aagcuucuuc   180
uuguccauga uggcgcggaa aaaaauugac gggcagauag gccuuugagc ucgaatt      237

<210> SEQ ID NO 13
<211> LENGTH: 85
<212> TYPE: RNA
<213> ORGANISM: Artificial
<220> FEATURE:
<223> OTHER INFORMATION: chemically synthesized

<400> SEQUENCE: 13
gggaggacga ugcggaucag ccauguuuac gucacuccuu gucaauccuc aucggcuaaa    60
aauugcgcca ucauggacaa gaauu                                         85

<210> SEQ ID NO 14
<211> LENGTH: 82
<212> TYPE: DNA
<213> ORGANISM: Artificial
<220> FEATURE:
<223> OTHER INFORMATION: chemically synthesized

<400> SEQUENCE: 14
gggaggacga tgcggatcag ccatgtttac gtcactcctt gtcaatcctc atcggcaaaa    60
attcttgtcc atgatggcgc gg                                            82

<210> SEQ ID NO 15
<211> LENGTH: 71
<212> TYPE: RNA
<213> ORGANISM: Artificial
<220> FEATURE:
<223> OTHER INFORMATION: chemically synthesized

<400> SEQUENCE: 15
gggaggacga ugcggaucag ccauguuuac gucacuccuu gucaauccuc aucggcagac    60
gacucgcccg a                                                        71

<210> SEQ ID NO 16
<211> LENGTH: 56
<212> TYPE: RNA
<213> ORGANISM: Artificial
<220> FEATURE:
<223> OTHER INFORMATION: chemically synthesized

<400> SEQUENCE: 16
gggaggacga ugcggaucag ccauguuuac gucacuccuu gucaauccuc aucggc        56

<210> SEQ ID NO 17
<211> LENGTH: 82
<212> TYPE: RNA
<213> ORGANISM: Artificial
<220> FEATURE:
<223> OTHER INFORMATION: chemically synthesized

```
<400> SEQUENCE: 17
gggaauuccg cgugugccag cgaaaguugc guauggguca caucgcaggc acaugucauc    60
ugggcggucc guucgggauc cu                                            82

<210> SEQ ID NO 18
<211> LENGTH: 56
<212> TYPE: RNA
<213> ORGANISM: Artificial
<220> FEATURE:
<223> OTHER INFORMATION: chemically synthesized

<400> SEQUENCE: 18
gggaggacga ugcggaucag ccauguuuac gucacuccuu gucaauccuc aucggc        56

<210> SEQ ID NO 19
<211> LENGTH: 173
<212> TYPE: RNA
<213> ORGANISM: Artificial
<220> FEATURE:
<223> OTHER INFORMATION: chemically synthesized

<400> SEQUENCE: 19
gggaggacga ugcggaucag ccauguuuac gucacuccuu gucaauccuc aucggcuaaa    60
aauugcgcca ucauggacaa gaauuaauua agggaggacg augcggauca gccauguuua   120
cgucacuccu ugucaauccu caucggcaaa aauucuuguc caugauggcg cgg          173

<210> SEQ ID NO 20
<211> LENGTH: 56
<212> TYPE: RNA
<213> ORGANISM: Artificial
<220> FEATURE:
<223> OTHER INFORMATION: chemically synthesized

<400> SEQUENCE: 20
gggaggacga ugcggaucag ccauguuuac gucacuccuu gucaauccuc aucggc        56

<210> SEQ ID NO 21
<211> LENGTH: 198
<212> TYPE: RNA
<213> ORGANISM: Artificial
<220> FEATURE:
<223> OTHER INFORMATION: chemically synthesized

<400> SEQUENCE: 21
gggaggacga ugcggaucag ccauguuuac gucacuccuu gucaauccuc aucggcuaaa    60
auuaggccua ucugcccguc aauuaaaaau ugggaggacg augcggauca gccauguuua   120
cgucacuccu ugucaauccu caucggcagc gccaucaugg acaagaauug aagcuucuuc   180
uuguccauga uggcgcgg                                                 198
```

US 8,829,178 B2

IMMUNO-RNA-CONSTRUCTS

RELATED APPLICATION

This application claims priority to PCT Application No. PCT/EP2006/070116 filed Dec. 21, 2006, which claims priority to European Patent Application No. 05112660.5 filed Dec. 21, 2005, each of which are hereby incorporated herein by reference.

TECHNICAL FIELD OF THE INVENTION

Subject of the invention is a compound consisting of a targeting moiety, which specifically binds to a disease related cell surface marker, a nucleic acid moiety which specifically induces cell death and a linker, wherein the linker covalently links the targeting moiety to the nucleic acid moiety. Subject of the invention are also therapeutic uses of the compound, medicaments comprising the compound, DNAs and cells related thereto.

INTRODUCTION TO THE INVENTION

Medications currently available for the treatment of proliferative diseases, such as chemotherapeutic agents, have a disadvantage of inducing considerable side effects due to their relative non-specificity. It has been attempted to moderate these by various therapeutic concepts. One potential approach is the use of immunotherapeutic agents to increase the specificity of medication. This approach has been especially useful for the treatment of tumors.

One type of immunotherapeutic agents are immunotoxins (ITs). An immunotoxin comprises a monoclonal antibody (moAb) or a recombinant antibody fragment with specificity to a surface marker of a diseased target cell which is coupled to a cytotoxic reagent. Another type of immunotherapeutic agents are anti-immunoconjugates. They comprise a polypeptidic structure as causative agent for the pathogenesis of autoimmune diseases, tissue reactions and allergies which is again coupled to a catalytically-active cytotoxin. Cytotoxic agents are currently selected from toxins or radioactive elements. An immunotherapeutic wherein the cytotoxic agent is a radioactive element is called radioimmunoconjugate. Immunotoxins and immunoconjugates have been developed and used for the treatment of different malignancies. Radioactively labeled anti-B-cell moAb applied in patients with B-cell lymphomas resulted in tumor regressions and even complete remissions (1). In contrast, the results with moAb against solid tumors were rather disillusioning.

The relatively large size of ITs used in these clinical studies seemed to interfere with their ability to penetrate the tumors. The low tumor penetration rate posed a particularly challenging problem for poorly vascularized tumors. In order to obtain better tissue and tumor penetration as well as generally improved diffusion properties, the ITs were miniaturized. It was speculated that smaller ITs would be less immunogenic because of the reduced size of the antigenic determinants (2). Therefore proteolytically cleaved antibody fragments were initially conjugated to the above mentioned effector functions (radioactive labeled elements or toxins).

Improved cloning techniques allowed the preparation of completely recombinant ITs. Coding region of immunoglobulin light and heavy chain variable regions, amplified by polymerase chain reaction, are joined together by a synthetic linker (e.g. $(Gly_4Ser)_3$). The resulting single chain fragment of the variable region genes (scFv) was genetically fused to a coding region of a catalytically active enzyme including cytotoxically active proteins or polypeptides (3).

The peptidic cell poisons which have been mainly used to date are the bacterial toxins diphteria toxin (DT), *Pseudomonas exotoxin* A (PE) and the plant-derived Ricin-A (RA) (4). The mechanism of cytotoxic activity is essentially the same in all of these toxins despite of their different evolutionary backgrounds. The enzyme knocks down protein biosynthesis by inhibiting the insertion of eucaryotic elongation factor 2 (eEF2), which is the key element for RNA translation into protein, into its binding groove in ribosomes. This is done by a) direct modification of eEF2 (DT, PE), or by inactivation of eEF2-binding site within the 28S-rRNA subunit of ribosomes (RA).

As alternative agents to peptidic cell poisons, nucleic acids like small interfering RNAs (siRNAs) or a short hairpin RNA (shRNA), an antisense DNA or RNA, a double stranded RNA (dsRNA) or a micro RNA (miRNA) might be used to downregulate specific key elements of regulative pathways within a cell. Further more down regulation of disease causing proteins can be achieved through inhibitory aptamers. The biological function of the target protein is inhibited by binding of the inhibitory aptamer thus this class of molecules can also be used to achieve therapeutic effects.

Song et al., 2002, disclose delivery of small interfering RNAs (siRNAs) into HIV-infected or envelope-transfected cells by a protamine-antibody fusion protein. The fusion protein has a high affinity for nucleic acids and is loaded with siRNA. In the resulting complex the RNA is bound non-covalently. However, apoptosis in target cells was achieved only mildly by using a mixture of different siRNAs targeting different proteins.

According to Khaled et al., an RNA aptamer is used to deliver siRNA molecules to target cells in a complex, wherein the aptamer moiety is non-covalently attached to the siRNA part. The complex is a trimer, one part of which contains the aptamer portion and another part the siRNA. Both monomers are assembled via loop to loop interactions.

WO 2005/059135 discloses the delivery of siRNAs into mammalian nerve cells by applying siRNA molecules alone or complexed with a delivery reagent, such as liposomes, for delivery into the target cell.

US 2003/0166512 A1 discloses antisense oligonucleotides and siRNAs which are covalently coupled to mobile proteins (serum proteins) like albumin in order to increase serum half life and reduce immunogenicity of unconjugated nucleic acids. The protein conjugates do not have a targeting function for cell specific delivery of therapeutic oligonucleotides or siRNAs.

CA 2447161 discloses conjugates, degradable linkers and compositions consisting of folate, galactose etc. and of biologically active compounds are characterized. Antibodies or aptamers are used, but have no targeting function and replace the siRNA.

US 2004/0204377 discloses methods for delivery of siRNAs into cells by coupling to dendrimers or peptides. The peptides are unspecific cell penetrating peptides. The cellular uptake of the coupled siRNA is enhanced when compared to free siRNA, but there is no targeting function for cell specific delivery of therapeutic siRNAs.

Recently several reports and patents about the therapeutic application of siRNAs were published. Most promising approach in this respect is the silencing of disease-related genes. US2005/0159381 A1 claims siRNA sequences targeting genes like BCR-ABL and ERG which are associated with chromosomal translocation and cancer progression. US2005/0176025 describes siRNAs that induce apoptosis in target cells via knock down of Bcl-2 family proteins. In WO 2005/040379 growth inhibition of tumour cells should be induced through siRNAs targeting Ras family proteins which is a common oncogene protein family known to be over expressed in various cancers. Patent WO 98/41648 discloses siRNAs that are important for cell viability. Most of the genes claimed belong to genes which regulate cell deviation processes. Besides the direct silencing of disease related proteins siRNAs can also be used in order to sensitize cells for certain kinds of further manipulations. In Patent WO 2005/042558 A1 siRNAs targeting various proteins belonging to the family of IAP (inhibitor of apoptosis proteins) are described. Knock down of these proteins should result in higher sensitivity against small molecule toxins like Paclitaxel.

In addition several review articles about the therapeutic potential of siRNAs are published in the literature (5, 6). Common sense in all these reviews is that besides the identification of highly potent siRNAs the development of efficient and safe and cell type specific delivery strategies for the in vivo administration of active siRNAs have to be developed. In WO 2004/044141 A2 the conjugation of siRNAs to molecules which potentially could provide a targeting function are claimed. These molecules are small molecule ligands for cell surface receptors like vitamins and peptides. US 2003/0104985 A1 describes the conjugation of biologically active compounds to molecules like folate, human serum albumin or N-acetylgalactosamine which might mediate specific binding to cell surface proteins. The first report about the successful in vivo administration of chemically modified siRNAs was published by Soutchek et al. In this study cholesterol conjugated siRNAs showed silencing activity when injected into the tail vein of mice. In addition cellular penetration of siRNAs could be achieved by Rana and coworkers who used the cell penetrating peptide TAT to shuttle the siRNA across the cell membrane (7).

SUMMARY

All these valuable patents or scientific reports contribute to the development of siRNA based drugs. But in none of the afore mentioned studies or patents the problem of siRNA delivery was approached by covalent conjugation of the siRNA moiety to an aptamer or a full length antibody. The problem underlying the present invention is to provide medications based on therapeutic RNAs which avoid the above mentioned problems. Specifically, medicaments of the invention should be highly specific without causing severe side effects. They should be highly efficient in target cells without significantly affecting other cells.

Surprisingly, the problems identified above are solved by compounds, DNAs, medicaments, uses thereof and methods of any of claims 1 to 24 as published in PCT Pub. No. WO 2007/071777. According to the invention, the aptamer siRNA conjugates are constitutively active being covalently linked to a high molecular weight complex like an aptamer or a polypeptide and do not require further processing e.g. cleavage of linker sequences to achieve full biological activity. If the nucleic acid moiety is an inhibitory aptamer the binding activities of both moieties e.g. the cell surface binding activity and the binding activity of the inhibitory aptamer remain unaffected. Additionally it is surprising that increasing the avidity of the targeting moiety e.g. the aptamer leads to compositions which are far superior to state of the art delivery vehicles used for the cell type specific delivery of siRNAs up to now.

Surprisingly, the problems identified above are solved by compounds, DNAs, medicaments, uses thereof and methods of any of claims 1 to 21 as published in PCT Pub. No. WO 2007/071777. According to the instant patent application, the aptamer siRNA conjugates are constitutively active being covalently linked to a high molecular weight complex like an aptamer or a polypeptide and do not require further processing e.g. cleavage of linker sequences to achieve full biological activity. If the nucleic acid moiety is an inhibitory aptamer the binding activities of both moieties e.g. the cell surface binding activity and the binding activity of the inhibitory aptamer remain unaffected. In comparison to protein-based immunotherapeutics targeting cell surface antigens as exemplified for recombinant immunotoxins, an increase in binding valency is not necessarily associated with dramatic but slight changes of activity and thus can not be predicted. Data to this kind of nucleic acid based constructs as described in this patent application are not available. Thus it is very surprising that increasing the avidity of the targeting moiety e.g. the aptamer leads to compositions which are far superior to the monovalent constructs. One general way to increase the avidity of various aptamers is the separation of the two aptamer moieties by a sufficiently long double stranded linker sequence. This linker sequence provides a high degree of rigidity which ensures independent folding of the aptamer moieties incorporated. The problems of unspecific side effects as well as immunogenicity are solved by this invention by not coupling siRNAs to proteins as specific ligands but to a nucleic acid, which is in general less or not immunogenic and which induces sequence specific mRNA degradation.

The problems of unspecific side effects as well as immunogenicity are solved by this invention by not coupling siRNAs to proteins as specific ligands but to a nucleic acid, which is in general less or not immunogenic and which induces sequence specific mRNA degradation.

BRIEF DESCRIPTION OF THE FIGURES

FIG. 5C depicts xPSM-A-3siGFP as in SEQ ID NO:1.

DESCRIPTION OF PREFERRED EMBODIMENTS OF THE INVENTION

Figure 1:
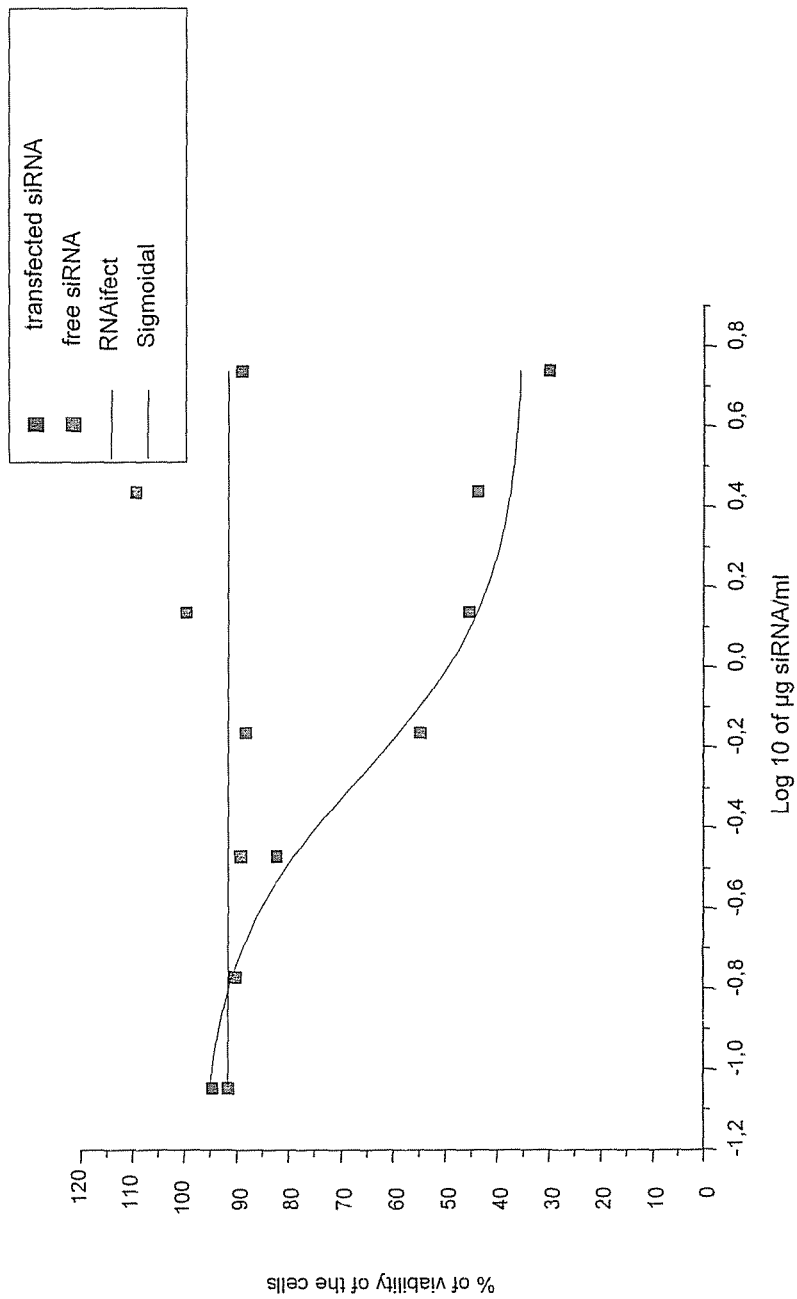
FIG. 1 is a plot of an XTT-viability assay of L540 cells.
Figure 2:
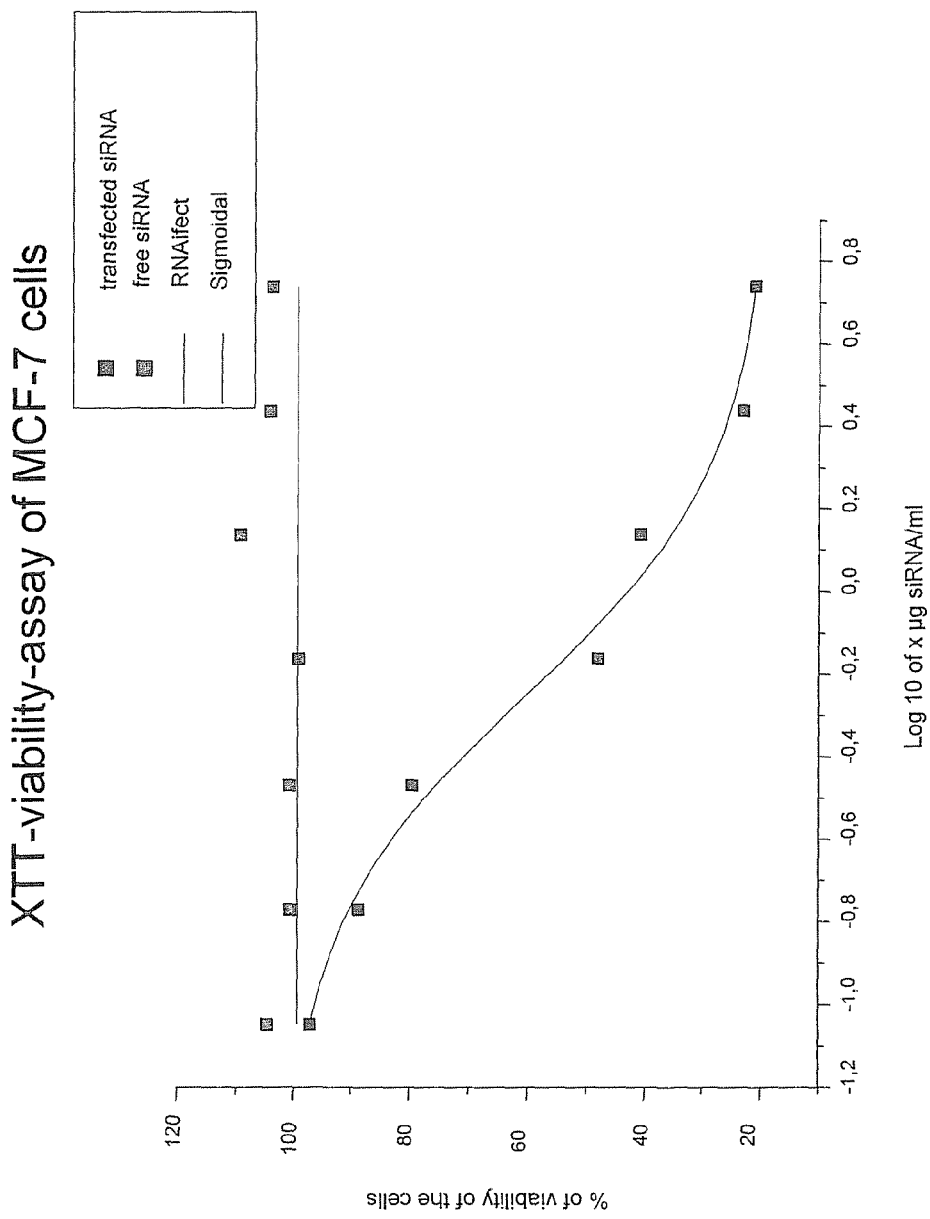
FIG. 2 is a plot of an XTT-viability assay of MCF-7 cells.
Figure 3:
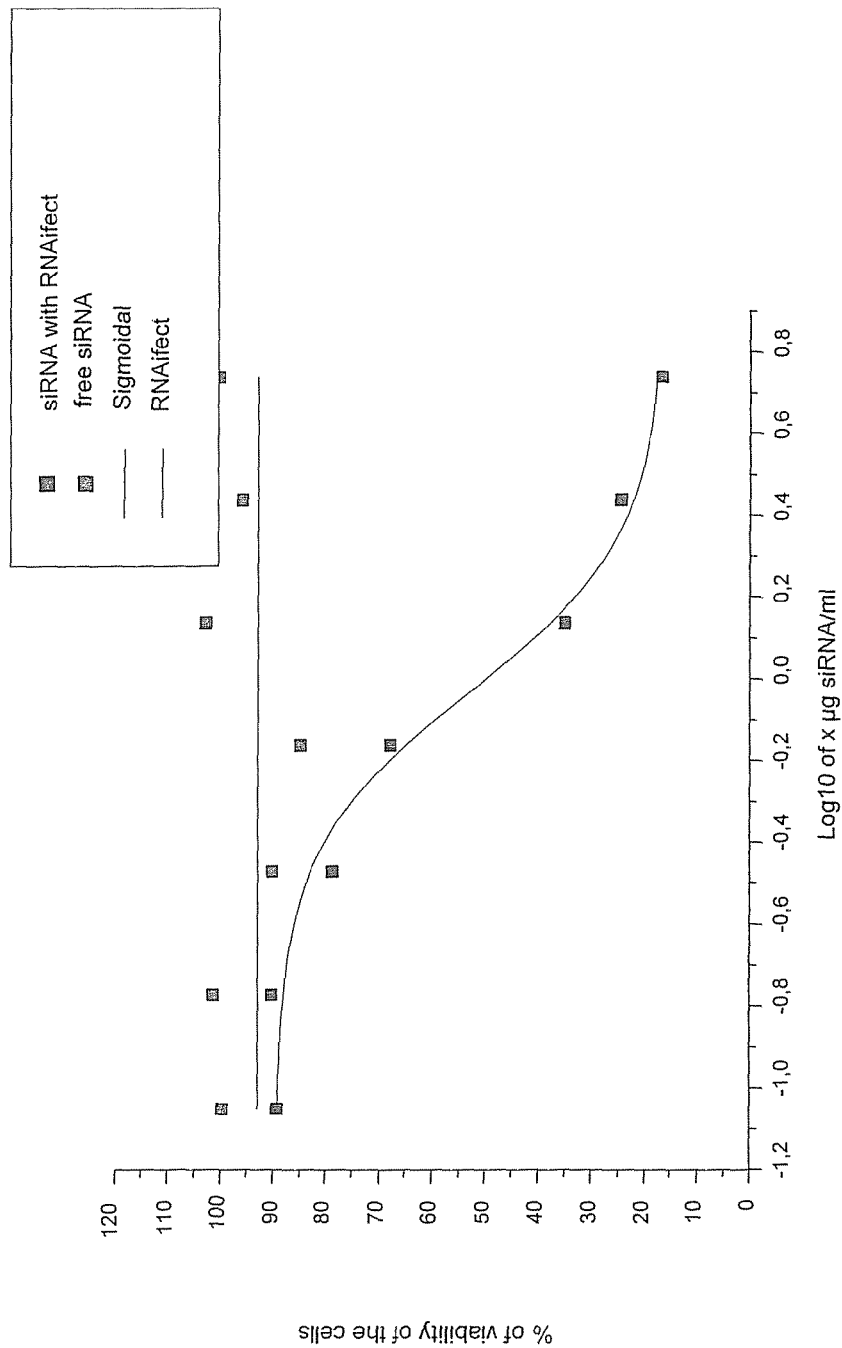
FIG. 3 is a plot of an XTT-viability assay of 293T cells.
Figure 4:
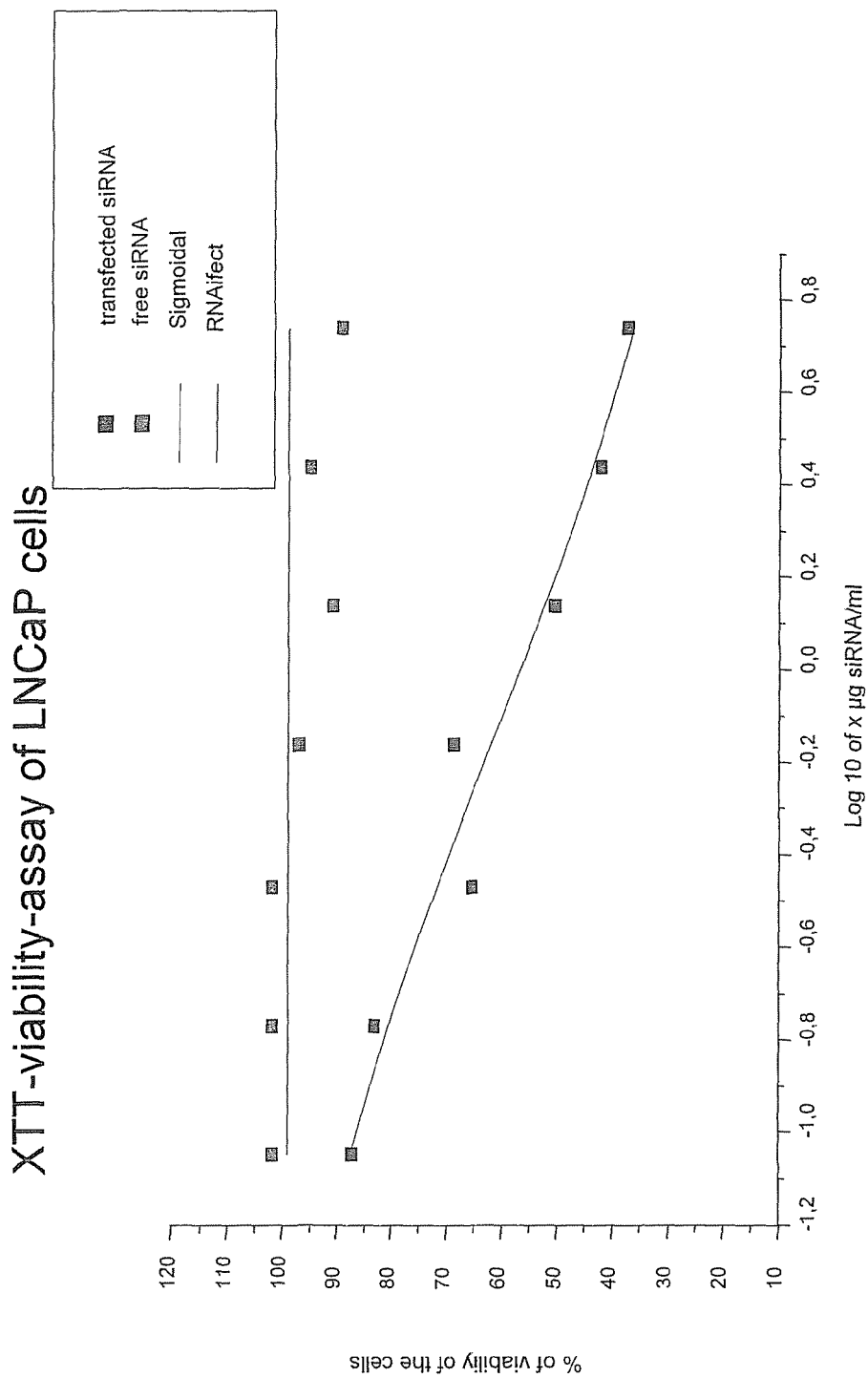
FIG. 4 is a plot of an XTT-viability assay of LNCap cells.

In the compound of the present invention, the nucleic acid moiety is preferably a small interfering RNA (siRNA), a short hairpin RNA (shRNA), an antisense DNA or RNA, a double stranded RNA (dsRNA) or a micro RNA (miRNA) or inhibitory aptamer. In the present invention nucleic acids like siRNAs are covalently coupled to the targeting moiety which renders these complexes more stable because the siRNA part is not prone to dissociate from the targeting moiety. If the siRNA is only bound by complex formation this complex might dissociate during in vivo delivery which leads to reduced therapeutic efficacy because the siRNA payload is reduced and in addition free siRNA molecules might cause side effects in non targeted tissue or cells. In the case of the siRNA aptamer conjugates one also has perfect control over the stoichiometry since siRNA and aptamer part are transcribed from one DNA strand.

In a preferred embodiment, in the compound of the invention one or more targeting moieties are linked to one or more nucleic acid moieties. In this embodiment, since both moieties are covalently attached in a site directed manner the ratio of the two moieties is always distinct and the compound is not a randomly X-linked aggregate of the two moieties. This means that constructs of present invention can comprise multiple targeting moieties which results in an increased avidity and multiple nucleic acid moieties which increases the biological effective e.g. siRNA payload per molecule.

As used herein, "cell death" refers to apoptosis and necrosis. The nucleic acid moieties of the compounds of the invention preferably induce apoptosis.

A "linker" according to the invention is a molecule which is introduced into the compound at a specified position. Preferably, the compound comprises one or more linker molecule.

In a preferred embodiment, the invention uses or combines two mechanisms to specifically regulate gene expression: antisense technology and RNA interference (RNAi) (8). Antisense technology exploits oligonucleotides or analogues thereof, which bind to target RNAs via Watson-Crick hybridization (9). Once bound, the antisense agent induces the degradation of the target mRNA via RNAse H and thus prevents the production of undesired protein.

RNA interference is a gene silencing phenomenon whereby double-stranded RNAs trigger the specific degradation of a homologous mRNA (10). The specific dsRNAs are processed into small interfering RNA (siRNA) which serve as a guide for cleavage of the homologous mRNA in the RNA-induced silencing complex (RISC) (11). The discovery of RNAi, a mechanism that already existed in the most primitive single-celled organism to protect them from viruses (viral RNA), has been heralded as a major scientific breakthrough and represents one of the most promising and rapidly advancing frontiers in biology and drug discovery today. RNAi is a natural process of gene silencing that occurs in organisms ranging from plants to mammals. RNAi was shown to selectively turn off the disease gene in a mouse model (12). By harnessing the natural biological process of RNAi occurring in cells, a major new class of medicines, known as RNAi therapeutics, is created. RNAi therapeutics target the 'root' genetic cause of diseases by potently silencing specific messenger RNAs, thereby preventing the disease-causing proteins from being produced. RNAi therapeutics have the potential to treat malignant diseases and help patients in a fundamentally new way (13).

In spite of the promising results of antisense technology and RNAi in vitro the key problem according to the state of the art was the specific delivery of active RNAs into target cells. RNA is not able to penetrate into target cells by itself. In vitro, the RNA was transfected by lipofection or electroporation into the cytosol of the cell. For in vivo experiments these methods are not applicable.

According to the present invention, the problems of poor cell penetration capacities of the nucleic acid moieties are solved by conjugating them to a targeting moiety which mediates specific cellular uptake. This can be achieved by covalently conjugating the nucleic acid moieties to cell surface specific ligands which e.g. induce receptor mediated endocytosis. The invention allows the cell specific delivery of biologically active RNAs in vivo.

In a preferred embodiment, a ligand could be an antibody, a derivative or fragment thereof, a diabody or an aptamer a multimeric aptamer and combinations thereof. Preferably, the antibody is a monoclonal or full-length antibody. The fragments and derivatives of the antibody are those which preserve the specific binding properties to the antigen. The antibody fragment might be part of a fusion protein.

Aptamers are (usually short) strands of oligonucleotides (DNA or RNA) that can adopt highly specific three-dimensional conformations. Specifically binding aptamers have been selected from random pools based on their binding ability to nucleic acids, proteins, small organic compounds and even entire organisms (14). Aptamers are designed to have appropriate binding affinities and specificities towards certain target molecules (e.g. Her3 on MCF-7 cells, PSMA on LNCaP cells) (15). Because of their highly specific binding activities these molecules can be used for many potential applications in medicine and biotechnology (16). In some cases it was observed that aptamers induced receptor mediated endocytosis after binding to their cell surface specific antigen (e.g. PSMA on LNCaP cells). In particular, the targeting moiety of the invention is represented by at least one, preferably at least two aptamers.

Thus, according to this invention, the nucleic acid moiety which specifically induces mRNA degradation might on the one hand be covalently linked to a protein or on the other hand to an aptamer. After e.g. receptor-mediated endocytosis the compound is translocated into the cytosol where the RNA portion of the compound can induce sequence specific mRNA degradation.

Surprisingly, according to the invention, the nucleic acid moiety, e.g. the siRNA, is covalently coupled to the targeting moiety, e.g. to the protein or the aptamer without loosing the degradation activity of the nucleic acid and the binding activity of the targeting moiety. A compound is generated in which e.g. the siRNA can still trigger the RNAi cascade.

Preferably, in the case of conjugation of a siRNA to a protein-based binding ligand the coupling is achieved using a heterobifunctional linker thereby crosslinking RNA and protein by forming a disulphide bridge between RNA and protein. In the case of the aptamer as the specific binding ligand, a siRNA is preferably genetically fused to the aptamer.

The present invention concerns a synthetic compound formed of at least one targeting moiety and at least one nucleic acid moiety whereby the targeting moiety comprises a binding domain for extra-cellular surface structures that internalises upon binding of the targeting moiety of said compound. The nucleic acid moiety consists of at least one nucleic acid molecule and/or a modified nucleic acid molecule which upon internalisation induces sequence specific mRNA degradation or sequence specific inhibition of translation. This leads to reduced synthesis of the protein encoded by the corresponding mRNA and therefore to modulation of protein function, resulting in cell death.

The compounds of the invention selectively bind to disease related cell surface markers. The binding specificity is mediated by the targeting moiety. Diseased cells often develop significant differences in their cell surface composition in comparison to their normal counterparts: these mainly include different expression pattern or increased expression level of cell surface proteins/antigen or altered cell surface glycosylation status. These morphological differences can be exploited to generate targeting moieties which selectively bind to these disease specific cell surface antigens or corresponding unique epitopes on these antigens. Upon binding of the compounds to the cells, the compounds are internalized by the cells.

Therefore, the compounds of the invention eliminate diseased cells without significantly affecting their normal counterparts or non diseased cells even within or originating from the same tissue. The targeting moiety of the invention is chosen with respect to the therapeutic application. For instance, if tumour cells of a specific type shall be destroyed, the targeting moiety is selected such that it specifically binds to a known tumour cell surface marker.

As used herein, "a disease related cell surface marker" is a cell surface structure, often a protein or a sugar or a glycosylated protein, which is found in increased amounts on the cell surface of the cell affected by the disease, or preferably in significantly higher quantities than on the normal cell.

Preferably, the marker is present on the cell surface of the diseased cell at levels more than 2, 5, 10 or 100 times higher than on corresponding cells not affected by the disease. "Specifically" means, that the targeting moiety is a selective binding partner for the cell surface marker.

In a preferred embodiment, the targeting moiety is an actively binding structure like an antibody. In preferred embodiments of the invention, the targeting moiety is selected from the group consisting of antibodies or their derivatives or fragments thereof, and/or non-proteinogenic molecules such as nucleic acids, especially aptamers which are DNA or RNA molecules or modified DNA or RNA molecules which specifically bind structures present on cell surfaces.

In other preferred embodiments, the targeting moiety is a molecule with specific receptor binding activity selected from the group consisting of carbohydrates, lipids, vitamins, small receptor ligands, cell surface carbohydrate binding proteins and their ligands such as lectins, r-type lectins, galectins and their derivatives, receptor binding molecules such as natural ligands to the cluster of differentiation (CD) antigens, like CD30, CD40, etc. cytokines such as chemokines, colony stimulating factors, type-1 cytokines, type-2 cytokines, interferons, interleukins, lymphokines, monokines, etc., and/or adhesion molecules including their derivatives and mutants, and/or derivatives or combinations of any of the above listed actively binding structures.

Preferably, the targeting moiety specifically binds to CD antigens, cytokine receptors, hormone receptors, growth factor receptors, ion pumps, multimeric extracellular matrix proteins, metallo proteases or channel-forming proteins.

The targeting moiety may also be selected from the group of passively binding structures consisting of allergens, preferably peptidic or recombinant allergens, allergen-idiotypical antibodies, autoimmune-provoking structures, tissue-rejection-inducing structures, immunoglobulin constant regions and their derivatives, mutants or combinations thereof. The compound of the present invention is directed by its targeting moiety to the target cell surface, which comprises a binding partner for one of the above mentioned preferred targeting moieties. In a further embodiment the targeting moiety of the compound has a higher valency by comprising two or more identical and/or different binding structures.

The compound of the invention comprises a nucleic acid moiety, which induces cell death upon internalization into the target cell. Preferably, the nucleic acid moiety induces sequence specific mRNA degradation or sequence specific inhibition of translation. The nucleic acid moiety may be chemically modified, for instance by modifying the 2' position of the ribose moiety which leads to increased nuclease resistance. The nucleic acid moiety may consist of single stranded DNA and/or chemically modified single stranded DNA, or of single stranded RNA and/or chemically modified single stranded RNA or of double stranded RNA and/or chemically modified double stranded RNA. If the nucleic acid moiety is double stranded RNA, both RNA strands can be covalently linked via a hairpin loop. If the targeting moiety is a protein, the compound is preferably produced by modifying the nucleic acid with a reactive chemical group, which is induced to form a covalent bond with the targeting moiety. If the targeting moiety carries a tag which is encoded by its amino acid sequence, the nucleic acid moiety can be covalently conjugated to the targeting moiety in a site directed manner. Upon entry into the target cell, in a preferred embodiment the covalent bond is cleaved, which leads to dissociation of the targeting moiety and the nucleic acid moiety of the given compound. If the targeting moiety is a nucleic acid, the nucleic acid moiety is preferably fused to the targeting moiety via a phosphodiester bond in the sugar phosphate backbone. In a further preferred embodiment, both functionalities are separated by a linker sequence in order to maintain a properly folded and active compound. If the targeting moiety, the linker and the nucleic acid moiety are RNA, they may be genetically fused. This means that the compound is obtainable by in vitro or in vivo transcription.

The targeting moiety binds to a cell surface receptor of a target cell and mediates subsequent translocation of the compound into the cytosol of the target cell. A target cell is defined by the ability of the targeting moiety to bind to at least one structure present on its cell surface.

Preferably, the nucleic acid moiety can induce sequence specific inhibition of translation of any mRNA of a target cell. As a further embodiment of this invention, the nucleic acid moiety induces translational inhibition of genes which affect the cell-regulatory pathways, for example by altering the function, gene expression or viability of the target cell. In a preferred embodiment, the nucleic acid moiety induces the translational inhibition of genes which leads to apoptosis in the target cell. For example, these genes are those which code for proteins directly involved in protein synthesis like eukaryotic elongation factor 2 (eEF-2), or are known to negatively regulate the apoptotic pathway which means that knock down of these proteins could induce apoptosis in a target cell. Relevant proteins are for instance Bcl2, Bcl-XL, Bcl-W, Mcl-1, A1, Ced9, E1B19K or BHRF1. Some Bcl-2 binding proteins also comprise anti-apoptotic effects like Bag-1, Raf-1, Calcineurin, Smn, Beclin, ANT and VDAC. In addition knock down of IAP-1, IAP-2, Survivin, and x-IAP can induce apoptosis. Further antiapoptotic proteins are, IKK-α, IκB, or NF-κB, FLIP, Akt, PI3K or PDK1.

A further embodiment of this invention is a compound comprising at least one further moiety, which enables purification and/or detection of the compound or its moieties and/or facilitates translocation of at least the nucleic acid moiety into the target cell and intracellular separation therein and/or activation of the nucleic acid moiety.

Specific embodiments of the invention are the chemical coupled compound named ki4-siEEF2. This molecule consist of a protein as the targeting moiety and chemically modified siRNA as the gene silencing moiety. The chemical modifications of the siRNA portion enables the covalent conjugation to the protein ligand (ki4 antibody) in addition the chemical modifications lead to increased nuclease stability.

An other specific embodiment of the invention are the RNA based targeting constructs xPSM-A-3, A30-siEEF2, PSMB1-siEEF2, PSMB2-siEEF2, and PSMA biv anneal-siEEF2. The construct A30-siEEF2 consist of RNA. The constructs xPSM-A-3, PSMB1-siEEF2, PSMB2-siEEF2, and PSMA biv anneal-siEEF2 consist of chemically modified RNA. The siRNA portion of A30-siEEF2 consists of RNA and the siRNA portion of all other constructs consists of chemically modified RNA. Except PSMA biv anneal-siEEF2 the siRNA portion is genetically fused to the targeting moiety which means that these molecules are obtainable from one single DNA template.

The sequence of the constructs PSMB1-siEEF2 and PSMB2-siEEF2 are rationally designed in a way that according to the RNA secondary structure prediction algorithm Mfold 3.2 (as published at http address: //molbio.info.nih.gov/molbio-nih/mfold.html) they consist of two independently folding functional aptamer units. The two aptamer units are separated by short double stranded spacer sequences which assist proper folding. In case of PSMA biv anneal-siEEF2 two aptamer moieties are joined noncovalently by introducing complementary 3' overhang sequences which are annealed in a separate reaction. These modifications lead to increased avidity of these RNA constructs. Since the spacer sequences have to be double stranded the gene silencing moiety of these constructs can be found within the spacer sequences. According to the number of spacer sequences used the number of functional gene silencing moieties can be increased (PSMAB1-siEEF2 carries one siRNA moiety, PSMAB2-siEEF2 displays two siRNA moieties).

Surprisingly according to current invention the increase of binding moieties and the increase of functional siRNA sequences within one delivery unit leads to higher biological efficacy.

Preferably, the invention allows the cell type specific delivery of defined, apoptosis inducing nucleic acids into target cells.

A further embodiment of the invention is a RNA comprising a targeting moiety, a linker and a moiety for inducing cell death. The RNA is obtainable by transcription of a respective DNA.

This invention also embodies cells, organs and non-human animals synthesizing complete compounds or individual components thereof after having been transfected with nucleic acid molecules coding for said compounds of the present invention.

In case of the nucleic acid moiety inhibiting translation of a gene which is involved in modulation of cell signaling pathways, the present invention embodies an organ and/or tissue and/or cell specific delivery vehicle for transporting biologically active nucleic acids to target cells.

Preferably, the nucleic acid moiety inhibits translation of a gene which is crucial for cell viability. The inventive compounds are useful as drugs for various diseases, such as cancerous or non-cancerous proliferative diseases, allergies, autoimmune diseases and/or chronic inflammation.

The compound according to the invention is a heterologous conjugate comprising at least two domains, i.e. one effector domain and at least one cell-specific binding domain. The compound according to the invention is usable for diagnosis and therapy of diseases. The publications, patents and patent applications cited previously or below are hereby incorporated by reference.

The compounds of the invention are chimeric molecules in which a targeting moiety is a cell-binding molecule which can be ether an aptamer, which is a specifically binding DNA or RNA molecule, or a monoclonal antibody or fragments thereof that are chemically coupled or genetically fused to the nucleic acid moiety which consists of antisense oligonucleotides, siRNA's or micro RNA's. The term "immuno-RNA constructs" is a synonym of the present invention.

As used herein the term "targeting moiety" represents the actively binding structure of the compound of present invention, which mediates specific binding to a disease related cell surface marker. The targeting moiety is selected from the group of actively binding structures consisting of antibodies or their derivatives or fragments thereof, synthetic peptides such as scFv, minitopes, etc. or chemical molecules such as mono, bi- or multivalent DNA or RNA aptamers, which are specifically binding nucleic acid molecules or derivatives thereof, carbohydrates, lipids, peptides, vitamins, etc., and/or small molecules with up to 100 atoms with receptor-binding activity like ligands, in particular single atoms, peptidic molecules, non-peptidic molecules, etc, and/or cell surface carbohydrate binding proteins and their ligands such as lectins, r-type lectins, galectins and their derivatives, matrix proteins, metalloproteases and/or receptor binding molecules such as natural ligands to the cluster of differentiation (CD) antigens, like CD30, CD40, etc., cytokines such as chemokines, colony stimulating factors, type-1 cytokines, type-2 cytokines, interferons, interleukins, lymphokines, monokines, etc., and/or adhesion molecules including their mutants, and or their derivatives or combinations of any of the above listed of actively binding structures, which bind to CD antigens, cytokine receptors, hormone receptors, growth-factor receptors, ion pumps, channel-forming proteins. The targeting moiety may also be selected from the group of passively binding structures consisting of allergens, peptidic allergens, recombinant allergens, allergen-idotypical antibodies, autoimmune-provoking structures, tissue rejection-inducing structures, immunoglobulin constant regions and their derivatives, mutants or combination thereof. A targeting moiety with higher valency may be generated by combining at least two identical or different binding structures selected from the above mentioned groups.

As used herein the term "antibody" refers to polyclonal antibodies, monoclonal antibodies, humanized antibodies, single-chain antibodies, and fragments thereof such as Fab, F(ab')2, Fv, and other fragments which retain binding function and specificity of the parent antibody. As used herein the term "monoclonal antibody" refers to an antibody composition having a homogeneous antibody population. The term is not limited regarding the species or source of the antibody, nor is it intended to be limited by the manner in which it is made. The term encompasses whole immunoglobulins as well as fragments such as Fab, F(ab')2, Fv and others which retain binding function and specificity of the antibody. Monoclonal antibodies of any mammalian species can be used in this invention. In practice, however, the antibodies will typically be of rat or murine cell lines for use in making the required hybrid cell lines or hybridomas to produce monoclonal antibodies.

In a preferred embodiment of the invention, the antibodies are human antibodies. As used herein, the term "human antibodies" means that the framework regions of an immunoglobulin are derived from human immunoglobulin sequences. As used herein the term "single chain antibody fragment" (scFv) refers to antibodies prepared by determining the binding domains (both heavy and light chains) of a binding antibody, and supplying a linking moiety, which permits preservation of the binding function. This forms, in essence, a radically truncated antibody, having only that part of the variable domain necessary for binding to the antigen. Determination and construction of single chain antibodies are described in U.S. Pat. No. 4,946,778 to Ladner et al.

As used herein the term "aptamer" refers to a nucleic acid molecule which specifically binds to structures on the cell surface of a target cell preferably the aptamer binds to cell surface receptors which are internalized after binding and thus mediate the cell type specific uptake of the complex of present invention. The aptamer can consist of DNA, RNA or chemically modified DNA or RNA. Aptamers can be obtained by a process called selective evolution of ligands by exponential enrichment (SELEX). Starting from a diverse pool of nucleotide sequences, molecules with a high affinity to their targets are isolated by iterative rounds of selection and amplification.

The "nucleic acid moiety" of the compound of present invention represents the nucleic acid, which is active in the cytosol of the cell after cellular entry of the compound. These nucleic acid moieties of the present invention can be selected from any class of nucleic acid molecules which sequence specifically block protein synthesis of a selected target protein. Preferably the nucleic acid moiety is chosen out of two main classes of nucleic acid molecules: 1. antisense oligonucleotides (ODNs) 2. short interfering RNAs (siRNAs). If the nucleic acid moiety is chosen to be an antisense oligonucleotide it can consist of single stranded DNA or RNA which can be chemically modified at its sugar phosphate backbone or at the nucleobases. Modifications can be the exchange of a non-bridging oxygen atom in the phosphodiester backbone to a sulphur atom to create a phosphothioate linkage. The antisense oligonucleotide anneals to complementary regions on the mRNA of a target protein and blocks translation by ether RNase H mediated cleavage of RNA/DNA duplexes or by steric hindrance. Preferably, the antisense oligonucleotides comprise 10 to 40, more preferably 15-30 or 17 to 25 bases. Furthermore, the nucleic acid moiety can also consist of peptide nucleic acids, a class of antisense molecules in which the sugar phosphate backbone is replaced by an N-(2-aminoethyl)-glycine backbone. If the nucleic acid moiety is chosen out of the class of siRNAs it can consists of double stranded RNA or chemically modified double stranded RNA. Chemical modifications can be inserted into the sugar phosphate backbone in order to increase the nuclease stability. Modifications can be the exchange of a non bridging oxygen atom of the phosphodiester bond to a sulphur atom to create a phoshphothioate linkage. The 2'-hydroxyl group of the ribose unit can be exchanged to a 2'-fluorine atom, or a 2'-methoxy group, or a 2'-ethoxy group or a 2' methoxyethyl group. RNA can also contain so called locked nucleic acids which contains 2'-O,4'-C-methylene-α-D-ribofuranosyl nucleotides.

Nucleotides with these modifications can be inserted at any position in both strands of the RNA sequence. Preferably, the double stranded RNA has a length between 17 and 40 nucleotides.

As used herein the term "covalent link" refers to a chemical conjugation, which is obtained in a chemical reaction between a reactive group comprised by the targeting moiety and a reactive group comprised by the nucleic acid moiety after which both moieties are linked via a covalent bond.

The covalent linkage can be achieved with a disulphide bond, an amine bond, an amide bond, a phosphodiester bond, a phosphothioate bond, an ether bond, a thioether bond, a carbon carbon bond, an ester bond, hydrazone linkage, a carbazide linkage or a carbamate linkage.

The nucleic acid moiety can comprise a reactive group at the 3' or 5' end of any of the two strands. It can comprise any reactive group which can be inserted into the DNA or RNA strand by standard or non standard solid phase synthesis techniques.

If the targeting moiety is a protein it comprises amino groups, sulfhydryl groups, hydroxyl groups, carboxyl groups or sugar moieties which can be used for coupling or for modification with a linker molecule. If the targeting moiety is a recombinantly expressed protein reactive groups different from the above mentioned can be inserted by inserting artificial amino acids into the primary amino acid sequence. This will lead to site directed conjugation of the nucleic acid moiety to the targeting moiety.

A linker molecule as used herein refers to a synthetic molecule which reacts with the targeting moiety or the nucleic acid moiety in order to introduce special reactive groups which can be used for covalent coupling of both moieties.

The targeting moiety, the nucleic acid moiety or both can be modified with a linker molecule in a separate reaction prior to the cross-linking procedure. The choice of linker molecule to modify the targeting moiety or the nucleic acid moiety depends on the coupling strategy used.

Conjugation via the formation of an amide bond can be mediated by activation of a carboxyl group and subsequent reaction with a primary amine. Activating agents can be various carbodiimides like: EDC (1-Ethyl-3-(3-dimethylaminopropyl) carbodiimide hydrochloride), EDAC (1-ethyl-3(3-dimethylaminopropyl)carbodiimide hydrochloride), DCC (dicyclohexyl carbodiimide), CMC (1-Cyclohexyl-3-(2-morpholinoethyl)carbodiimide), DIC (diisopropyl carbodiimide) or Woodward's reagent K (N-ethyl-3-phenylisoxazolium-3'-sulfonate).

Reaction of an activated NHS-Ester with a primary amine also results in formation of an amide bond.

Conjugation via the formation of a secondary amine can be achieved by reaction of an amine with an aldehyde group followed by reduction with a H⁻ donor like sodium cyanoborohydride.

Aldehydes can be introduced for instance by oxidation of sugar moieties or by reaction with SFB (succinimidyl-p-formyl benzoate) or SFPA (succinimidyl-p-formylphenoxyacetate).

Conjugation via the formation of disulphide bonds can be accomplished by pyridyldisulfide mediated thiol-disulfide exchange. Introduction of sulphydryl groups is mediated for instance by Traut's Reagent (2-Iminothiolane) SATA (N-succinimidyl S-acetylthioacetate, SATP (succinimidyl acetylthiopropionate), SPDP (N-succinimidyl 3-(2-pyridyldithio)propionate, SMPT (succinimidyloxycarbonyl-α-methyl-α-(2-pyridyldithio)toluene), N-acetylhomocysteinethiolactone, SAMSA (S-acetylmercaptosuccinic Anhydride), AMBH (2-Acedamido-4-mercaptobuturic acid hydrazide), cystamine (2,2'-dithiobis(ethylamine).

Conjugation via the formation of thioether linkages can be performed by the specific reaction of a sulfhydryl containing component with maleimide- or iodoacetyl groups containing molecules or by the reaction of an epoxide activated targeting or nucleic acid moiety. Maleiimide groups can be introduced into the targeting or nucleic acid moiety by SMCC (succinimidyl-4-(N-maleimidomethyl)cyclohexane-1-carboxylate), sulfo-SMCC (sulfosucci-nimidyl 4-(N-maleidomethyl)-cyclohexane-1-carboxylate), MBS (m-Maleimidobenzoyl-N-hydroxysuccinimide ester), sulfo-MBS (m-Maleimidobenzoyl-N-sulfohydroxy succinimide ester), SMPB (Succinimidyl-4-(p-maleidophenyl)butyrate), sulfo-SMPB (sulfosuccinimidyl 4-(p-maleimidophenyl)butyrate), GMBS (N-α-maleimidobuturyl-oxysuccinimide ester), sulfo GMBS (N-α-maleimidobuturyl-oxysulfosuccinimide ester).

Iodoacetyl groups can be inserted with SIAB (N-succinimidyl(4-iodoacetyl)aminobenzonate, sulfo SIAB (sulfosuccinimidyl(4-iodoacetyl)-aminobenzonate), SIAX (succinimidyl6-[(iodoacetyl-amino]hexanoate), SIAXX (succinimidyl6-[6-(((iodoacetyl)amino)-hexanoyl]amino] hexanoate), SIAC (succinimidyl 4-(((iodoacetyl)amino)methyl)-cyclohexane-1-carboxylate), SIACX (succinimidyl 6-((((4-(iodoacetyl)amino)methyl)-cyclohexane-1-carbonyl)amino) hexanoate), NPIA (p-nitrophenyl iodoacetate).

Conjugation via the formation of a carbamate linkage can be performed by reaction of a hydroxyl residue of the targeting or nucleic acid moiety with CDI (N,N'-carbonyldiimidazole) or DSC(N,N'-disuccinimidyl carbonate) or N-hydroxysuccinimidylchloroformate and subsequent reaction with an amine present in the targeting or nucleic acid moiety.

Cross-linking of the targeting and nucleic acid moiety can also be achieved by introduction of a photoreactive group into one moiety. Photoreactive groups are aryl azides, halogenated aryl azides, benzophenones certain diazo compounds and diazirine derivatives. They react with amino groups or activated hydrogen bonds.

Conjugation via ether linkages can be mediated by reaction of an epoxide containing molecule with a hydroxyl group of the targeting moiety or the nucleic acid moiety.

If the targeting moiety is a mono-, bi- or multivalent aptamer, both strands of the RNA are covalently linked via a hairpin loop at the 3' End of the sense strand. If the targeting moiety is an aptamer the nucleic acid moiety is connected via a phosphodiester or phosphothioate bond.

The sequence of chosen gene silencing nucleic acid is determined by the mRNA sequence of the target protein. In principal the gene silencing nucleic acid can be directed against any protein expressed in a cell. Objective of this invention are gene silencing nucleic acids targeting mRNA sequences of proteins which are essential for cell viability. Knock down of these proteins will result in apoptosis. In combination with the cell binding moiety it will become possible to selectively induce apoptosis in certain cells of a multicellular organism.

Apoptosis can be induced by the knock down of genes which code for important factors of the translation machinery e.g. human elongation factor 2, ribosomal RNAs which fulfill important catalytic functions in the ribosome or tRNAs. The reduced level of protein synthesis results in triggering the apoptotic pathway and therefore leads to cell death.

A second approach for the induction of apoptosis in a target cell is the knock down of proteins which down regulate or inhibit the apoptotic pathway, so called anti-apoptotic proteins. These proteins can either be part of the intrinsic pathway which propagates through the release of cytochrome c of the mitochondria and subsequent activation of proteases of the caspase family or the extrinsic pathway. The extrinsic pathway is triggered by extra cellular death signals and propagates via the direct activation of various caspases without the involvement of the mitochondrial enzymes. Potential targets of the intrinsic pathway are proteins which belong to the Bcl2 family like Bcl2, Bcl-XL, Bcl-W, Mcl-1, A1, Ced9, E1B19K or BHRF1. Some Bcl-2 binding proteins also comprise anti-apoptotic effects by enhancing the effect of Bcl-2 like Bag-1, Raf-1, Calcineurin, Smn, Beclin, ANT and VDAC. The extrinsic pathway is negatively regulated by members of the Inhibitor of Apoptosis (IAP) protein family like IAP-1, IAP-2, Survivin, and x-IAP. These proteins inhibit TNFα and CD-95 mediated apoptosis and are also inhibitors of caspase activation. Apoptosis could also be induced by the knock down of proteins which disturb NF-κB signaling which are IKK-α, IκB, or NF-κB itself. The FLIP protein serves as an apoptosis inhibitor by preventing the release of caspase 8 during CD95 triggered death signaling.

Furthermore apoptosis can also be induced by the inhibition of proto-oncogenes like Akt, or Akt-activating proteins like are PI3K or PDK1.

Preferably, the compound of the invention is soluble. The term "soluble" refers to the ability of the complex to stay in solution when recombinantly expressed in particular during protein purification and coupling procedures applied when coupling the gene silencing nucleic acid to the protein of interest. The term also refers to the state of the complex inside a cell upon release from any kind of incorporation vesicle.

The term synthetic refers to a man made complex not found in nature. The term also comprises the meaning of recombinant.

EXAMPLES

In the first approach, chemically modified siRNA is covalently coupled to a tumour cell specific antibody in order to obtain a compound (Immuno-RNA-construct) of the invention.

The second approach is to achieve cell specificity using RNA aptamers as targeting moiety. The siRNA portion is genetically fused to the aptamer via a short linker sequence. In addition bivalent Aptamer siRNA conjugates will be used in which two specifically binding aptamer moieties are present.

The presence of two antigen binding sites as well as the presence of more than one siRNA moiety will potentially increase the affinity as well as the biological activity of the resulting constructs.

After binding of the targeting moiety to the target receptor, the construct is internalised and the siRNA translocated to the cytosol of the target cell, where it induces sequence specific mRNA degradation. The siRNA is targeted against human elongation factor 2 as a crucial component of translation. The "Knock down" of elongation factor 2 blocks protein synthesis which in turn leads to apoptosis of the cell.

Materials and Methods
Sequences:
The following sequences were used:

```
SEQ ID NO 1: xPSM-A-3-siGFP:
GGGAGGACGAUGCGGAUCAGCCAUGUUUACGUCACUCCUUGUCAAUCCUC
AUCGGCGCAAGCUGACCCUGAAGUUCAUGAAGCUUGGAACUUCAGGGUCA
GCUUGCCG

SEQ ID NO 2: xPSM-A-3-siEEF2
GGGAGGACGAUGCGGAUCAGCCAUGUUUACGUCACUCCUUGUCAAUCCUC
AUCGGCAGCGCCAUCAUGGACAAGAAUUGAAGCUUCUUCUUGUCCAUGAU
GGCGCGG siEEF2 Sequence 1
                                             (SEQ ID NO: 3)
sense:     r(AGG CCU AUC UGC CCG UCA A)dTdT
                                             (SEQ ID NO: 4)
antisense: r(UUG ACG GGC AGA UAG GCC U)dTdG siEEF2 Sequence 2
                                             (SEQ ID NO: 5)
sense:     r(GCG CCA UCA UGG ACA AGA A)dTdT
                                             (SEQ ID NO: 6)
antisense: r(UUC UUG UCC AUG AUG GCG C)dGdG SEQ ID NO 7: A30 siGFP
GGGAAUUCCGCGUGUGCCAGCGAAAGUUGCGUAUGGGUCACAUCGCAGGC
ACAUGUCAUCUGGGCGGUCCGUUCGGGAUCCUCGGAAGCUUGCAAGCUGA
CCCUGAAGUUCAUGAAGCUUGGAACUUCAGGGUCAGCUUGCCG SEQ ID NO 8: A30 siEEF2
GGGAAUUCCGCGUGUGCCAGCGAAAGUUGCGUAUGGGUCACAUCGCAGGC
ACAUGUCAUCUGGGCGGUCCGUUCGGGAUCCUCGAAGCUAGCGCCAUCAU
GGACAAGAAUU GAAGCUUCUUCUUGUCCAUGAUGGCGCGG SEQ ID NO 7: siGFP
                                             (SEQ ID NO: 9)
sense:     5'-GCAAGCUGACCCUGAAGTTCAT
                                             (SEQ ID NO: 10)
antisense: 5'-GAACTTCAGGGTCAGCTTGCCG
```

-continued
```
SEQ ID NO 11: PSMB1-siEEF2
GGGAGGACGAUGCGGAUCAGCCAUGUUUACGUCACUCCUUGUCAAUCCUC
AUCGGCUAAAAAUUGCGCCAUCAUGGACAAGAAUUAAUUAAGGGAGGACG
AUGCGGAUCAGCCAUGUUUACGUCACUCCUUGUCAAUCCUCAUCGGCAAA
AAUUCUUGUCCAUGAUGGCGCGGGAGCTCGAATT SEQ ID NO 12: PSMB2-siEEF2
GGGAGGACGAUGCGGAUCAGCCAUGUUUACGUCACUCCUUGUCAAUCCUC
AUCGGCUAAAAAUUAGGCCUAUCUGCCCGUCAAUUAAAAAUUGGGAGGACG
AUGCGGAUCAGCCAUGUUUACGUCACUCCUUGUCAAUCCUCAUCGGCAGC
GCCAUCAUGGACAAGAAUUGAAGCUUCUUCUUGUCCAUGAUGGCGCGGAA
AAAAAUUGACGGGCAGAUAGGCCUUU GAGCTCGAATT SEQ ID NO 13: PSMA biv anneal siEEF2-1
GGGAGGACGAUGCGGAUCAGCCAUGUUUACGUCACUCCUUGUCAAUCCUC
AUCGGCUAAAAAUUGCGCCAUCAUGGACAAGAAUU SEQ ID NO 14: PSMA biv anneal siEEF2-2
GGGAGGACGATGCGGATCAGCCATGTTTACGTCACTCCTTGTCAATCCTC
ATCGGCAAAAATTCTTGTCCATGATGGCGCGG
```

Antibodies, Aptamers and Small Interfering RNAs

The full length antibody Ki-4 specifically binds to the CD30 receptor presented on the surface of L540 cells. The aptamers A30 and xPSM-A-3 show a specific binding to the antigens Her3 presented on MCF-7 cells and PSMA (Prostate Specific Membrane Antigen) presented on LNCaP cells.

For the siRNA experiments three different sequences were used: siRNA against EGFP (SEQ ID NOS 9-10), two different siRNA sequences against EEF2 (SEQ ID NOS: 3-6).

For the conjugation of the antibody to the siRNA, siRNA's were modified to protect them from RNAse digestion (SEQ ID NOS: 3-6). The synthesis of the modified siRNAs was performed by Dharmacon (Chicago, USA).

For the genetic fusion (Assembly PCR) of the aptamer to the shRNA sequence, DNA primers were designed and synthesized by MWG-Biotech (Ebersberg, Germany).

E. coli XL1-blue (supE44 hsdR17 recA1 endA1 gyr A46 thi relA1 lacF'[pro AB+lacIq lacZ ΔM15 Tn10(tetr)]) were used for the propagation of plasmids. The eukaryotic expression vector psecTag2B-GFP are derived from the psecTag plasmid (Invitrogen, Carlsberg, USA) and from the pmaxGFP plasmid (Amaxa, Köln, Germany). The GFP-encoding sequence of the pmaxGFP plasmid was cut out in the XhoI/NheI-kinase domains and pasted in the same domains into the psecTag plasmid. Plasmids were prepared by the alkaline lysis method and purified using plasmid preparation kits from Qiagen, Hilden, Germany. Restriction fragments were separated by horizontal agarose gel electrophoresis and extracted with QIAquick (Qiagen). All standard cloning procedures were carried out as described by Sambrook, J. et al., 1989.

Cell Culture

All cell lines, including the CD30-positive cell lines L540Cy (Kapp, U. et al., 1992) and the CD30-negative cell lines MCF-7 (ATCC, VA, USA), LNCaP (DSMZ, Germany) and 293T (ATCC) were cultivated in complex medium (RPMI 1640) supplemented with 10% (v/v) heat-inactivated fetal calf serum, 50 µg/ml penicillin, 100 µg/ml streptomycin and 2 mM L-glutamine. All cells were cultured at 37° C. in a 5% $CO_2$ in air atmosphere. The cell lines L540, MCF-7 and LNCaP were also used in a transfected form containing the vector psecTag2B-GFP which expressed very strongly the protein GFP. For the selection of transfected cells, Zeocin (Invitrogen, Carlsbad, USA) was added to a final concentration of 100 µg/ml.

Construction and Synthesis of the Immuno-RNA-Constructs
Cloning and Expression of psecTag2B-GFP For the construction of a vector, the GFP-encoding sequence was cut out by the restriction sites XhoI/NheI. After XhoI/NheI-digestion, the restricted fragment was cloned into the eukaryotic expression vector psecTag2B respectively, digested with the same restriction enzymes. The resulting recombinant construct psecTag2B-GFP encoding GFP was verified by sequence analysis. After nucleofection (Amaxa) transformation into L540, MCF-7 and LNCaP cells, the GFP was strongly expressed. Briefly, 2 µg plasmid-DNA and 100 µl nucleofection solution were used according to the manufactures protocol for 6 well cell culture plates.

Transfection efficiency was determined to be between 33-90% by counting green fluorescent cells. Subsequently, transfected cells were transferred into medium-sized cell culture flasks (Nunc; 85 m$^2$) and grown in RPMI complex medium supplemented with 100 µg/ml Zeocin. One to two weeks productively transfected clones were green fluorescing. Transfected cell populations were established by subcultivation of these clones.

Conjugation of the full length antibody Ki4 to the siRNA against GFP (SEQ ID NOS: 3-4) and to the siRNA against EEF2 (SEQ ID NOS: 5-6)

For the coupling of the antibody to one of the siRNA sequences the RNA is covalently linked to the protein. The antibody is activated by Trauts-reagent (2-Iminothiolane) in order to introduce free thiol groups into the protein. Excess of Trauts reagent was removed by desalting using nanosep 10k spin columns (Pall biosciences). The activation of the siRNA is done by reaction with SPDP (N-succinidyl 3-(2-pyridyldithio)propionate). Unreacted SPDP is removed by gel filtration using centrispin 10k spin columns (EMP biotech, Berlin). For the crosslinking reaction the activated siRNA is added to the thiolated antibody in a 10-fold molar excess. Crosslinking was performed over night at room temperature. To remove the unconjugated siRNA the solution was spun through a nanosep 100k-Spin-column (Pall biosciences, East Hills N.Y., USA). Before application of the constructs in in vitro toxicity assays all samples were sterile filtrated.

Genetic fusion of the aptamers A30 and xPSM-A-3 to the siRNA against GFP (SEQ ID NO 7 and 1) and to the siRNA against EEF2 (SEQ ID NO 8 and 2)

To synthesize the aptamer-spacer-siRNA-construct, specific DNA primers were designed by a web based design algorithm called assembly PCR oligo maker and synthesized by MWG-Biotech. After the initial assembly PCR using all four primers the full length DNA is amplified using two flanking primers. finally the RNA sequence was produced by in vitro transcription. The reaction was purified over a 8%-Urea-PAGE-Gel RNA bands were visualized by UV shadowing and excised. Afterwards the RNA was extracted from the gel slices.

As the correct folding of the aptamer is important for its binding, the constructs were heated 3 min by 95° C. and finally incubated 30 min by 37° C. The yield of one transcription reaction was calculated, after the concentration was determined by UV absorbance at 260 nm.

Genetic fusion of the bivalent Aptamer constructs PSMB1-siEEF2, PSMB2-siEEF2 and PSMA biv1 anneal 1 and PSMA biv anneal 2 (SEQ ID NO 11, 12 and 13 and 14).

The DNA sequences of PSMB1 and PSMB2 were synthesized by GENEART AG (Regensburg) and cloned into the pUC19 vector using 5' KpnI 3' SacI restriction sites. The RNA sequences are obtained by run off in vitro transcription from EcoRI digested plasmid DNA as template using Durascribe T7 transcription kit. The RNA is purified as described above resulting in a RNA sequence in which two aptamer functionalities separated by spacer sequences are fused to the siRNA sequence against EEF2.

Both DNA templates of PSMA biv anneal 1 and 2 are also produced via assembly PCR using complementary annealing oligos. In vitro transcription is performed using the Durascribe T7 transcription kit. After purification of both RNA fragments they are fused together in an annealing reaction in which the complementary 3' overhangs anneal and thus form a bivalent annealed aptamer. For the annealing both monomers are pooled in equimolar ratio and heated to 95° C. for 3 min and then slowly cooled to 37° C.

Flow Cytometry Analysis

Cell binding activity of the Immuno-RNA-constructs was evaluated using a FACSCalibur flow cytometry instrument and CellQuest software (Becton Dickinson, Heidelberg, Germany). Cells were stained with the FITC-labeled constructs as described in the results (25). Briefly, ten thousand events were collected for each sample and analysis of intact cells was performed using appropriate scatter gates to exclude cellular debris and aggregates. 2-5×10$^5$ cells were incubated for 30 min on ice with 10 µl of protein-RNA-constructs or RNA-RNA-constructs at a concentration of 10-100 nM. The cells were washed twice with 1×PBS buffer containing 0.2% w/v BSA and 0.05% w/v sodium azide (PBA). After a final wash, the cells were analyzed on a FACScalibur (Becton Dickison, Heidelberg, Germany).

Affinity Analysis Via Flow Cytometry

Binding affinities of produced constructs were determined using a flow cytometry based equilibrium binding assay. Increasing concentrations of Fluoresceine labeled Aptamer constructs were applied to a constant amount of cells. For flow cytometric analysis cells were incubated on ice in the dark for 20 min. Cells were washed twice with 1×PBS and resuspended in 500 µL 1×PBS for FACS analysis. Ten thousand events were collected and analysed using appropriate scatter gates to exclude aggregates and cell debris. Binding curves were generated by plotting of mean fluorescence shift in Fl1 direction against the logarithmic Aptamer concentration.

Colorimetric Cell Proliferation Assays

First apoptotic analysis were performed with the Annexin V Apoptosis Kit from BD Biosciences (Franklin Lakes, USA) where slight effects of specific siRNAs could be documented (data not shown). The apoptotic pathway is characterized by certain morphologic features, including loss of plasma membrane asymmetry and attachment, condensation of the cytoplasm and nucleus, and internucleosomal cleavage of DNA. Annexin V-FITC is a sensitive probe for identifying apoptotic cells. It binds to negatively charged phospholipid surfaces with a higher specificity for phosphatidylserine (PS) than most other phospholipids. Defined calcium and salt concentrations are required for Annexin V-FITC binding as described in the Annexin V-FITC Staining Protocol. Purified recombinant Annexin V was conjugated to FITC under optimum conditions. Annexin V-FITC is routinely tested using primary cells or cell lines induced to undergo apoptotic cell-death. A defined concentration of Immuno-RNA-constructs was applied onto 2-4×10$^4$ target cells in 600 µl aliquots of complete medium and the plates were incubated for 48 h at 37° C. Afterwards the analysis was performed following the manufacturer's instructions.

The cytotoxic effect of the Immuno-RNA-constructs on target cells was determined by measurement of metabolization of yellow tetrazolium salt (XTT) to a water soluble orange formazan dye as published by Barth, S. et al. 2000. To 2-4×10$^4$ Target cells in 100 µL complete medium in 96-well plates various dilutions of Protein-RNA constructs and RNA-RNA constructs were added in 100 µL complete medium so that the final assay volume was 200 µL. Subsequently plates were incubated for 48 h at 37° C. Afterwards, the cell cultures were pulsed with 100 µl fresh culture medium supplemented with XTT/PMS (final concentrations of 0.3 mg/mL and 0.383 ng respectively) for 24 h. The spectrophotometrical absorbance of the samples was measured at 450 and 650 nm (reference wavelength) with an ELISA reader (MWG Biotech). The concentration required to achieve a 50% reduction of protein synthesis (IC$_{50}$) relative to untreated control cells was determined. All measurements were done in triplicates.

The effects of the Immuno-RNA-constructs were also confirmed by the OPERA System (Evotec technologies). OPERA is a new confocal microplate imaging reader providing solutions for fully automated high speed and high resolution screening. Key for high resolution is strictly confocal imaging and the use of water immersion lenses. The bodywork of the experiment was the same as the one of the XTT-viability-assay as described above. 2-4×10$^4$ target cells were distributed in 100 μl-aliquots in 96-well plates. 100 μl aliquots of Ki-4 RNA construct in complete medium were added and the plates were incubated for 96 h at 37° C. After the application of the Immuno-RNA-construct Ki-4-siRNA onto the target cells, the cells were analyzed concerning the changes in the cell morphology and the silencing effects of the coupled siRNA (in this case: siRNA against EEF2 and GFP). For the final measurement the cells were incubated with DRUG 5 (used according to the manufactures protocol) to visualize the proliferation of the cells. All measurements were done in triplicates.

Results:
Evaluation of the Toxicity of RNAi Against Eucaryotic Elongationfactor 2
Evaluation of the Nucleic Acid Moiety (siRNA)
Knock Down of Green Fluorescent Protein (EGFP)

To establish a reference system for general evaluation of silencing activities of siRNAs, different concentrations of siEGFP were transfected into 293T cells transformed with eGFP (293-LGFP-KMH). After 48 h the cells were analyzed by flow cytometry and a knock down of the eGFP-signal to about 60% was detected.

Knock Down of Eucaryotic Elongation Factor 2 (EEF2)

Corresponding to the above mentioned results, the same concentrations of siRNA against EEF2 were used to transfect 293T, MCF-7, LNCaP and L540 cells. "RNAifect"® supplied by Qiagen®, a special lipofection solution for siRNA transfections, was used for all transfection experiments.

Since knock down of elongation factor 2 should inhibit protein synthesis and should lead to cell death the efficacy of the siRNA was evaluated via an in vitro cytotoxicity test (XTT-Viability-Assay). The viability of the cells was analyzed 48 h after transfection of the siRNA in an ELISA-Reader by measuring absorption at 450 nm (L1) and 650 nm (L2) (reduction L1-L2). All experiments were performed in triplicates.

Calculated median inhibitory concentrations at 50% cell viability (IC$_{50}$) of between 0.9 and 1.1 μg/ml were observed in all four target cell lines (FIGS. 1-4).

The Design of the Immuno RNA Constructs
Protein-siRNA-Construct

The full-length antibody Ki-4 targeting CD30 on lymphoma cells was covalently coupled to the siRNA against EGFP or eucaryotic elongation factor 2 (EEF2).

RNA was conjugated to the antibody by forming a disulphide bridge: prior to the conjugation reaction the synthetic siRNA which contained a reactive amino group at its 3' terminus was modified with a heterobifunctional linker SPDP (N-succimidyl 3-(2-pyridyldithio)propionate). Free sulfhydryl groups were inserted into the antibody by reaction with Trauts reagent (2-Iminotholane). Covalent conjugation was finally achieved by pyridyldisufide exchange reaction by simply mixing both activated moieties.

Full RNA-Construct

After evaluation of the siRNA against EEF2, it was genetically fused to the aptamer moieties (A30 targeting HER3 and xPSM-A-3 targeting PSMA) by assembly PCR using a short linker sequence. Sense and anti-sense strand of the siRNA part were linked with a short hairpin loop in order to allow synthesis of the aptamer shRNA construct from one single DNA strand.

Figure 5A:
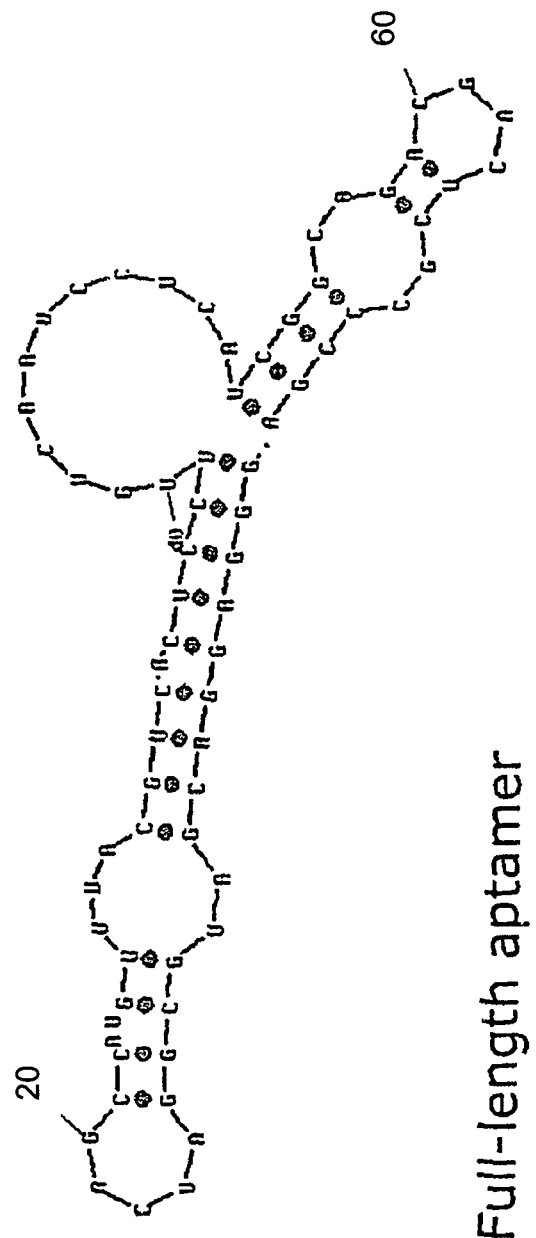
FIG. 5A depicts a full-length aptamer as in SEQ ID NO:15.
Figure 5B:
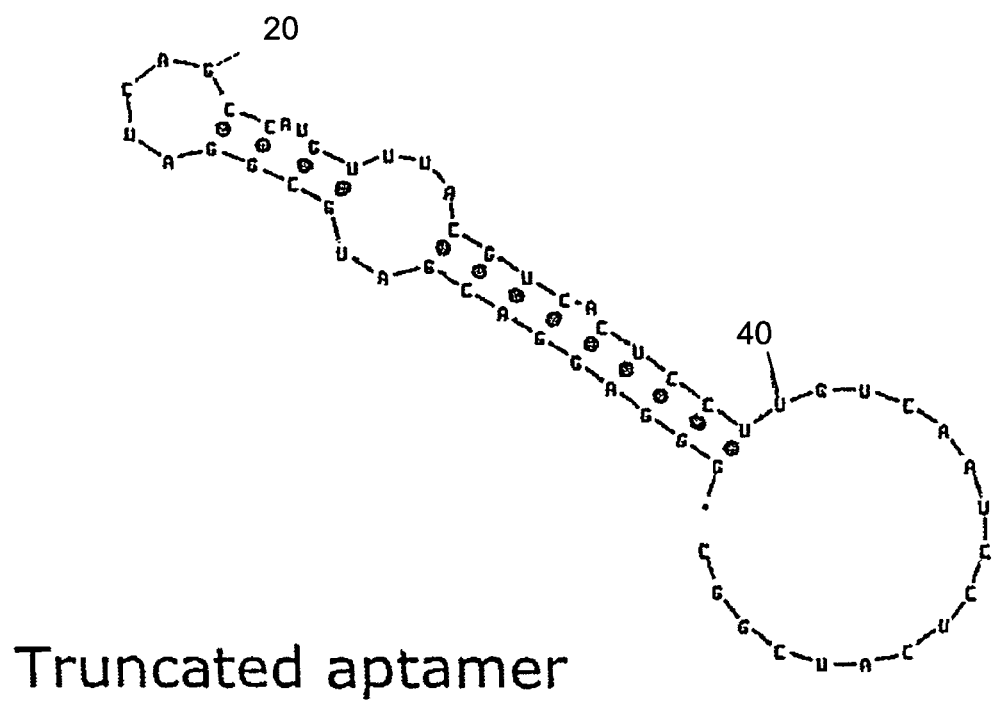
FIG. 5B depicts a truncated aptamer as in SEQ ID NO:16.
Figure 6A:
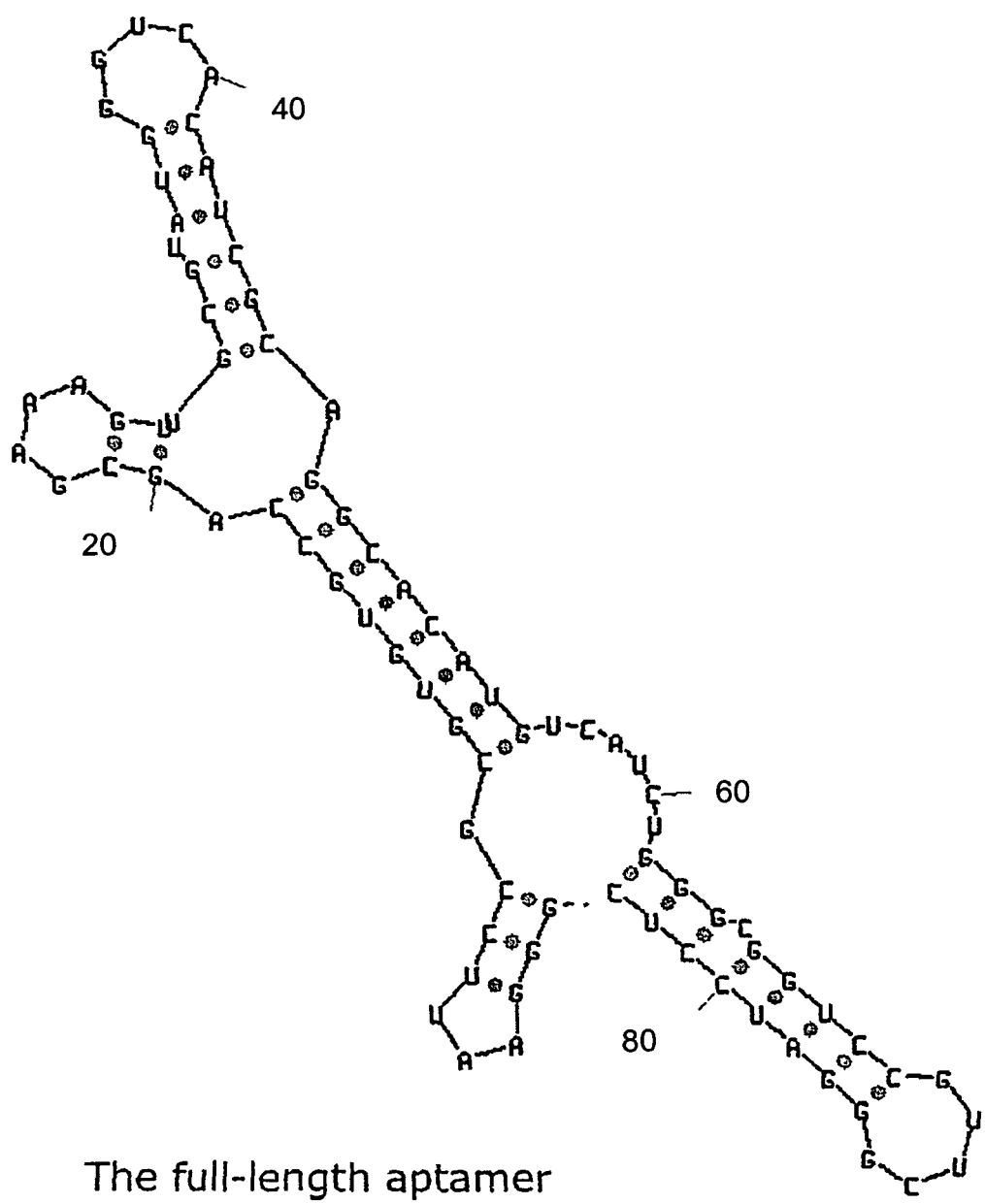
FIG. 6A depicts a full-length aptamer as in SEQ ID NO:17.
Figure 6B:
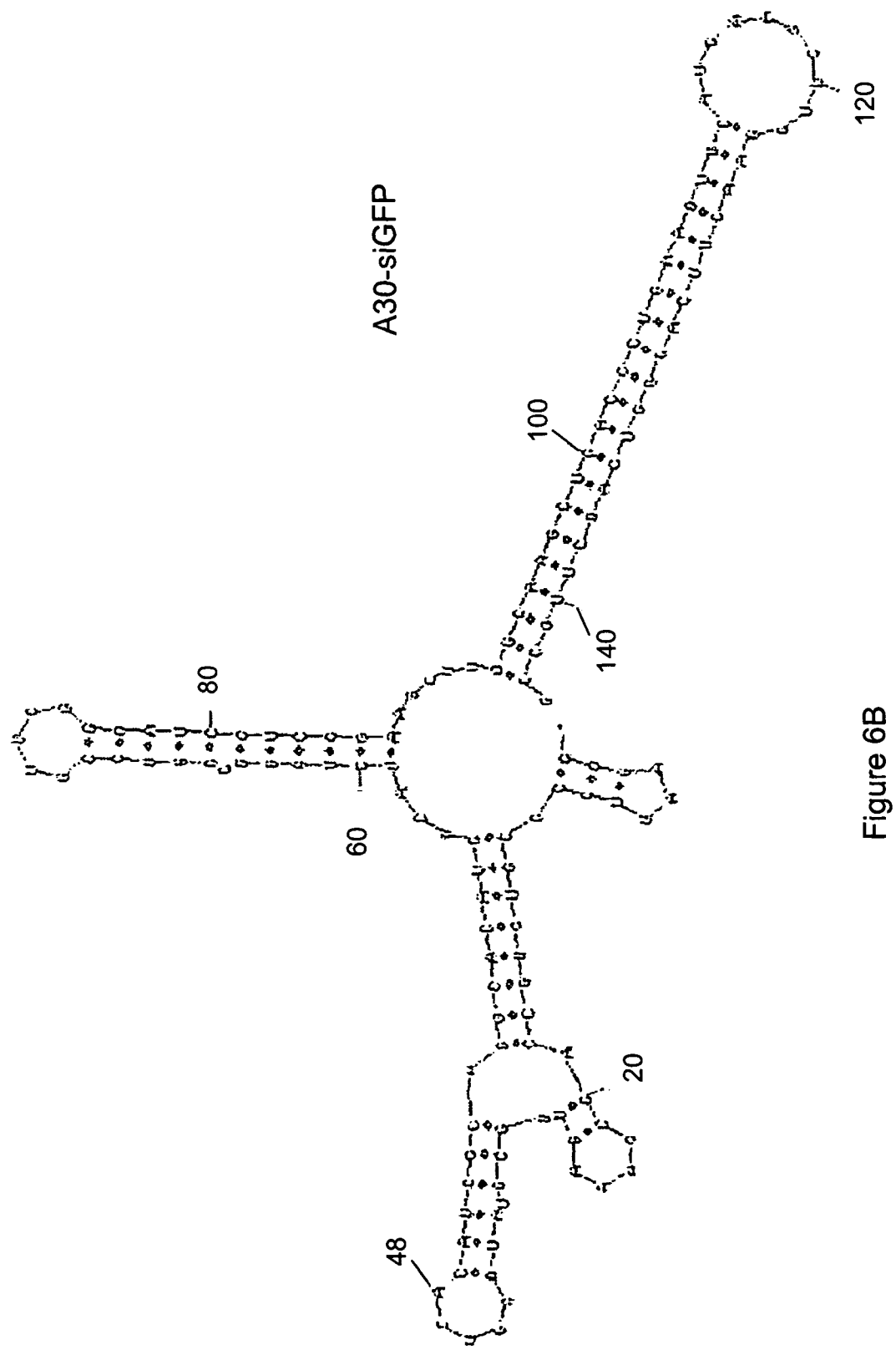
FIG. 6B depicts an A30-siGFP immuno-RNA-construct, as in SEQ ID NO:7.

The most important point of the design of the construct was to ensure the correct folding of the aptamer region as a prerequisite for binding and of the siRNA as a prerequisite for induction of specific mRNA degradation. The final construct consisted of an aptamer region which independently folded into its native conformation without being affected by the shRNA portion. This could be achieved by inserting a short linker sequence at the 3' end of the aptamer sequence (FIGS. 5 and 6).

After successful PCR assembly the DNA sequence was verified by DNA sequence analysis.

To obtain the corresponding RNA sequences, in vitro transcription was performed and the products subsequently purified by gelelectrophoris (8%-Urea-PAGE-Gel). The yield of one in vitro transcription in general was in a range of about 15 μg RNA. As correct folding of the aptamer is essential for its binding activity, the RNA was heated for 5 min to 95° C. and finally incubated at 37° C. for 15 min prior to all experiments to allow formation of the correct tertiary structures.

Bivalent Aptamer siRNA Constructs

Figure 7A:
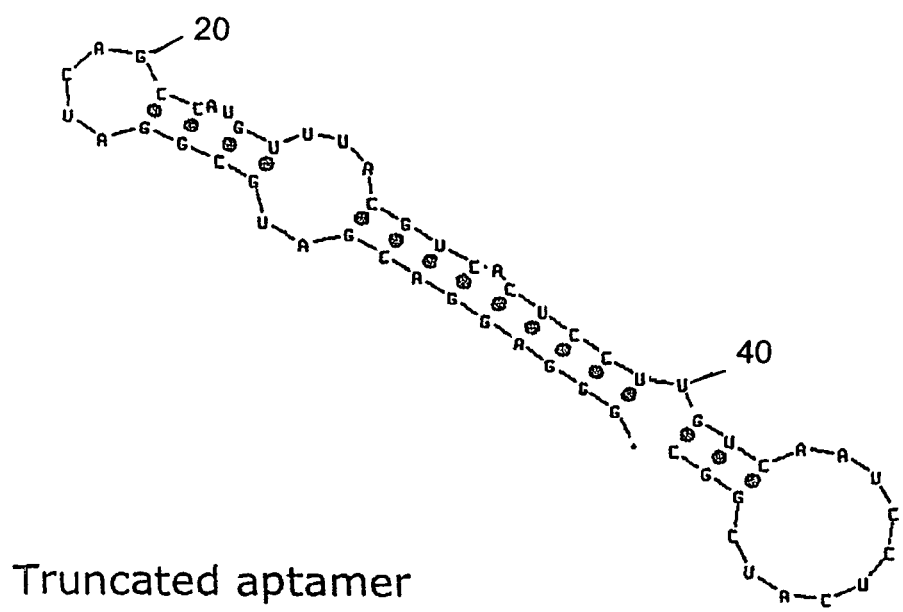
FIG. 7A depicts a truncated aptamer as in SEQ ID NO:18.
Figure 7B:
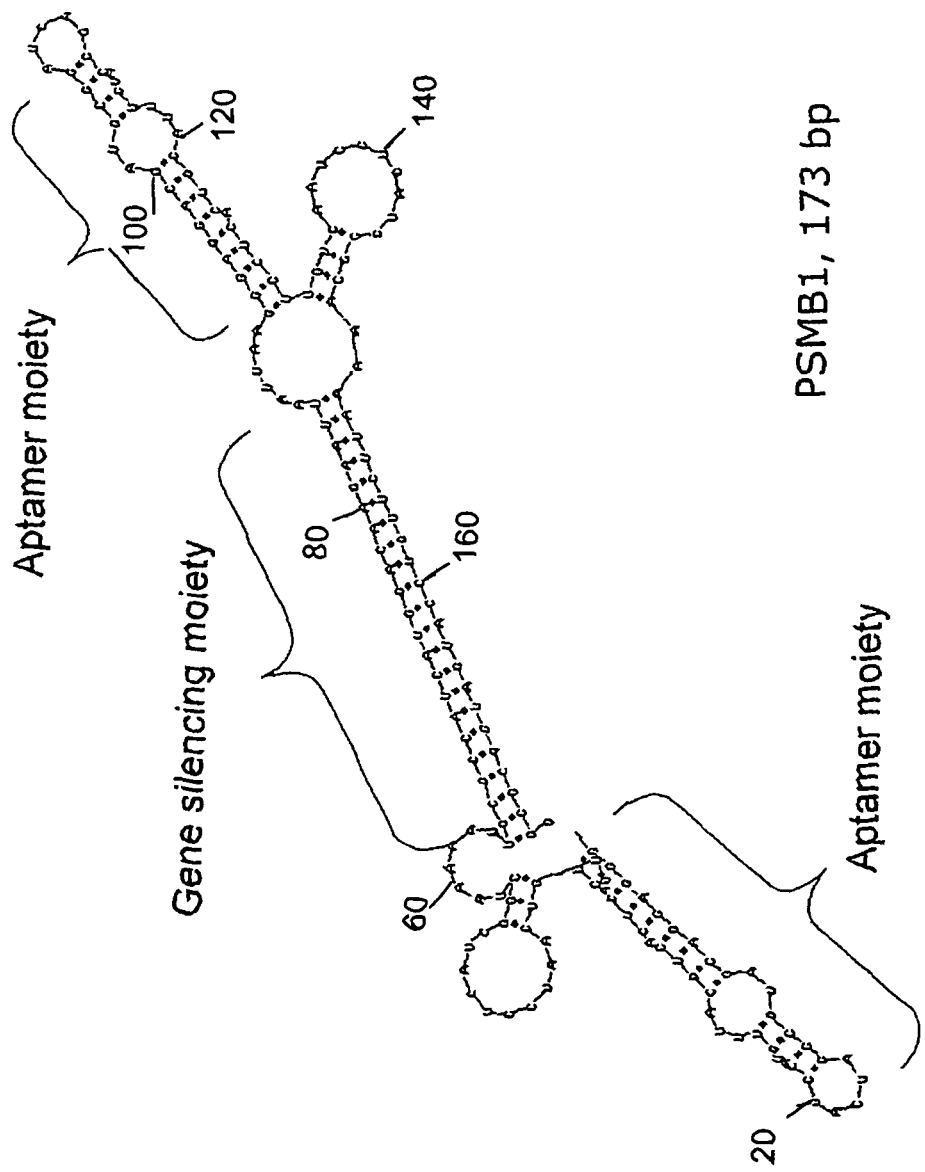
FIG. 7B depicts a bivalent aptamer siRNA construct as in SEQ ID NO:19.
Figure 8A:
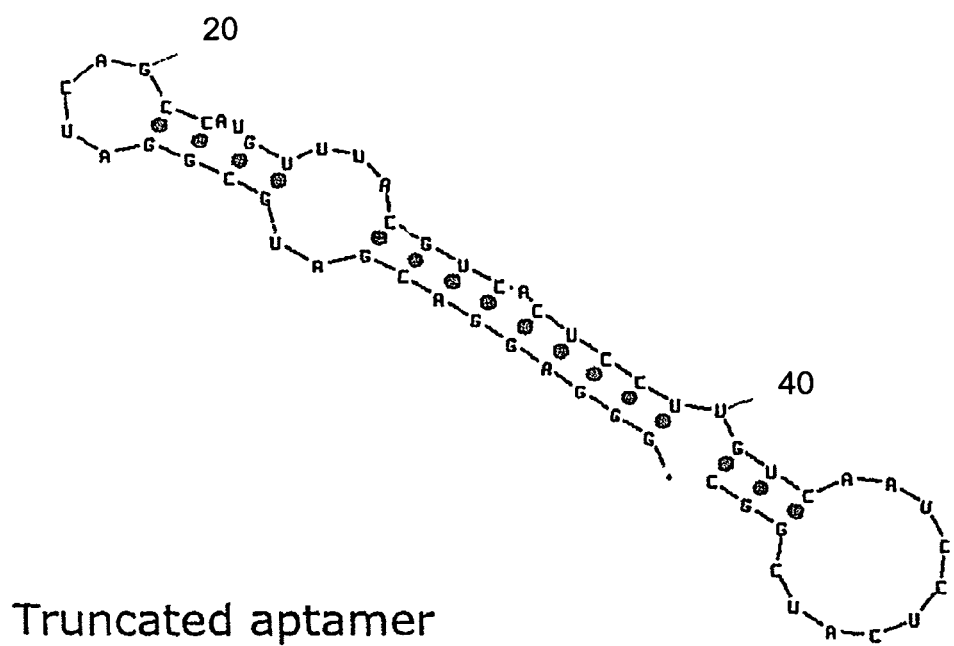
FIG. 8A depicts a truncated aptamer as in SEQ ID NO:20.
Figure 8B:
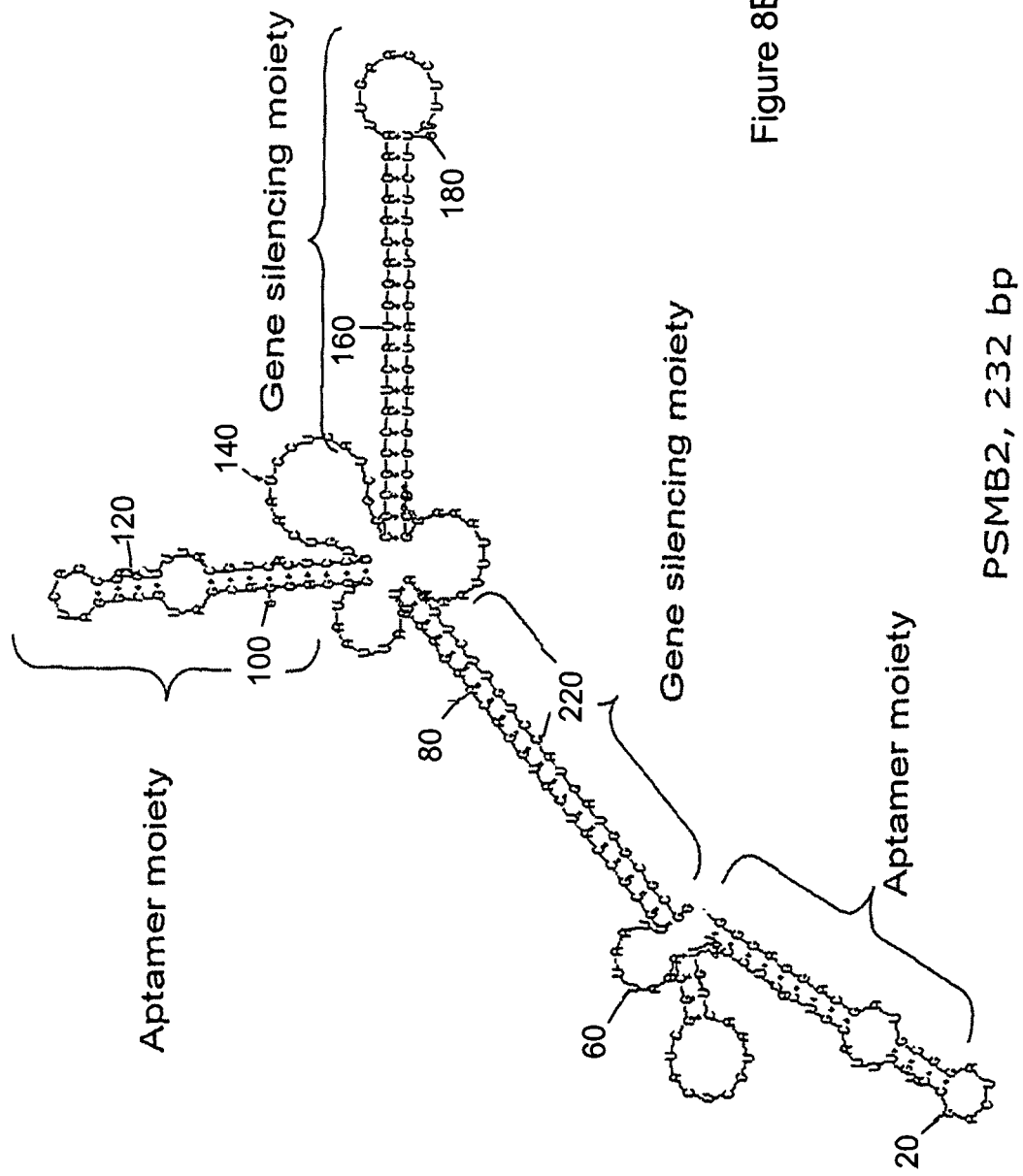
FIG. 8B depicts a bivalent aptamer siRNA construct as in SEQ ID NO:21.

In order to increase the valency of the aptamer siRNA fusion constructs a second aptamer oligonucleotide sequence was inserted in a way that both aptamer functionalities will most likely fold into their native conformation. Secondary structure analysis of the designed bivalent RNA constructs using MFold 3.2 (http://molbio.info.nih.gov/molbio-nih/mfold.html) RNA folding algorithm showed that in both constructs (PSMB1-siEEF2 as well as PSMB2-siEEF2) the two aptamer moieties adopt the same secondary structure as the monomeric aptamer x-PSM-A-3. In addition these structures are those with the lowest calculated free energy (AG) for both constructs (FIG. 7 and FIG. 8)

Figure 9A:
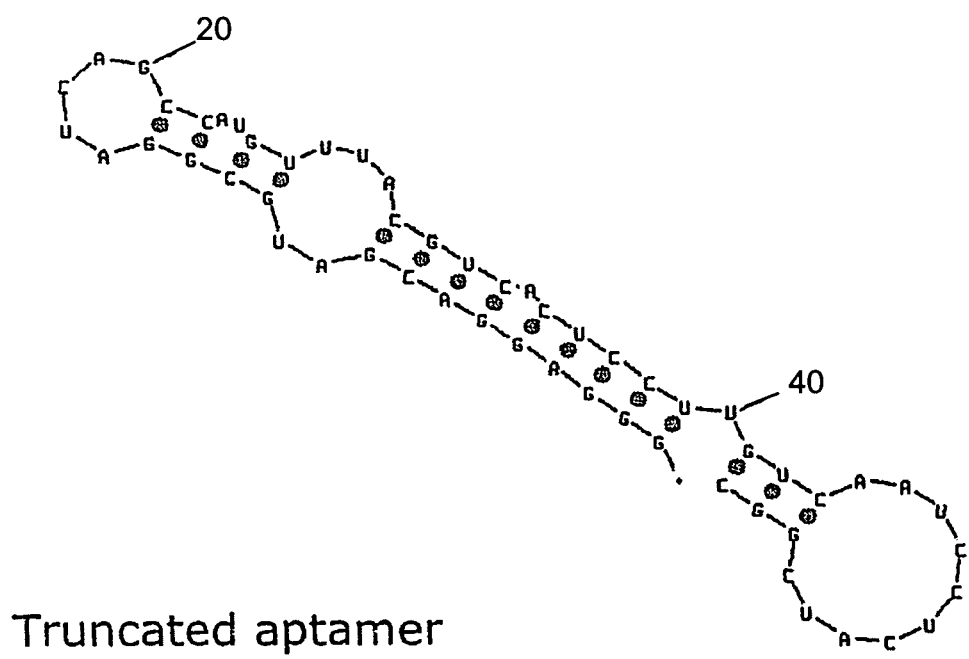
FIG. 9A depicts a truncated aptamer as in SEQ ID NO:20.
Figure 9B:
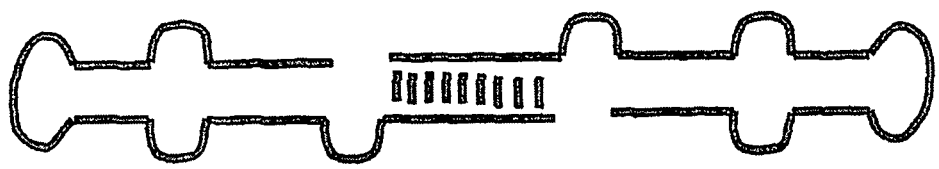
FIG. 9B schematically depicts PSMA Biv anneal.

In addition to PSMB1-siEEF2 and PSMB2-siEEF2 a third construct was designed in which both aptamer moieties are fused via Watson Crick base pairing using complementary 3' overhangs which resemble the siRNA moiety (FIG. 9).

Test of the Specific Silencing Effects of the Full RNA-Constructs

To test the aptamer-shRNA constructs concerning their specific gene silencing function, three different RNA-constructs, two against GFP and one against EEF2, were transfected by lipofection into 293-LGFP-KMH cells. siRNAs against GFP and EEF2 were used as positive controls.

Surprisingly, although in the case of the aptamer-shRNA constructs the siRNA is covalently linked to the aptamer, the effects of the aptamer-shRNA constructs and the unconjugated siRNA were almost the same. Thus, a gene silencing activity of the siRNA part is not affected by a covalently attached aptamer.

Figure 10:
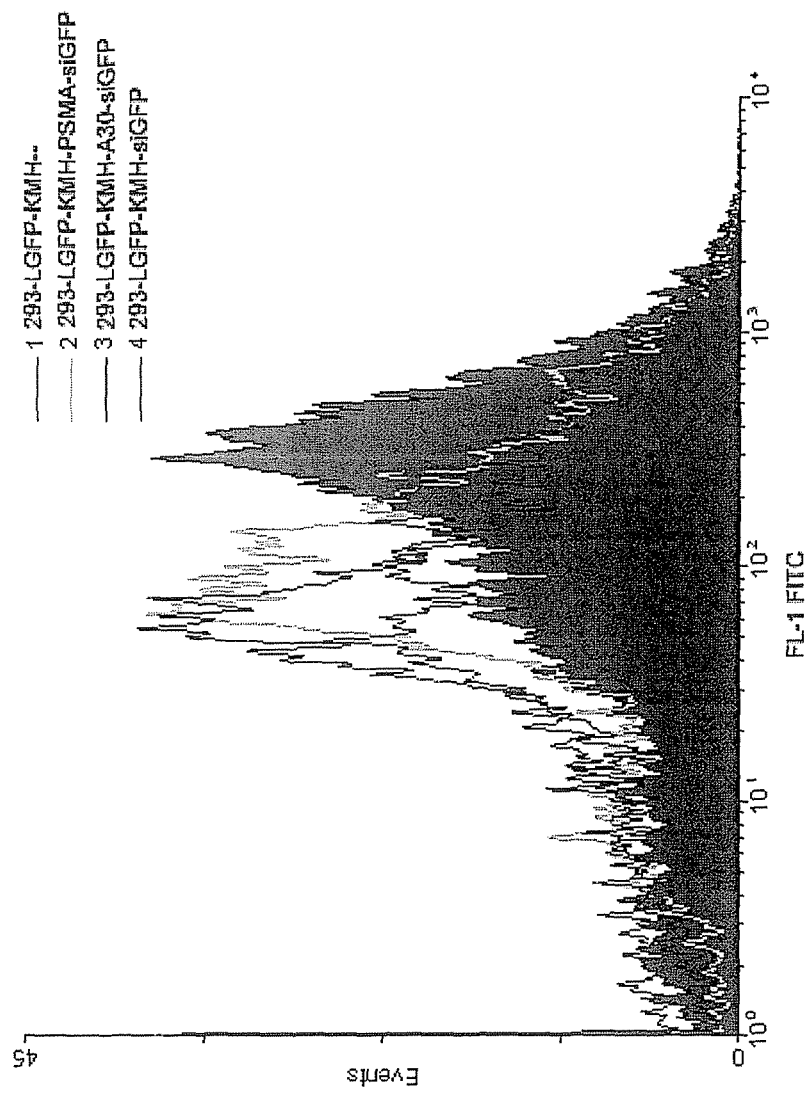
FIG. 10 is a plot of a flow cytometry analysis result as related to a test of the specific silencing effects of the full RNA-constructs.
Figure 11:
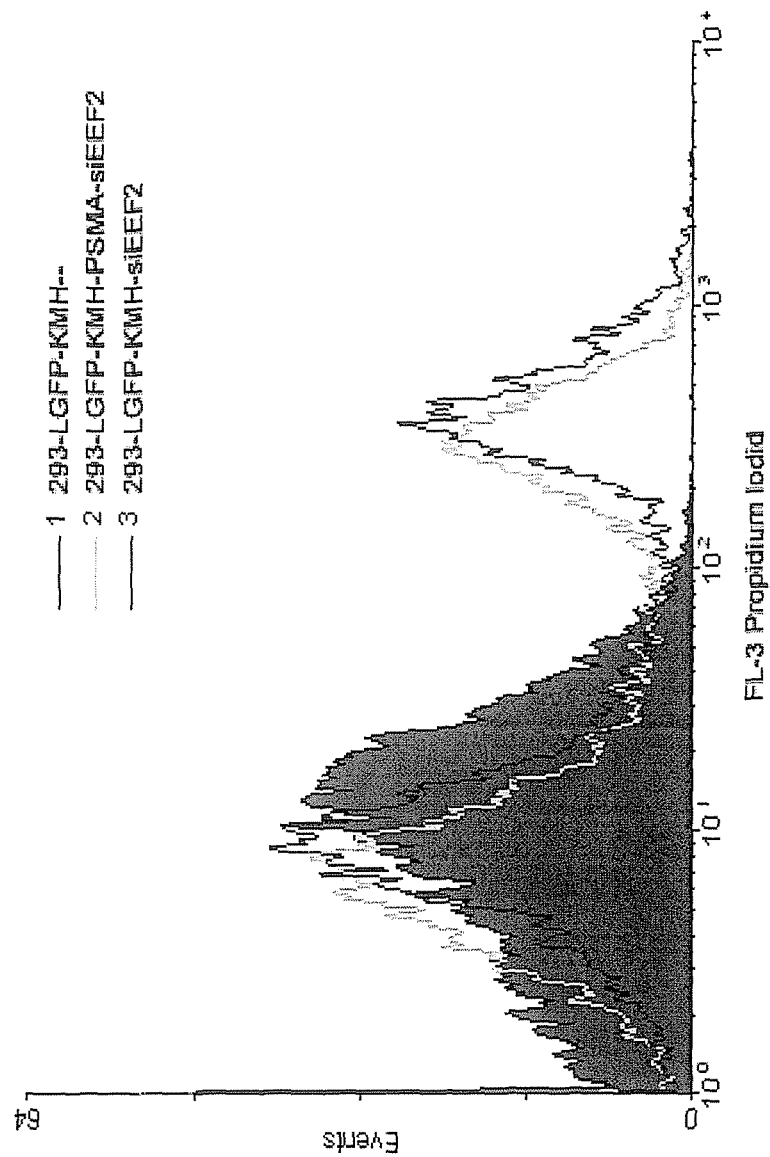
FIG. 11 is a plot of a flow cytometry analysis result as related to a test of the specific silencing effects of the full RNA-constructs.

In FIG. 10 the reduced expression of GFP (about 60%) in 293-LGFP-KMH cells is shown after transfection of the aptamer-constructs and siRNA against GFP. Staining with propidium iodide is used to detect the amount of apoptotic cells. Cells transfected with the aptamer-shRNA-constructs as well as siEEF2 and stained with propidium iodide were analyzed by flow cytometry 48 h after transfection (FIG. 11). The cells were washed twice with cold 1×PBS and finally resuspended in a sample amount of 500 μl 1×PBS. A significant amount of apoptotic cells in siRNA-containing samples of transfected in contrast to non-transfected cells was detected.

Binding Properties of Antibodies, Aptamers, Protein-RNA-Constructs and Full RNA-Constructs
The Aptamer A30

Figure 12:
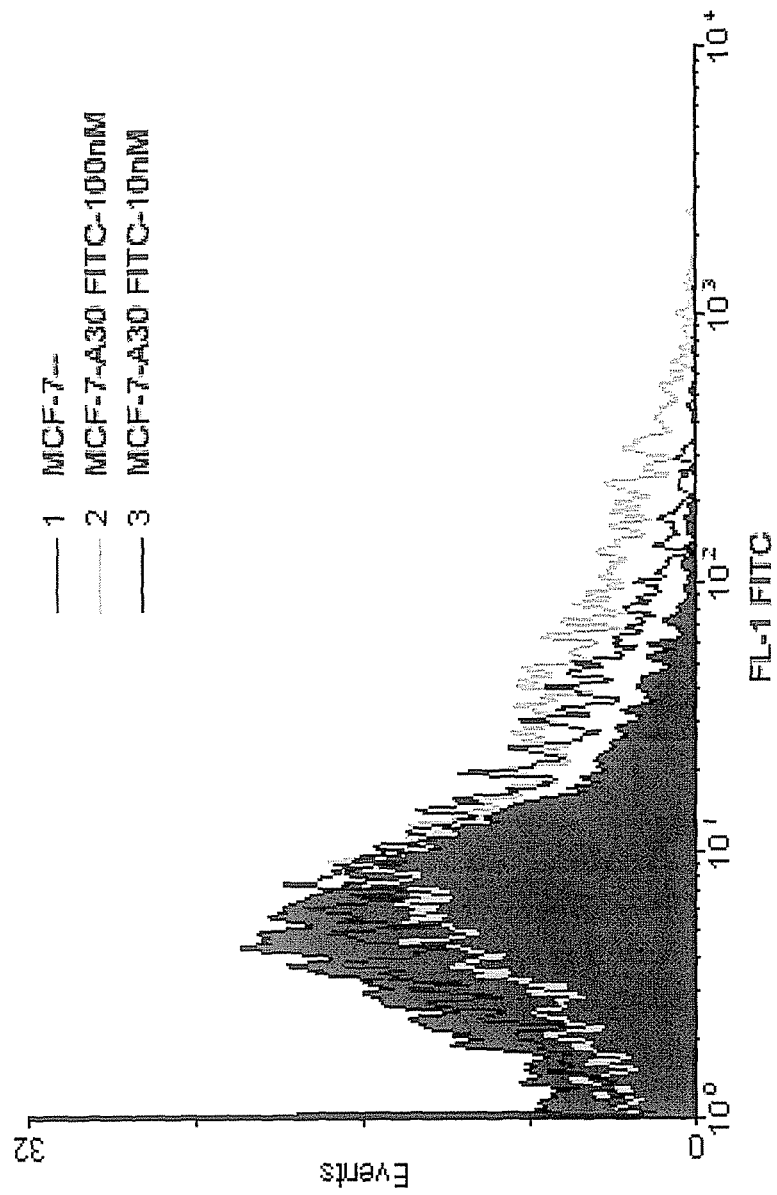
FIG. 12 is a plot of a flow cytometry analysis result as related to binding properties of antibodies, aptamers, Protein-RNA-constructs and full RNA-constructs.
Figure 13:
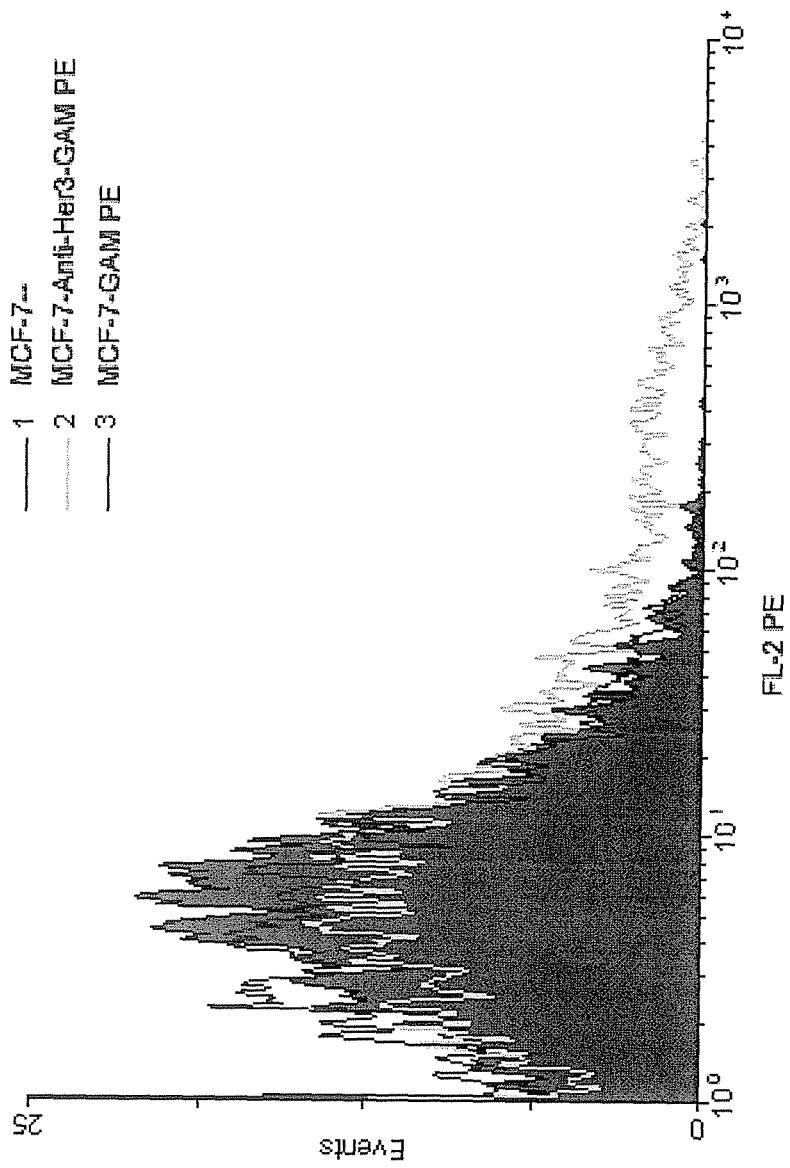
FIG. 13 is a plot of a flow cytometry analysis result as related to binding properties of antibodies, aptamers, Protein-RNA-constructs and full RNA-constructs.

The aptamer A30 was analyzed on its binding affinity to Her3 on MCF-7 cells. As negative control the cell line L540 (Her3 negative) was used. The RNA was 3' oxidized and FITC-labeled allowing analysis of binding to cells by flow cytometry. We used the FITC-labeled aptamer A30 in different concentrations and in parallel the antibody Anti-Her3 which specifically binds Her3 as the secondary antibody GAM IgG PE which binds to the fc part of Anti-Her3 antibody was used. The cells were washed twice with cold 1×PBS, resuspended in 500 μl 1×PBS and incubated for 30 min with different concentrations of FITC-labeled A30 in the dark or with the primary antibody Anti-Her3. After the first incubation step cells were washed twice with cold 1×PBS and either, after the Incubation with the FITC-labeled A30, resuspended in 500 μl 1×PBS and analysed by flow cytometry (shown in FIG. 12) or, after the incubation with Anti-Her3, resuspended in 500 μl 1×PBS and incubated 30 min with the secondary antibody GAM IgG PE in the dark. After the second incubation step cells were washed again with 1×PBS, resuspended in 500 μl 1×PBS and finally analysed by flow cytometry (shown in FIG. 13).

To ensure the specific binding of A30 to the antigen Her3 on MCF-7 cells, the aptamer was tested for its binding affinity onto L540 cells where no binding could be detected (data not shown).

Figure 14:
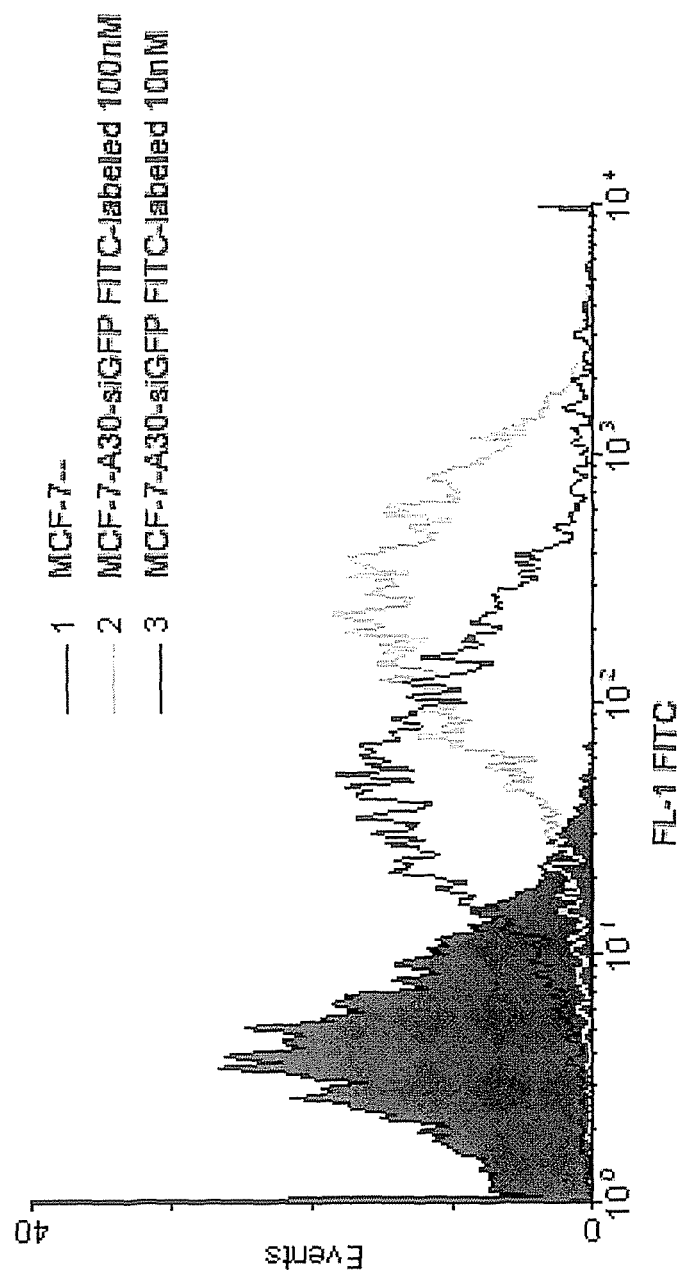
FIG. 14 is a plot of a flow cytometry analysis result as related to binding properties of antibodies, aptamers, Protein-RNA-constructs and full RNA-constructs.

After testing the binding of the aptamer, the aptamer-shRNA fusion construct of A30 was analyzed by flow cytometry (shown in FIG. 14). For this experiment the cells were separated by filtration through a 100 μm sieve immediately before FACS analysis which resulted in a more homogenous cell population.

Figure 15:
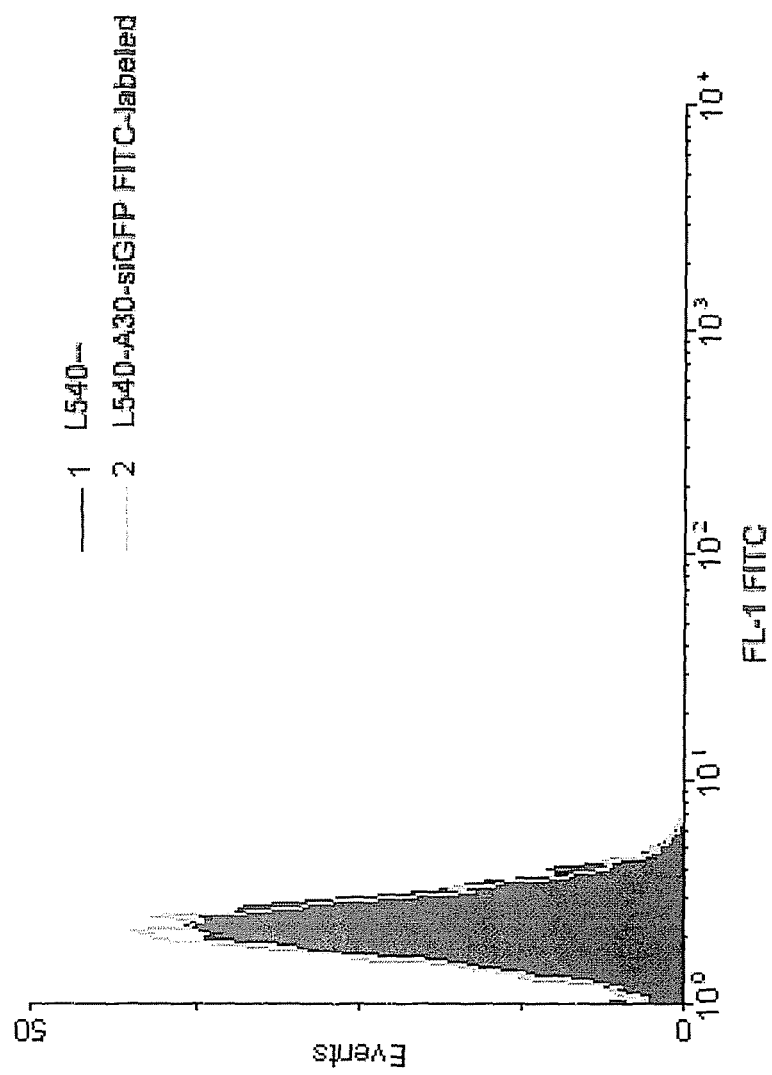
FIG. 15 is a plot of a flow cytometry analysis result as related to binding properties of antibodies, aptamers, Protein-RNA-constructs and full RNA-constructs.

To show the specificity of the aptamer-shRNA-construct, it also was tested on L540 cells where no binding of the construct was visible (shown in FIG. 15).

The Aptamer xPSM-A-3

Figure 16:
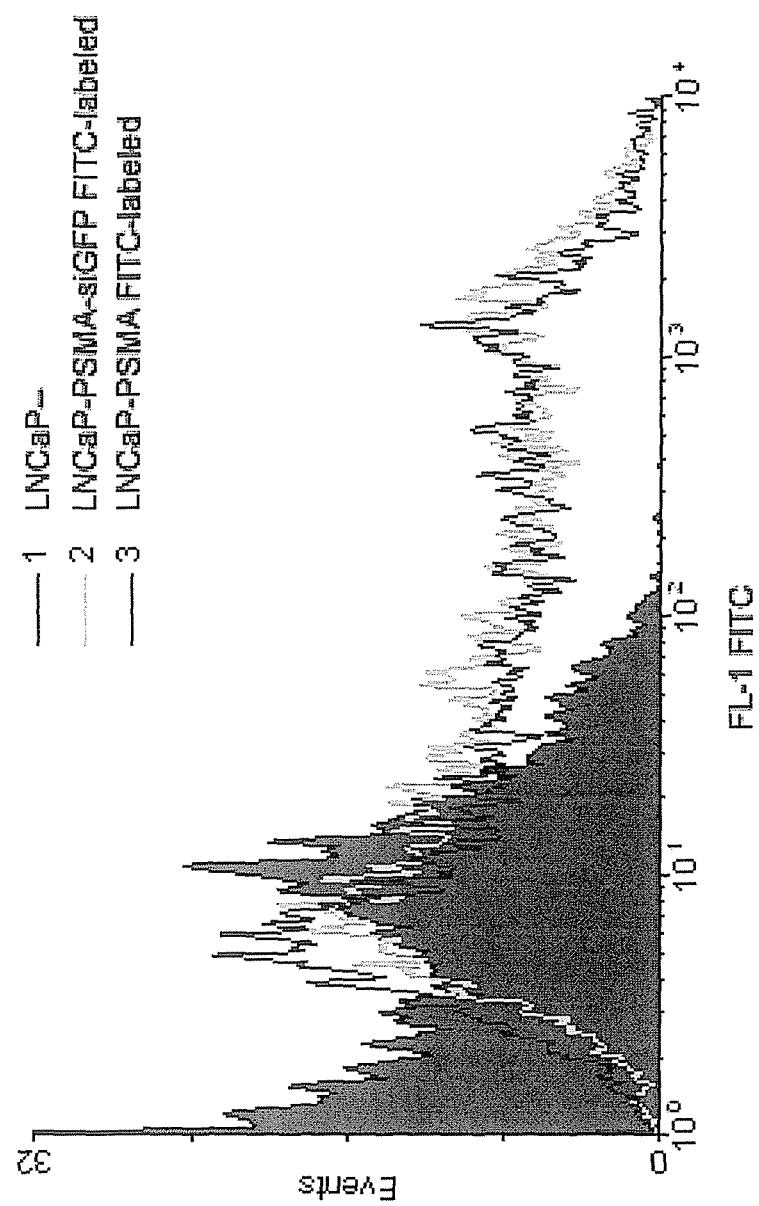
FIG. 16 is a plot of a flow cytometry analysis result as related to the aptamer xPSM-A-3.
Figure 17:
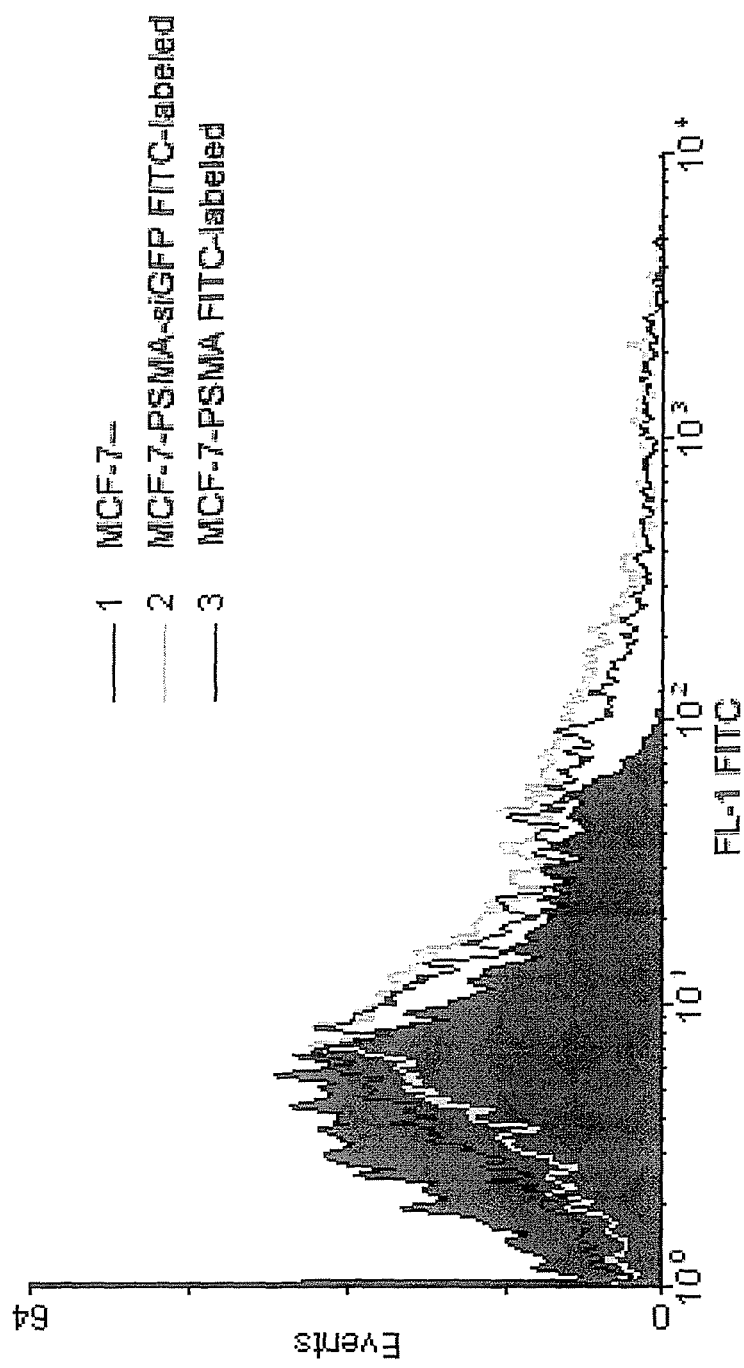
FIG. 17 is a plot of a flow cytometry analysis result as related to the aptamer xPSM-A-3.
Figure 18:
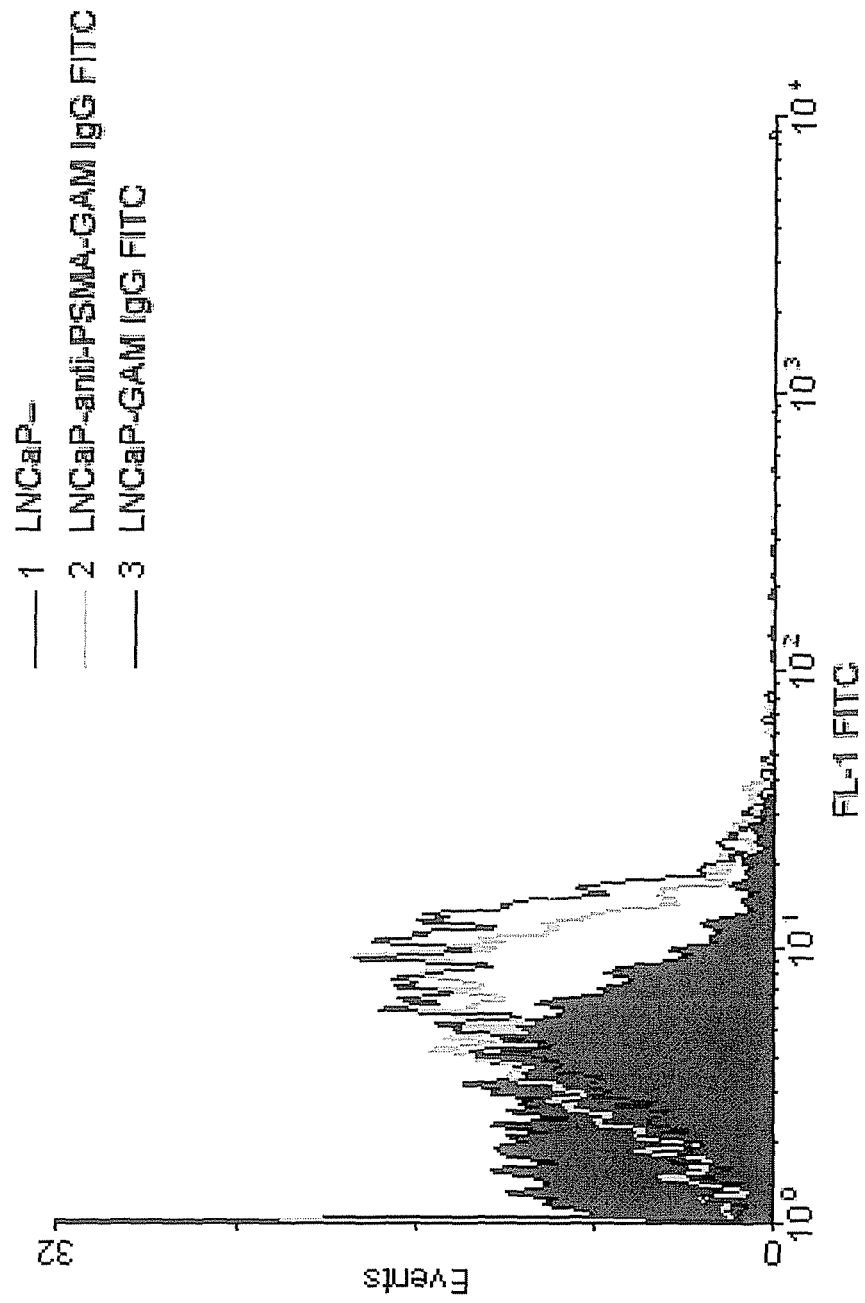
FIG. 18 is a plot of a flow cytometry analysis result as related to the aptamer xPSM-A-3.
Figure 19:
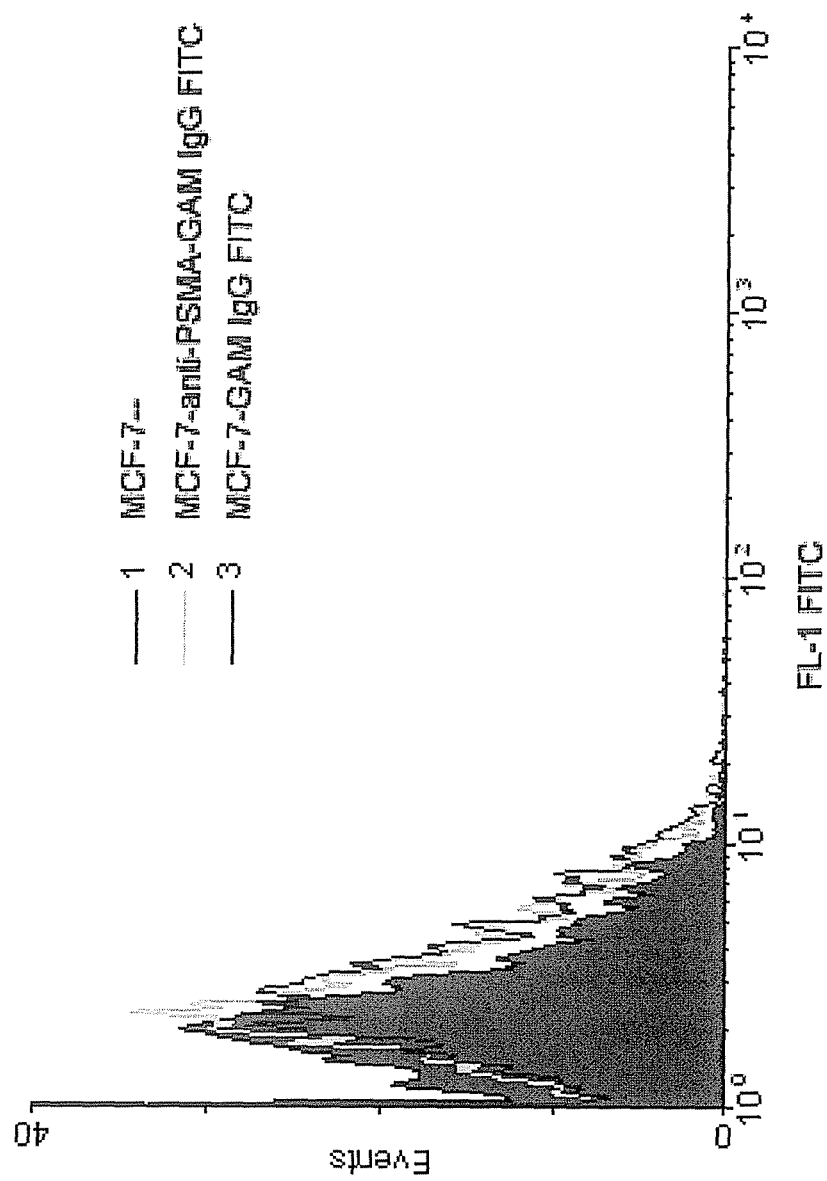
FIG. 19 is a plot of a flow cytometry analysis result as related to the aptamer xPSM-A-3.

As described in the literature, the aptamer xPSM-A-3 binds specifically to the antigen PSMA (Prostate Specific Membrane Antigen) expressed on the surface of LNCaP cells. To show that the aptamer binds in a high specificity to the antigen even if it is genetically fused to a shRNA, both RNAs, xPSM-A-3 and xPSM-A-3-siGFP, were FITC-labeled and analyzed regarding their binding to LNCaP and MCF-7 (PSMA-negative) cells (FIG. 16-17). The expression of PSMA on the cell membrane is verified using a specific primary antibody against PSMA (Anti-PSMA) as positive control with the secondary antibody GAM IgG FITC which binds to the fc part of Anti-PSMA antibody (FIGS. 18 and 19). The cells were prepared and separated as already described above.

Due to the results of the flow cytometric analysis where a small shift of the FITC-labeled aptamer and aptamer-shRNA construct was also visible in the histogram of MCF-7 cells, the cells were further analyzed under the fluorescent microscope.

Figure 20:
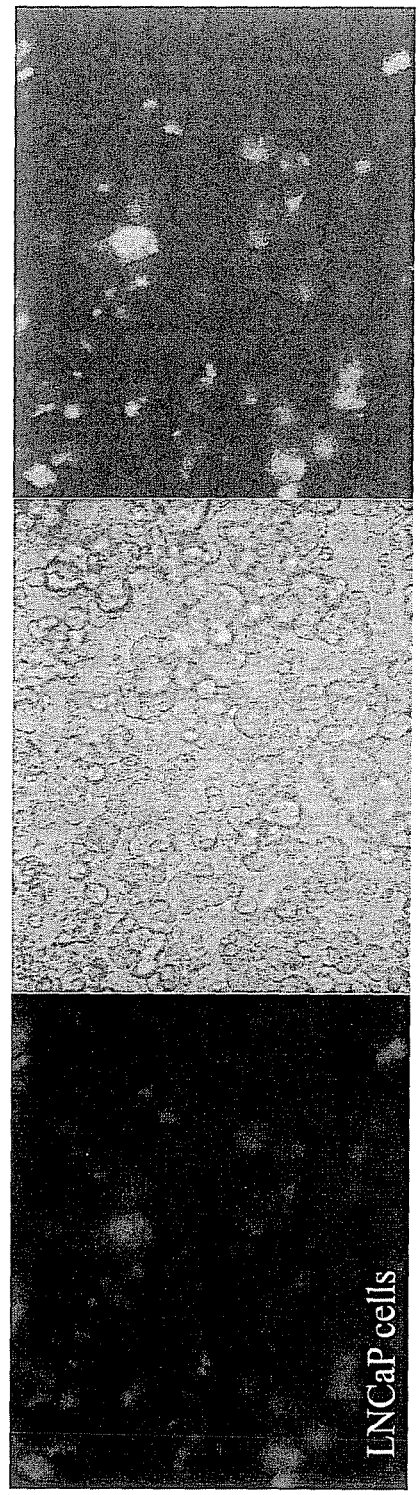
FIG. 20 is montage of a fluorescent labeling experimental result as related to the aptamer xPSM-A-3.
Figure 20:
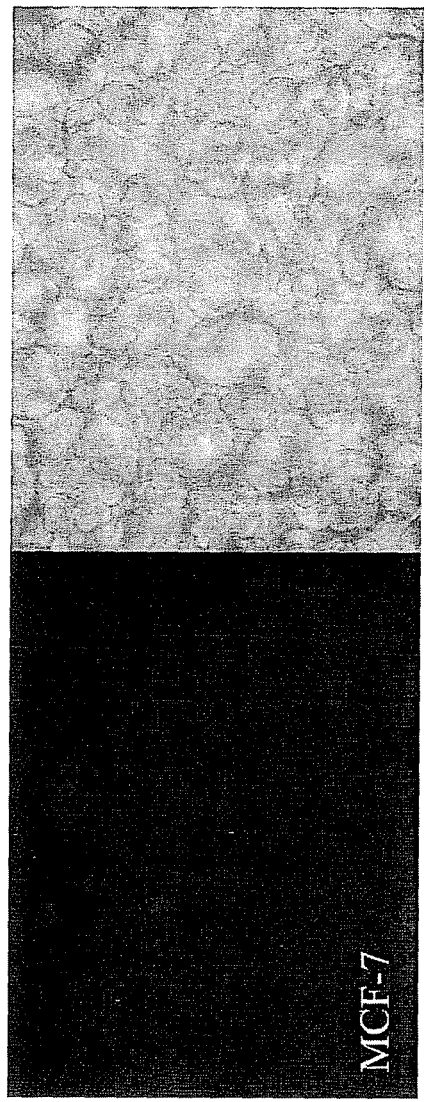

FIG. 20 shows significant staining of the surface of LNCaP cells by the FITC-labeled RNA-construct so that the shape of the stained cells is clearly visible.

In contrast PSMA-negative cell line MCF-7 is not bound by the RNA-construct. The slight background is caused by residual free fluorescein.

Finally it can be held on that the genetic fusion of the shRNA moiety, the nucleic acid moiety, to the aptamer xPSM-A-3 or A30, the targeting moiety of the complex did not affect the binding activities. Both complexes showed binding specificity in the case of xPSM-A-3 against the Prostata Specific Membrane Antigen (PSMA) presented on the cell surface of LNCaP cells and in the case of A30 against Her3, an antigen expressed on the surface of MCF-7 cells.

Figure 21:
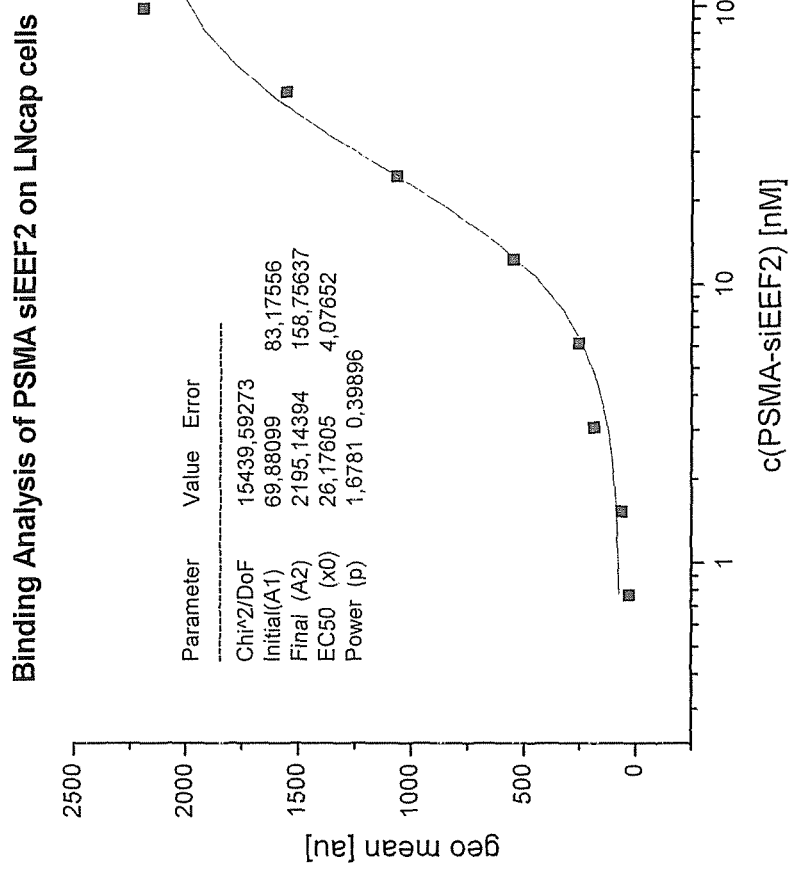
FIG. 21 is a plot of a binding analysis result as related to the aptamer xPSM-A-3.

The affinity of the x-PSM-A-3 siEEF2 was determined in a flow cytometry based equilibrium binding assay. In FIG. 21 the concentration of Fluoresceine labeled Aptamer is plotted against the mean fluorescence intensity measured in fl1 direction in arbitary fluorescence units. After sigmoidal fitting of the data the observed dissociation constant (Kd) could be determined to be 26.7 nM on the surface of LNCaP cells.

Bivalent Aptamer Construct PSMB1-siEEF2, PSMB2-siEEF2 and PSMA Biv Anneal

Figure 22:
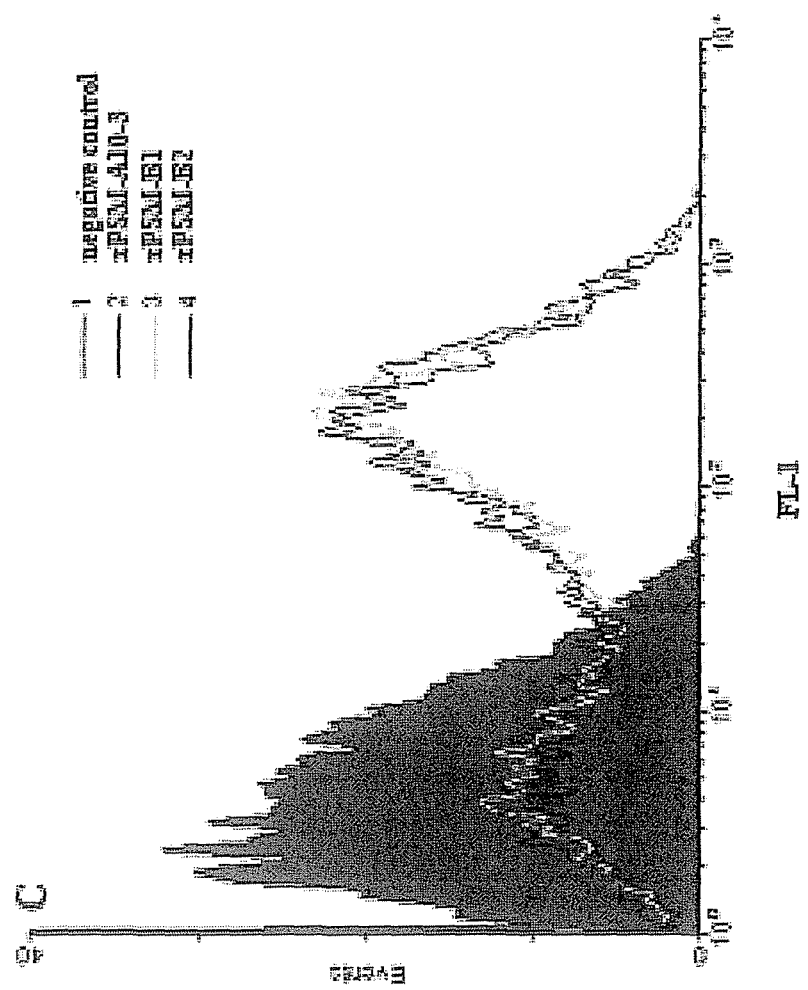
FIG. 22 is a flow cytometry analysis result as related to the bivalent aptamer construct PSMB1-siEEF2, PSMB2-siEEF2 and PSMA biv anneal.

Specific binding of bivalent aptamer siRNA constructs PSMB1-siEEF2 and PSMB2-siEEF2 is also proved via flow cytometry. Fluoresceine labeled aptamer constructs are incubated with $2*10^5$ cells at a concentration of 300 nM subsequently samples are analysed via flow cytometry. As shown in FIG. 22 both bivalent aptamer constructs show a significant shift in fl1 direction which is comparable to the shift of the monovalent xPSM-A-3. These results clearly indicate that the aptamer moieties of the bivalent aptamers fold into an active conformation that results in specific antigen recognition.

As described above the bivalent aptamer PSMA biv anneal is formed via Watson crick base pairing. Therefore both monomers are annealed prior to flow cytometric analysis. Both monomers are mixed in a 1:1 ratio in 1×PBS buffer and heated to 94° C. for 4 min and subsequently are slowly cooled to 37° C. The formed complex runs at an expected size of approximately 200 bases in an Urea PAGE gel (data not shown).

Figure 23:
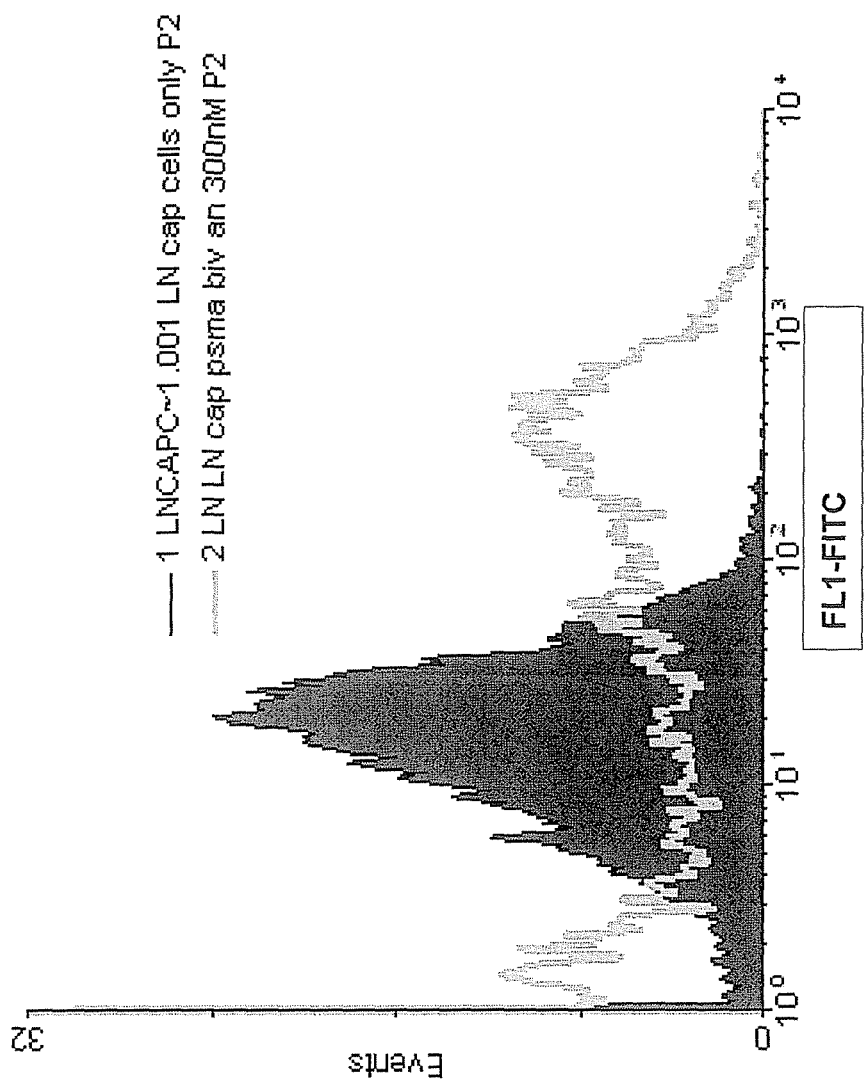
FIG. 23 is a flow cytometry analysis result as related to the bivalent aptamer construct PSMB1-siEEF2, PSMB2-siEEF2 and PSMA biv anneal.
Figure 24:
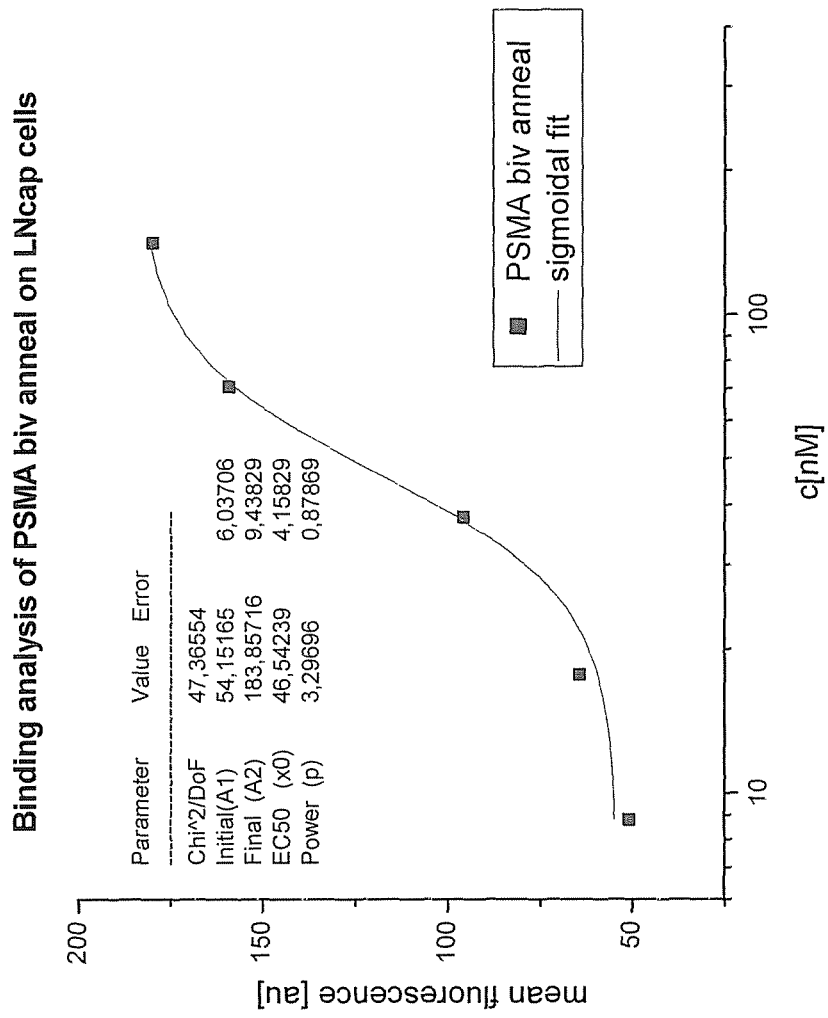
FIG. 24 is a plot of a binding analysis result as related to the bivalent aptamer construct PSMB1-siEEF2, PSMB2-siEEF2 and PSMA biv anneal.

In order to prove the specific binding of the bivalent Aptamer constructs both monomers which form the bivalent construct PSMA biv anneal are fluoresceine labeled and are joined in a hybridization reaction prior to FACS analysis. Cells are prepared as mentioned above and the annealed bivalent aptamer is used at a concentration of 300 nM. FIG. 23 shows a significant shift in FL1 direction on LNCaP cells. This indicates that both aptamer functionalities fold into their native conformation so that the bivalent aptamer binds to PSMA antigen presented on the cell surface of LNCaP cells. As for the monovalent aptamer construct x-PSM-A3 the affinity of this bivalent aptamer construct was also determined in a flow cytometry based equilibrium binding assay. FIG. 24 shows the sigmoidal curve which results from plotting the concentration of the Fluoresceine labeled PSMA biv anneal against the observed mean fluorescence in fl1 direction. The affinity (Kd) of this annealed bivalent Aptamer to the cell surface of LNCaP cells could be determined to be 46.5 nM.

The Full-Length Antibody Ki-4

Figure 25:
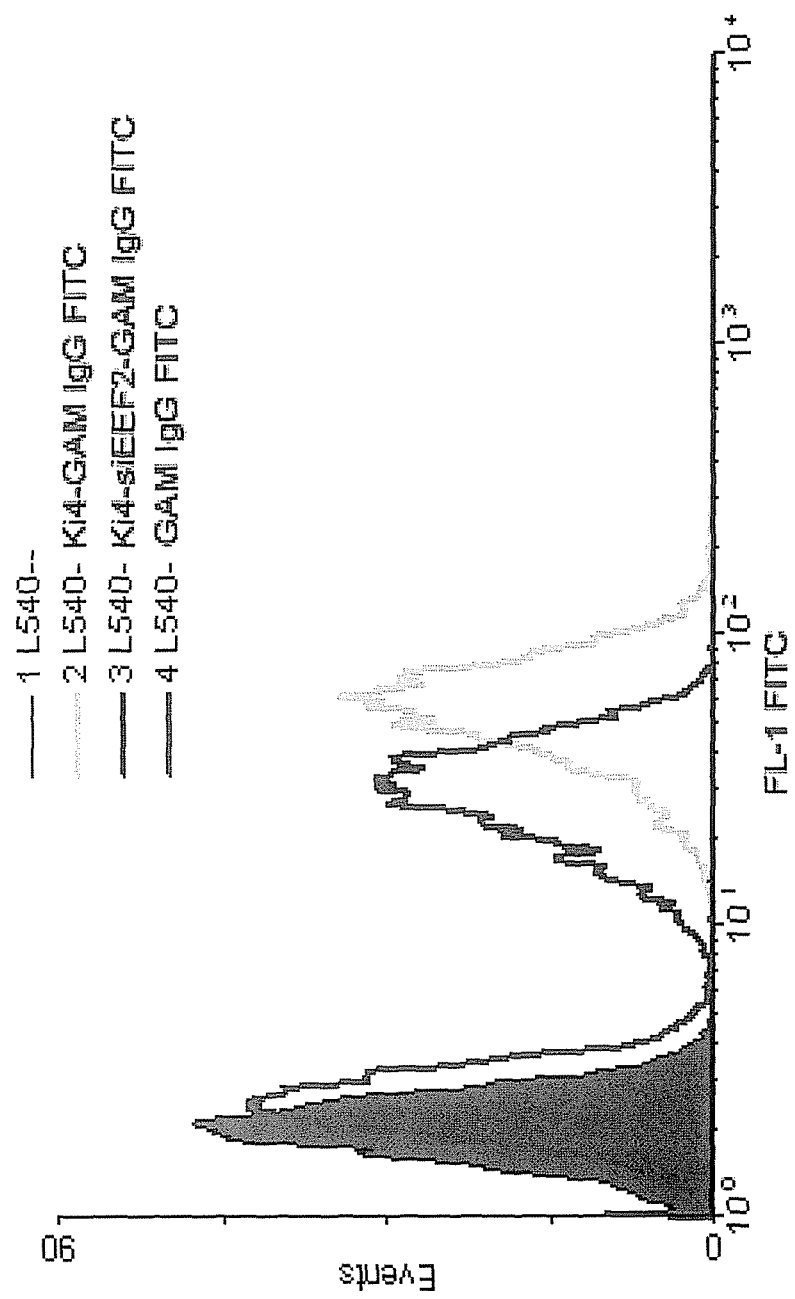
FIG. 25 is a plot of a binding analysis result as related to the full-length antibody Ki-4.
Figure 26:
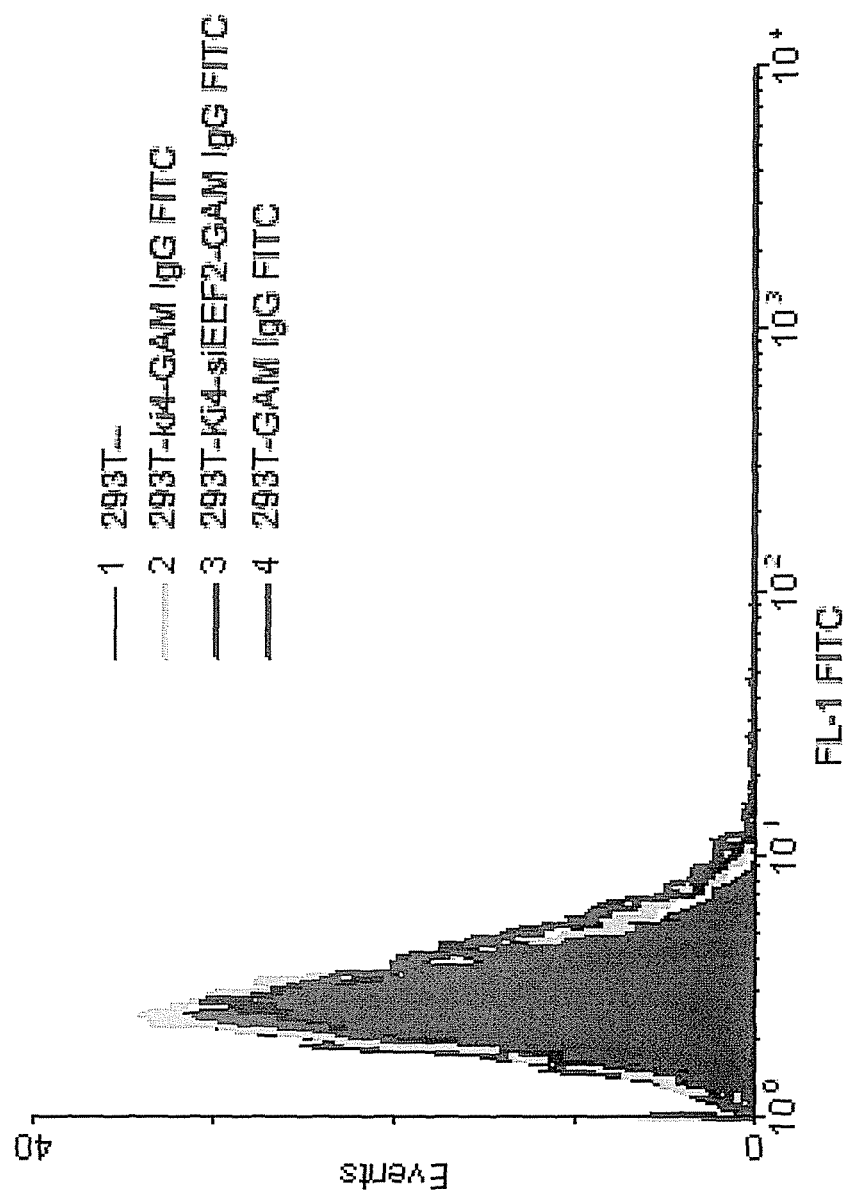
FIG. 26 is a plot of a binding analysis result as related to the full-length antibody Ki-4.

The antibody Ki-4 binds with high affinity to the CD30 receptor presented e.g. on L540 cells. As described in the literature, the antibody triggers receptor-mediated endocytosis after binding to CD30. This is why it could be possible that the antibody translocates into the cytosol. To evaluate the binding activity of Ki-4 after coupling to the siRNA, L540 cells were incubated with the protein-siRNA construct Ki-4-siEEF2 and with the unconjugated full-length antibody Ki-4 (shown in FIG. 25). The CD30-negative cell line 293T was used as negative control and incubated with the same amount of Ki-4-siEEF2 and Ki-4 (shown in FIG. 26). The cells were prepared and analyzed by Flow cytometry as mentioned above. Finally it could be observed that covalent coupling of the siRNA, the nucleic acid moiety, to the full length antibody, the targeting moiety did not affect binding activity of the resulting construct.

Analysis of the Toxicity of the siRNA-Constructs (Immuno-RNA-Constructs) A30-siEEF2, xPSM-A-3-siEEF2 and Ki-4-siEEF2

Figure 29:
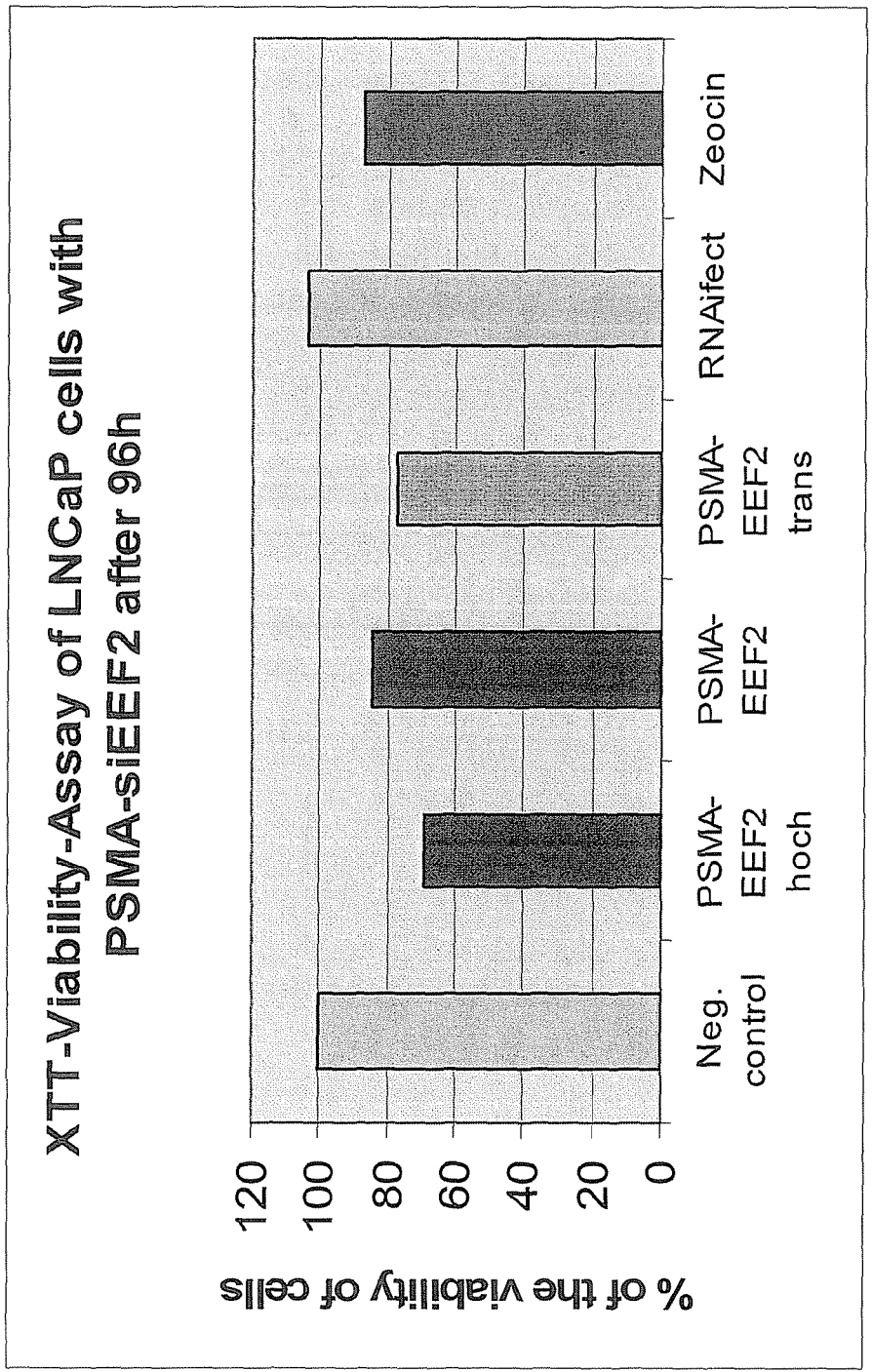
FIG. 29 is a bar graph as related to analysis of the toxicity of the siRNA-constructs (Immuno-RNA-Constructs) A30-siEEF2, xPSM-A-3-siEEF2 and Ki-4-siEEF2.
Figure 30:
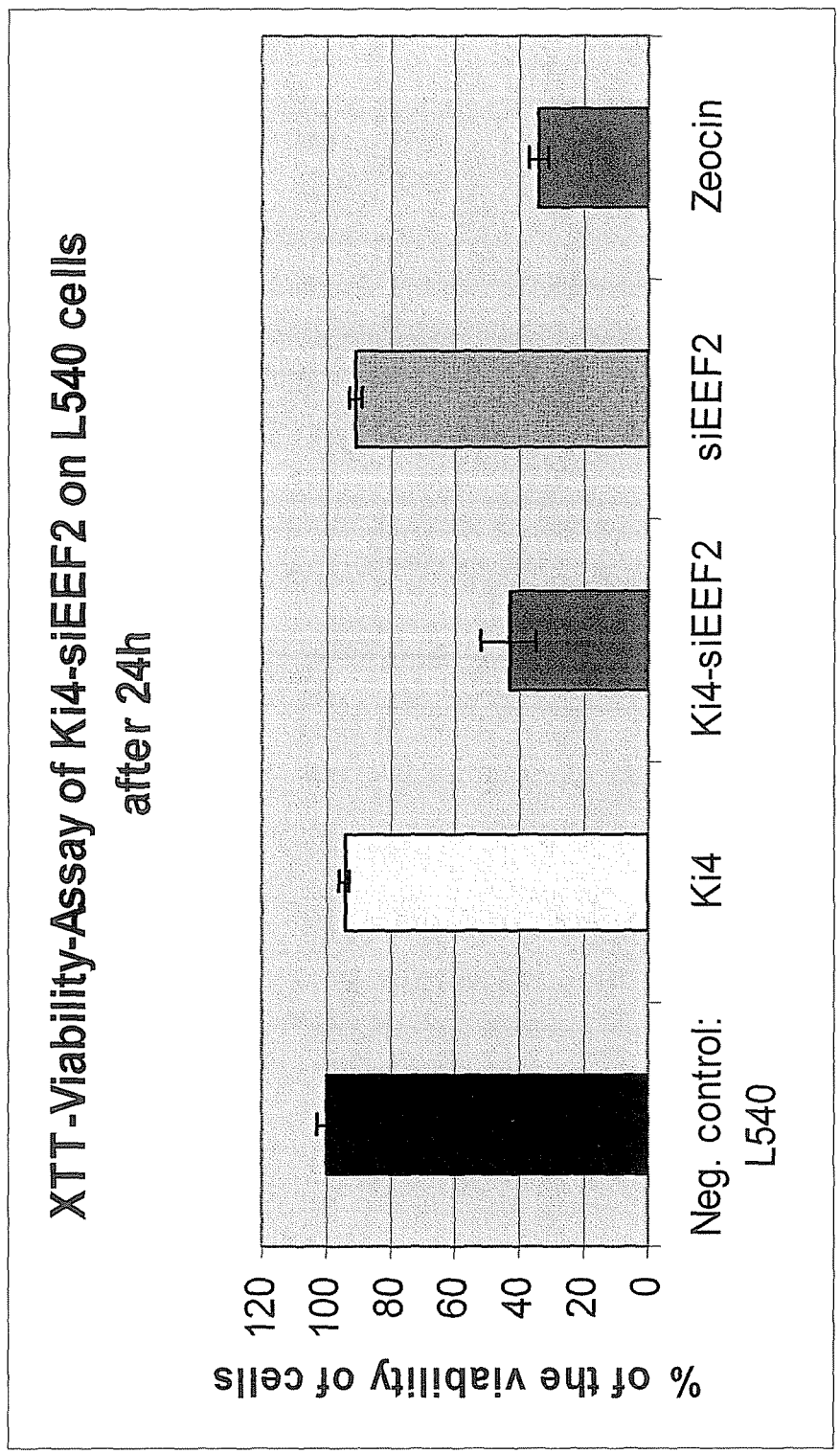
FIG. 30 is a bar graph as related to analysis of the toxicity of the siRNA-constructs (Immuno-RNA-Constructs) A30-siEEF2, xPSM-A-3-siEEF2 and Ki-4-siEEF2.

Corresponding to the documented RNAi effects after passive transfection of Immuno-RNA-Constructs into cells and the specific binding analysis, the toxic effects of the constructs on their target cells had to be analyzed. To characterize the cytotoxic activity of the Immuno-RNA-constructs comprising the targeting region (as the targeting moiety) and the RNA (as the nucleic acid moiety) in vitro, the proliferation of the target cells was evaluated after incubation with different concentrations (0.2-0.3 nmol) of the Immuno-RNA-constructs, Ki-4-siGFP, Ki-4-siEEF2, xPSM-A-3-siGFP, xPSM-A-3-siEEF2, A30-siGFP and A30-siEEF2 respectively. Growth inhibition of the cell lines MCF-7 (HER3-positive), L540 (CD30-positive) and LNCaP (PSMA-positive) were documented using a XTT-based calorimetric assay. The XTT-viability-assay provides information about the viability of the tested cells after a certain incubation time with Immuno-RNA-Constructs. Finally a XTT-Phenancin-solution was added onto the cells which were analyzed during the next 96 h (FIGS. 27, 29 and 30).

The assay is performed in 96-well-plates and measured in an ELISA-Reader at wavelengths of 450 nm (L1) and 650 nm (L2) (reduction L1-L2).

Figure 27:
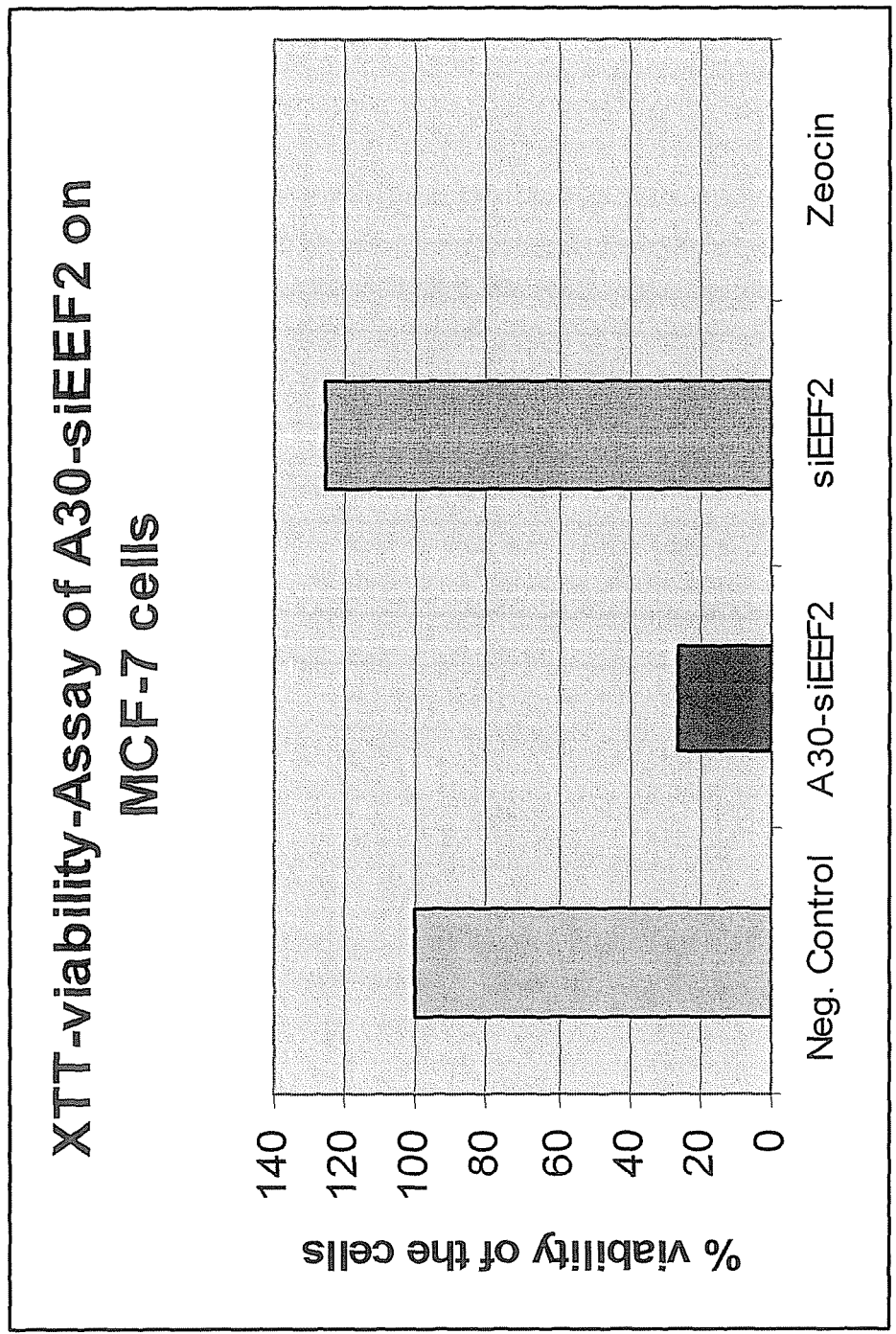
FIG. 27 is a bar graph as related to analysis of the toxicity of the siRNA-constructs (Immuno-RNA-Constructs) A30-siEEF2, xPSM-A-3-siEEF2 and Ki-4-siEEF2.

A significant difference in cell viability could be observed if cells were incubated with the immuno RNA construct A30-siEEF2 or free siEEF2 (without transfection reagent) in the same concentration (FIG. 27).

Figure 28:
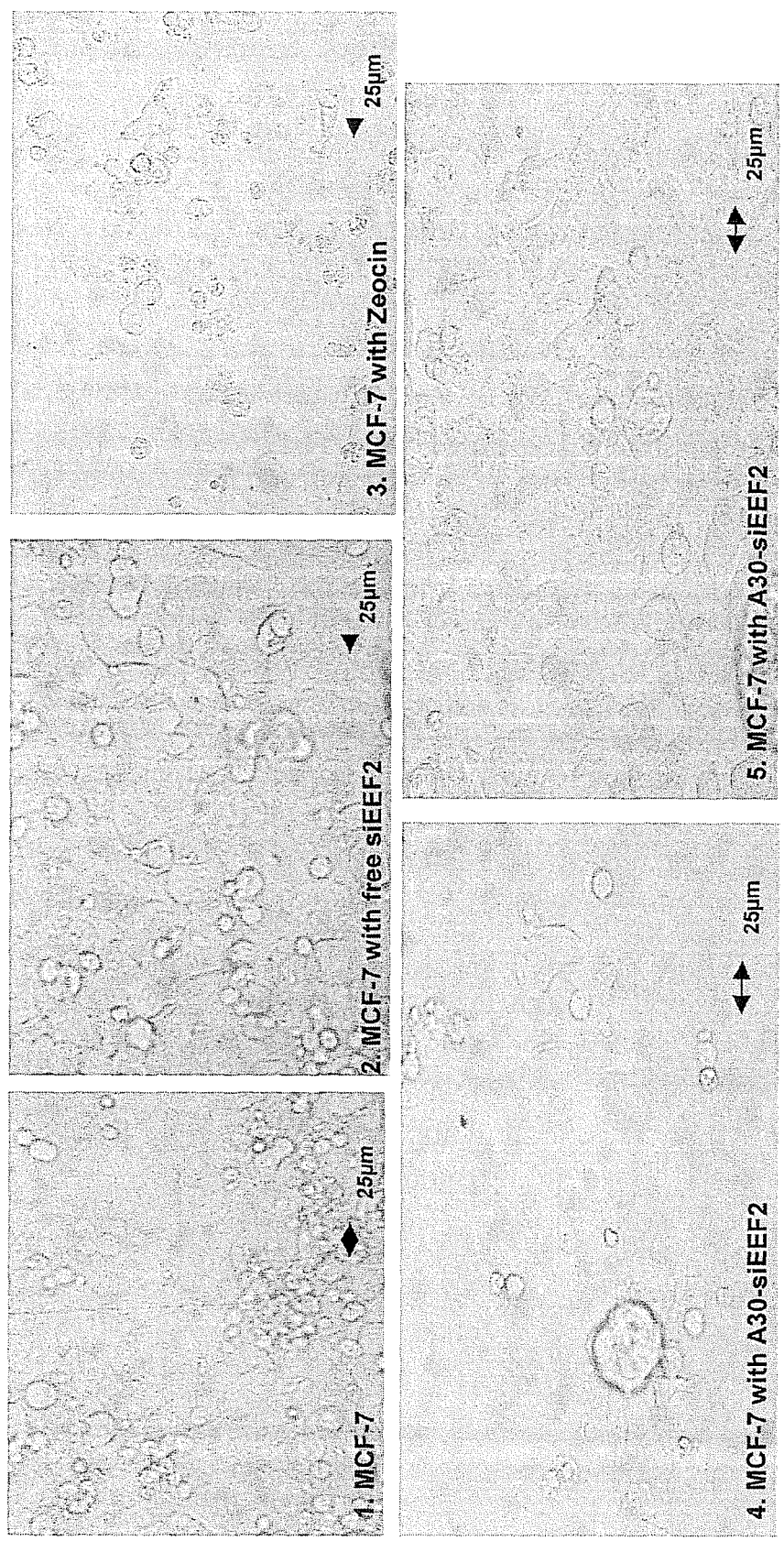
FIG. 28 is montage of microscopic images as related to the siRNA-constructs (Immuno- RNA-Constructs) A30-siEEF2, xPSM-A-3-siEEF2 and Ki-4-siEEF2.

Additionally, MCF-7 cells were investigated under microscope (FIG. 28). Corresponding to the results of the XTT-viability-assay, an increased number of granular cells, which is an indicator for apoptosis, could be recognized in the sample with cells incubated with A30-siEEF2.

In case of the two immuno RNA constructs Ki4-siEEF2 and xPSM-A-3-siEEF2 inhibition of proliferation could be induced in a cell type selective manner. Ki4-siEEF2 led to a reduction in viability up to 70% on L540 cells (FIG. 30) and xPSM-A-3-siEEF2 reduced the proliferation of up to 50% (FIG. 29).

The CD30- and PSMA-negative cell line MCF-7 was in both last cases not affected by one of the Immuno-RNA-construct, xPSM-A-3-siEEF2 and Ki-4-siEEF2 (data not shown). Concentrations of up to 10 µg/ml were used. Thus the targeting moiety (Ki-4 binding CD30 and anti-PSMA binding to PSMA) of the complex conferred specificity to the whole Immuno-RNA-constructs.

Figure 31:
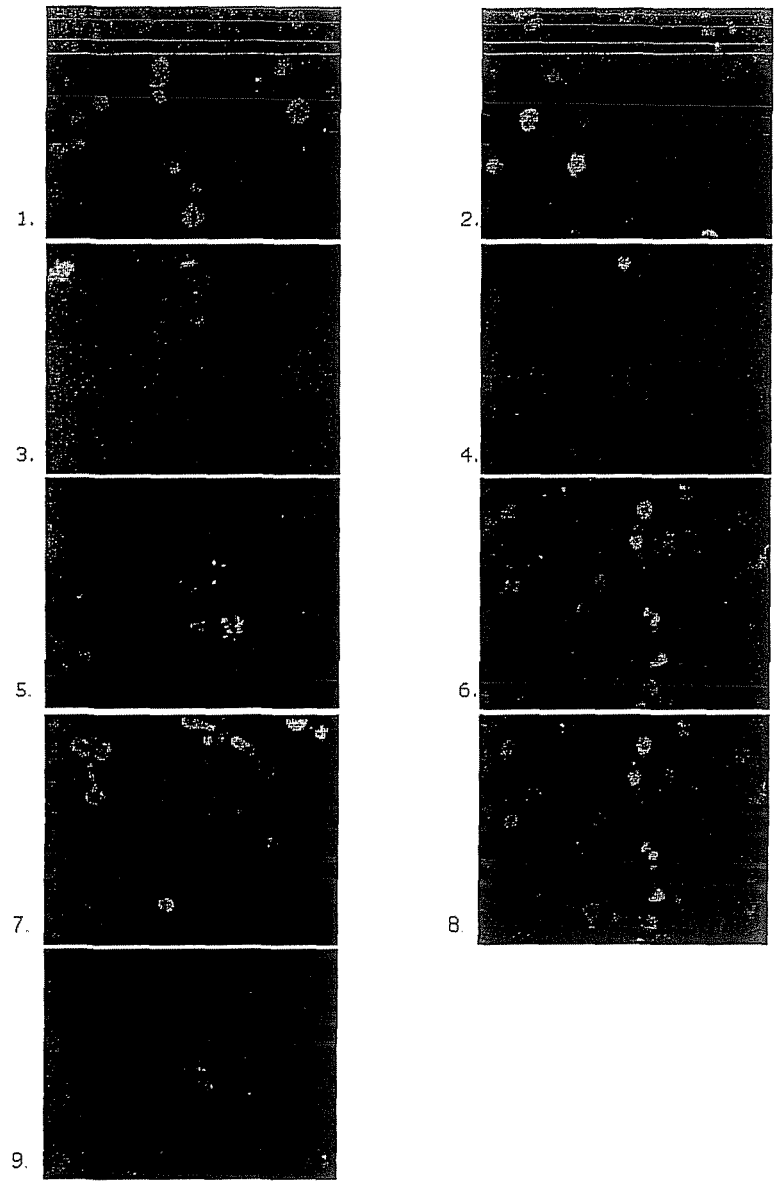
FIG. 31 is montage of a fluorescent labeling experimental result as related to analysis of the toxicity of the siRNA-constructs (Immuno-RNA-Constructs) A30-siEEF2, xP SM-A-3-siEEF2 and Ki-4-siEEF2.

In addition to the results of the XTT-viability-assay, cells were investigated in the Opera System (Evotec Technologies, Hamburg, Germany). Opera is a high through-put imaging system which is able to show in detail the changes of the morphology of cells after the application of the Ki-4-RNA-construct. The cells were stained by a Nucleus-staining with Drug 5 to visualize the whole cell and finally viewed in a 40.000 fold resolution. In contrast to cells incubated with Ki-4-siGFP or free siEEF2, cells treated with Ki-4-siEEF2 showed an augmented number of apoptotic cells (FIG. 31, pictures 1 to 9). In picture 1 L540-GFP cells under their normal growing conditions are shown. Picture 2 presents L540-GFP cells treated with 1.5 µl RNAiFect Transfection Reagent (Qiagen GmbH). In picture 3 cells were treated with approx. 3 µg Ki-4-siEEF2 and shows significant effects of the construct concerning to the shape and the viability. Picture 4 shows cells incubated with the same concentration of protein-constructs, but the silencing effect of siRNA is directed against GFP. Here are no changes in the morphology and viability of cells are visible but the expression of GFP seems to be reduced. Picture 5 and 6 present cells transfected with 0.2 nmol siRNA against EEF2 or GFP and 1.5 µl RNAiFect as positive control. Corresponding to the amount of transfected RNA, picture 7 and 8 shows the effects of 0.2 nmol free siRNA. The RNA doesn't effect the cells in any way. As positive control for the XTT-viability-Assay cells were incubated in 1640 medium added with 100 µg/ml Zeocin.

Quantitative Proliferation Assay of RNA Based siRNA Constructs on LNCaP Cells

To further characterize the monovalent Aptamer siRNA constructs and compare them with the bivalent aptamer siRNA constructs PSMA-B1 and PSMA-B2 the proliferation assay described above was performed in a quantitative manner. Therefore concentration dependent cytotoxicity of all siRNA aptamer fusions was monitored in a range starting from 2 µM down to a concentration of 0.0022 µM. All constructs were measured in triplicates in three independent experiments. The resulting dose response curves were compared regarding the $EC_{50}$ values and regarding the maximal response obtained.

Figure 32:
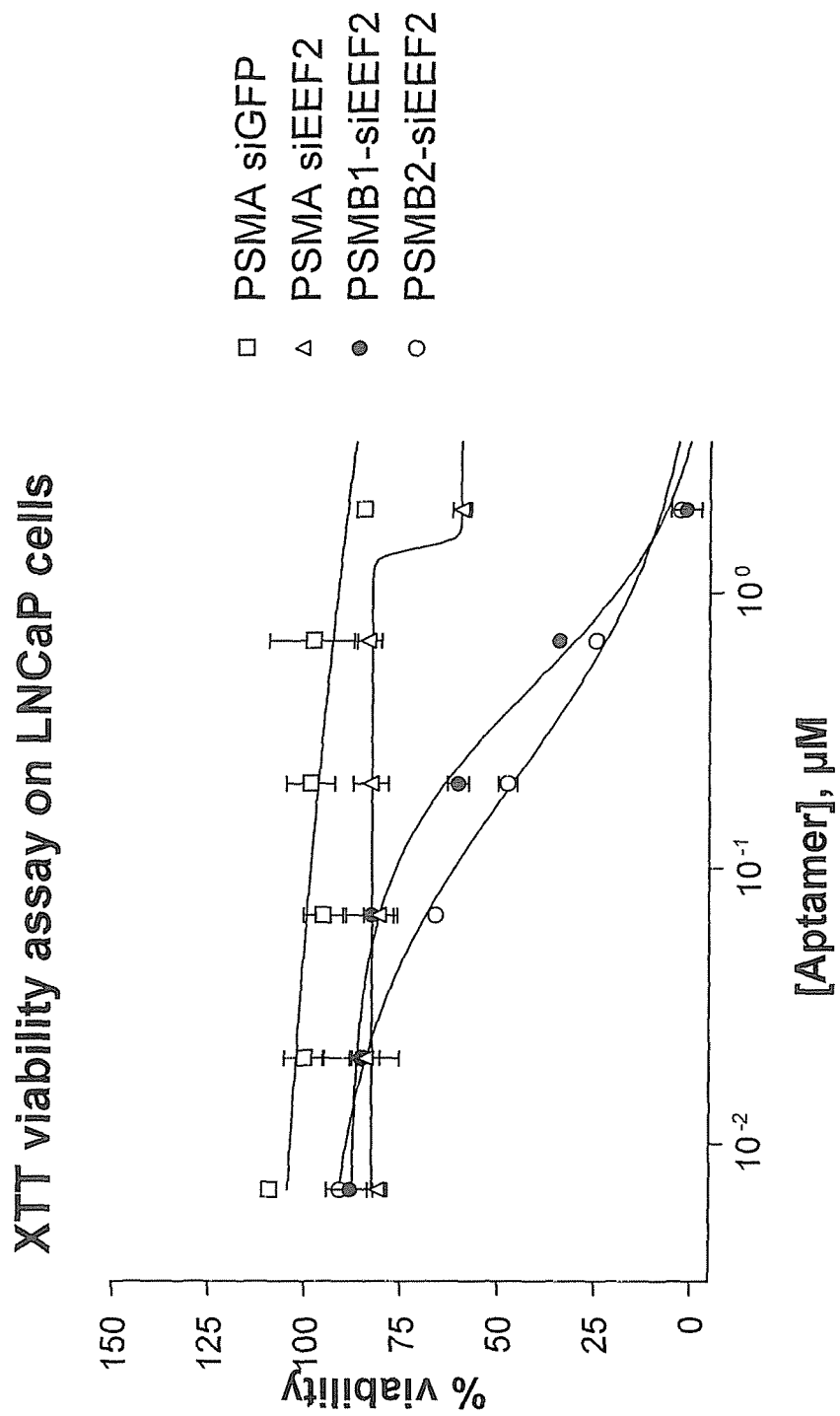
FIG. 32 is a bar graph as related to analysis of the toxicity of the siRNA-constructs (Immuno-RNA-Constructs) A30-siEEF2, xPSM-A-3-siEEF2 and Ki-4-siEEF2.

Results were shown in FIG. 32. Compared to the monovalent construct x-PSM-A-3 siEEF2 both bivalent aptamer constructs PSMAB1 and PSMAB2 show a significant higher maximum response indicating a dramatic increase in cytotoxicity. In addition both bivalent constructs show a significantly lower $EC_{50}$ (PSMB1-siEEF2: 0.517 µM, PSMB2-siEEF2: 0.211 µM xPSM-A-3 siEEF2: 1.51 µM) value which is a further parameter for higher efficacy. In summary these results clearly show that increased valency leads to improved cytotoxic efficacy.

If PSMB1-siEEF2 and PSMB2 siEEF2 are compared one has to quote that the maximum response of both constructs is in the same range but if the corresponding $EC_{50}$ values are compared a significant difference could be shown (PSMB1-siEEF2: 0.5174±0.1246 µM; N=3; PSMB2-siEEF2: 0.2115±0.01282 µM N=4; p: 0.0336 *). Since both constructs only differ in the number of siRNA sequences present within the RNA (PSMB1-siEEF2=one siRNA moiety, PSMB2-siEEF2=two siRNA moieties) this result clearly indicates that the overall efficacy of such constructs is dependent on the siRNA soichiometry.

Figure 33:
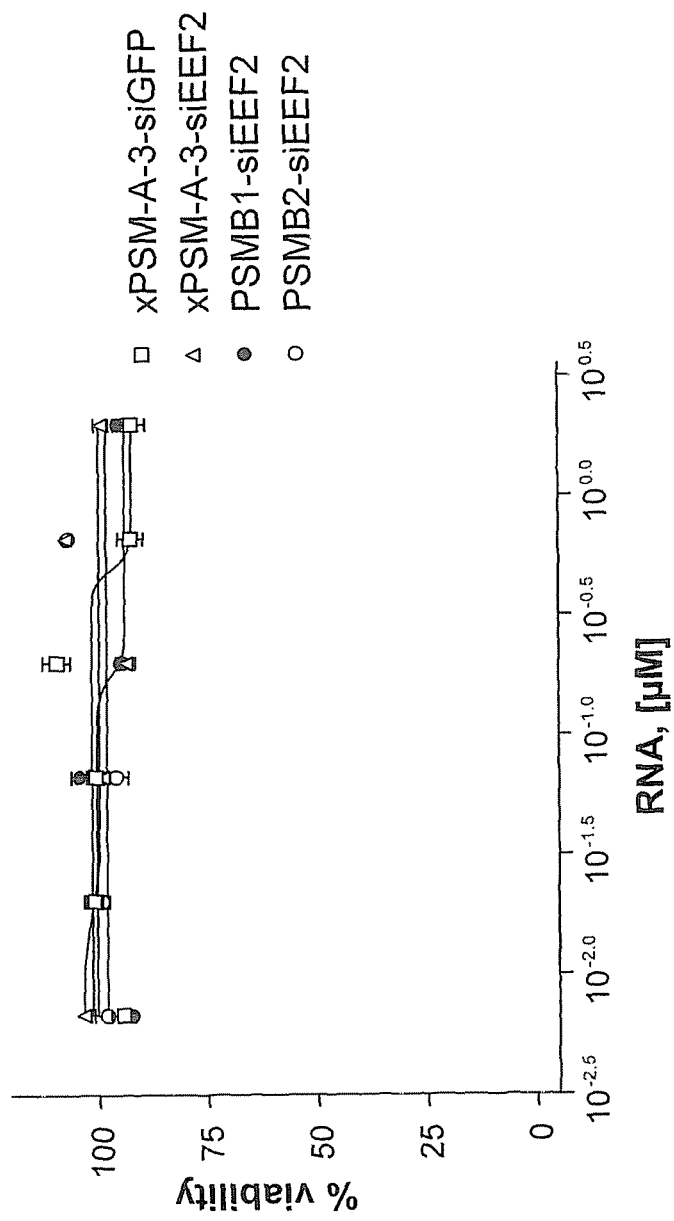
FIG. 33 is a plot of cell viability as related to a quantitative proliferation assay of RNA based siRNA constructs on LNCaP cells.

All effects were cell type selective since the immuno RNA conjugates presented here did not induce any cytotoxic effects on PSMA negative MCF-7 cells (FIG. 33).

References

1. Kaminski, M. S., Zasadny, K. R., Francis, I. R., Fenner, M. C., Ross, C. W., Milik, A. W., Estes, I., Tuck, M., Regan, D., Fisher, S., Glenn, S. D. & Wahl, R. L. (1996) *J Clin Oncol* 14, 1974-81.
2. Pennell, C. A. & Erickson, H. A. (2002) *Immunol Res* 25, 177-91.
3. Chaudhary, V. K., Jinno, Y., FitzGerald, D. & Pastan, I. (1990) *Proc Natl Acad Sci USA* 87, 308-12.
4. Brinkmann, U., Keppler-Hafkemeyer, A. & Hafkemeyer, P. (2001) *Expert Opin Biol Ther* 1, 693-702.
5. Dykxhoorn, D. M., Palliser, D. & Lieberman, S. (2006) *Gene Ther* 13, 541-52.
6. Dykxhoorn, D. M., Novina, C. D. & Sharp, P. A. (2003) *Nat Rev Mol Cell Biol* 4, 457-67.
7. Chiu, Y. L., Ali, A., Chu, C. Y., Cao, H. & Rana, T. M. (2004) *Chem Biol* 11, 1165-75.
8. Scanlon, K. S. (2004) *Curr Pharm Biotechnol* 5, 415-20.
9. Crooke, S. T. (2004) *Curr Mol Med* 4, 465-87.
10. Karkare, S., Daniel, S. & Bhatnagar, D. (2004) *Appl Biochem Biotechnol* 119, 1-12.
11. Wadhwa, R., Kaul, S. C., Miyagishi, M. & Taira, K. (2004) *Mutat Res* 567, 71-84.
12. Izquierdo, M. (2005) *Cancer Gene Ther* 12, 217-27.
13. Song, E., Zhu, P., Lee, S. K., Chowdhury, D., Kussman, S., Dykxhoorn, D. M., Feng, Y., Palliser, D., Weiner, D. B., Shankar, P., Marasco, W. A. & Lieberman, S. (2005) *Nat Biotechnol* 23, 709-17.
14. Andre, C., Xicluna, A. & Guillaume, Y. C. (2005) *Electrophoresis* 26, 3247-55.
15. Farokhzad, O. C., Jon, S., Khademhosseini, A., Tran, T. N., Lavan, D. A. & Langer, R. (2004) *Cancer Res* 64, 7668-72.
16. Blank, M. & Blind, M. (2005) *Curr Opin Chem Biol* 9, 336-42.

The invention claimed is:

1. A compound comprising:
a targeting moiety, which specifically binds to a disease related cell surface marker,
a nucleic acid moiety which specifically induces cell death or down-regulates a specific key element of a regulatory pathway of the target cell and
a linker, which covalently links the targeting moiety to the nucleic acid moiety
wherein the nucleic acid moiety knocks-down expression of eukaryotic elongation factor 2 (eEF-2), homologues of eEF-2 or analogues of eEF-2.

2. The compound of claim 1, wherein the linker is a disulfide bond, a phosphodiester bond, a phosphothioate bond, an amide bond, an amine bond, a thioether bond, an ether bond, an ester bond or a carbon-carbon bond.

3. The compound of claim 1, wherein the targeting moiety is a nucleic acid or a polypeptide.

4. The compound of claim 1, wherein the targeting moiety is a binding ligand for a cell surface receptor.

5. The compound of claim 1, wherein the targeting moiety is at least one aptamer, an antibody, a diabody or a derivative or fragment of an antibody.

6. The compound of claim 5, wherein the targeting moiety is represented by at least two aptamers.

7. The compound of claim 1, wherein the targeting moiety is selected from the group consisting of carbohydrates, lipids, vitamins, small receptor ligands, nucleic acids, cell surface carbohydrate binding proteins and their ligands, lectins, r-type lectins, galectins, ligands to the cluster of differentiation (CD) antigens, CD30, CD40, cytokines, chemokines, colony stimulating factors, type-1 cytokines, type-2 cytokines, interferons, interleukins, lymphokines, monokines, mutants, derivatives and/or combinations of any of the above.

8. The compound of claim 1, wherein the disease related cell surface marker is selected from the group consisting of CD antigens, cytokine receptors, hormone receptors, growth factor receptors, ion pumps, channel-forming proteins, multimeric extracellular matrix proteins, metallo proteases, Her3 or PSMA.

9. The compound of claim 1, wherein the targeting moiety binds to a cell surface receptor of a target cell and mediates subsequent translocation of the compound into the cytosol of the target cell.

10. The compound of claim 9, wherein after translocation of the compound into the target cell the nucleic acid moiety induces cell death of the target cell.

11. The compound of claim 1, wherein the nucleic acid moiety is a siRNA, a shRNA an antisense DNA or RNA, a dsRNA or a miRNA.

12. The compound of claim 1, wherein the nucleic acid moiety comprises 10 to 40 nucleic acid base pairs or nucleic acid bases.

13. The compound of claim 1, wherein the nucleic acid moiety is specifically inhibitory to activity of apoptosis inhibitors.

14. The compound of claim 1 comprising an aptamer and the nucleic acid moiety linked by a phosphodiester or by a phosphothioate bond.

15. The compound of claim 1 comprising an antibody and a RNA linked by a disulfide bond.

16. The compound of claim 14 consisting of an RNA.

17. A DNA coding for the RNA of claim 16.

18. A cell, an organ or a non-human animal transfected with a RNA or DNA encoding a compound comprising:
    a targeting moiety, which specifically binds to a disease related cell surface marker,
    a nucleic acid moiety which specifically induces cell death or down-regulates a specific key element of a regulatory pathway of the target cell and
    a linker, which covalently links the targeting moiety to the nucleic acid moiety
        wherein the nucleic acid moiety knocks-down expression of eukaryotic elongation factor 2 (eEF-2), homologues of eEF-2 or analogues of eEF-2.

19. The compound of 1 further comprising a moiety, which enables purification and/or detection of the compound, facilitates translocation of the compound into the target cell and/or intracellular separation therein, and/or activates the nucleic acid.

* * * * *